US008865876B2

(12) United States Patent
Mayo et al.

(10) Patent No.: US 8,865,876 B2
(45) Date of Patent: Oct. 21, 2014

(54) ENGINEERED LECTIN OLIGOMERS WITH ANTIVIRAL ACTIVITY

(75) Inventors: Stephen L. Mayo, Pasadena, CA (US); Jennifer Keeffe, Monrovia, CA (US); Alex L. Perryman, San Diego, CA (US)

(73) Assignee: California Institute of Technology, Pasadena, CA (US)

( * ) Notice: Subject to any disclaimer, the term of this patent is extended or adjusted under 35 U.S.C. 154(b) by 775 days.

(21) Appl. No.: 12/476,660

(22) Filed: Jun. 2, 2009

(65) Prior Publication Data
US 2009/0297516 A1     Dec. 3, 2009

Related U.S. Application Data

(60) Provisional application No. 61/130,633, filed on Jun. 2, 2008.

(51) Int. Cl.
    *C07K 1/00*          (2006.01)
    *C07K 14/47*       (2006.01)
    *A61K 38/00*      (2006.01)

(52) U.S. Cl.
    CPC ......... *C07K 14/4726* (2013.01); *C07K 2319/30* (2013.01); *A61K 38/00* (2013.01)
    USPC ...................................................... 530/396

(58) Field of Classification Search
    USPC ........................................................ 530/396
    See application file for complete search history.

(56) References Cited

U.S. PATENT DOCUMENTS

2007/0264265 A1*   11/2007   Goldenberg et al. ...... 424/160.1
2011/0306758 A1     12/2011   Zhang

OTHER PUBLICATIONS

Boraston, A. B., et al., 2004, Carbohydrate-binding modules: fine-tuning polysaccharide recognition, Biochem. J. 382:769-781.*
Kelley, B. S., et al., 2002, Engineering an obligate domain-swapped dimer of cyanovirin-N with enhanced anti-HIV activity, J. Am. Chem. Soc. 124:3210-3211.*
Ziolkowska, N. E., et al., 2006, Domain-swapped structure of the potent antiviral protein griffithsin and its mode of carbohydrate binding, Structure 14:1127-1135.*
Ji, X., et al., 2005, Mannose binding lectin (MBL) and HIV, Mol. Immunol. 42:145-152.*
Bi, S., et al., 2008, Structural features of galectin-9 and galectin-1 that determine distinct T-cell death pathways, J. Biol. Chem. 283(18)1 2248-12258.*
Barrientos, L. G., et al., 2004, Flipping the switch from monomeric to dimeric CV-N has little effect on antiviral activity, Structure 12:1799-1807.*
Ziolkowska, N. E., et al., Jul. 2006, Domain-swapped structure of the potent antiviral protein griffithsin and its mode of carbohydrate binding, Structure 14:1127-1135.*

Uger, R. A., and B. H. Barber, 1998, Creating CTL targets with epitope-linked beta2-microglobulin constructs, J. Immunol. 160:1598-1605.*
Ahmad et al., "Surface Expression of the HIV-1 Envelope Proteins in *env* Gene-Transfected CD4-Positive Human T Cell Clones: Characterization and Killing by an Antibody-Dependent Cellular Cytotoxic Mechanism", Journal of Acquired Immune Deficiency Syndromes, 1994, pp. 789-798.
Ahmad et al., "Evidence for a Correlation Between Antibody-Dependent Cellular Cytotoxicity-Mediating Anti-HIV-1 Antibodies and Prognostic Predictors of HIV Infection", Journal of Clinical Immunology, 2001, vol. 21, No. 3, pp. 227-233.
Ashkenazi et al., "Immunoadhesins", Intern. Rev. Immunol., 1993, vol. 10, pp. 219-227.
Baenziger et al., "Disseminated and sustained HIV infection in CD34+ cord blood cell-transplanted Rag2$^{-/-}$γc$^{-/-}$ mice", PNAS, Oct. 24, 2006, vol. 103, No. 43, pp. 15951-15956.
Baldridge et al., "Mechanisms of Antibody-Mediated Protection against Lymphocytic Choriomeningitis Virus Infection: Mother-to-Baby Transfer of Humoral Protection", Journal of Virology, Jul. 1992, pp. 4252-4257.
Balzarini, "Targeting the glycans of glycoproteins: a novel paradigm for antiviral therapy", Microbiology, Aug. 2007, vol. 5, pp. 583-597.
Balzarini et al., "Carbohydrate-binding Agents Cause Deletions of Highly Conserved Glycosylation Sites in HIV GP120", The Journal of Biological Chemistry, Dec. 9, 2005, vol. 280, No. 49, pp. 41005-41014.
Balzarini et al., "Marked Depletion of Glycosylation Sites in HIV-1 gp120 under Selection Pressure by the Mannose-Specific Plant Lectins of *Hippeastrum* Hybrid and *Galanthus nivalis*", Molecular Pharmacology, 2005, vol. 67, No. 5, pp. 1556-1565.
Balzarini et al., "Mutational Pathways, Resistance Profile, and Side Effects of Cyanovirin Relative to Human Immunodeficiency Virus Type 1 Strains with N-Glycan Deletions in Their gp120 Envelopes", Journal of Virology, Sep. 2006, vol. 80, No. 17, pp. 8411-8421.
Barrientos et al., "Design and Initial Characterization of a Circular Permuted Variant of the Potent HIV-Inactivating Protein Cyanovirin-N", Proteins: Structure, Function, and Genetics, 2002, vol. 46, pp. 153-160.
Barrientos et al., "The Highly Specific Carbohydrate-Binding Protein Cyanovirin-N: Structure, Anti-HIV/Ebola Activity and Possibilities for Therapy", Mini-Reviews in Medicinal Chemistry, 2005, vol. 5, pp. 21-31.
Barrientos et al., "The Domain-Swapped Dimer of Cyanovirin-N is in a Metastable Folded State: Reconciliation of X-Ray and NMR Structures", Structure, May 2002, vol. 10, pp. 673-686.

(Continued)

*Primary Examiner* — Jeffrey S. Parkin
(74) *Attorney, Agent, or Firm* — KPPB LLP

(57) ABSTRACT

Engineered lectins and methods of using such reagents for both preventing and treating a broad array of viral infections are provided. The lectins of the invention are engineered in two ways, first through the enhancement of the natural mode of action of lectins against viruses through linked multimerization, and second through the creation of a new class of reagents, hereinafter referred to as a "lectibody" or "lectibodies", that engage host immune function in addition to simply binding glycosylated viral proteins via the combination of a lectin and the Fc region of an antibody in order to drive Fc-mediated effector functions including ADCC (antibody-dependent cell-mediated cytotoxicity), increased half-life, complement-dependent cytotoxicity (CDC), and antibody-dependent cell-mediated phagocytosis (ADCP) in response to a lectin-mediated carbohydrate-binding event.

10 Claims, 21 Drawing Sheets

(56) References Cited

OTHER PUBLICATIONS

Barrientos et al., "Cyanovirin-N binds to the viral surface glycoprotein, $GP_{1,2}$ and inhibits infectivity of Ebola virus", Antiviral Research, 2003, vol. 58, pp. 47-56.

Barrientos et al., "Flipping the Switch from Monomeric to Dimeric CV-N Has Little Effect on Antiviral Activity", Structure, Oct. 2004, vol. 12, pp. 1799-1807.

Becktel et al., "Protein Stability Curves", Biopolymers, 1987, vol. 26, pp. 1859-1877.

Bewley, "Solution Structure of a Cyanovirin-N:Man 1-2Man Complex: Structural Basis for High Affinity Carbohydrate-Mediated Binding to gp120", Structure, Oct. 2001, vol. 9, pp. 931-940.

Bewley et al., "The Potent Anti-HIV Protein Cyanovirin-N Contains Two Novel Carbohydrate Binding Sites That Selectively Bind to $Man_8$ DID3 and $Man_9$ with Nanomolar Affinity: Implications for Binding to the HIV Envelope Protein gp120", J. Am. Chem. Soc., 2001, vol. 123, pp. 3892-3902.

Bewley et al., "Solution structure of cyanovirin-N, a potent HIV-inactivating protein", Nature Structural Biology, Jul. 1998, vol. 5, No. 7, pp. 571-578.

Binley et al., "Comprehensive Cross-Clade Neutralization Analysis of a Panel of Anti-Human Immunodeficiency Virus Type 1 Monoclonal Antibodies", Journal of Virology, Dec. 2004, vol. 78, No. 23, pp. 13232-13252.

Bitonti et al., "Pulmonary delivery of an erythropoietin Fc fusion protein in non-human primates through an immunoglobulin transport pathway", PNAS, Jun. 29, 2004, vol. 101, No. 26, pp. 9763-9768.

Bolmstedt et al., "Cyanovirin-N Defines a New Class of Antiviral Agent Targeting N-Linked, High-Mannose Glycans in an Oligosaccharide-Specific Manner", Molecular Pharmacology, 2001, vol. 59, No. 5, pp. 949-954.

Botos et al., "Domain-swapped structure of a mutant of cyanovirin-N", Biochemical and Biophysical Research Communications, 2002, vol. 294, pp. 184-190.

Botos et al., "Cyanovirin-N: a sugar-binding antiviral protein with a new twist", CMLS, Cell. Mol. Life Sci., 2003, vol. 60, pp. 277-287.

Botos et al., "Structures of the Complexes of a Potent Anti-HIV Protein Cyanovirin-N and High Mannose Oligosaccharides", The Journal of Biological Chemistry, Sep. 13, 2002, vol. 277, No. 37, pp. 34336-34342.

Boyd et al., "Discovery of Cyanovirin-N, a Novel Human Immunodeficiency Virus-Inactivating Protein That Binds Viral Surface Envelope Glycoprotein gp120: Potential Applications to Microbicide Development", Antimicrobial Agents and Chemotherapy, Jul. 1997, vol. 41, No. 7, pp. 1521-1530.

Bringans et al., "Development of a fluorescent microplate assay for determining cyanovirin-N levels in plasma", Anal Bioanal Chem, 2004, vol. 380, pp. 269-274.

Brunger, "Version 1.2 of the Crystallography and NMR system", Nature Protocols, 2007, vol. 2, No. 11, pp. 2728-2733.

Brünger et al., "*Crystallography & NMR System*: A New Software Suite for Macromolecular Structure Determination", Acta Cryst., 1998, vol. D54, pp. 905-921.

Burton et al., "Efficient Neutralization of Primary Isolates of HIV-1 by a Recombinant Human Monoclonal Antibody", Science, New Series, Nov. 11, 1994, vol. 266, No. 5187, pp. 1024-1027.

Burton et al., "HIV vaccine design and the neutralizing antibody problem", Nature Immunology, Mar. 2004, vol. 5, No. 3, pp. 233-236.

Burton et al., "Antibody vs. HIV in a clash of evolutionary titans", PNAS, Oct. 18, 2005, vol. 102, No. 42, pp. 14943-14948.

Byrn et al., "Biological properties of a CD4 immunoadhesin", Nature, Apr. 12, 1990, vol. 344, pp. 667-670.

Calarese et al., "Antibody Domain Exchange Is an Immunological Solution to Carbohydrate Cluster Recognition", Science, Jun. 27, 2003, vol. 300, pp. 2065-2071.

Capon et al., "Designing CD4 immunoadhesins for AIDS therapy", Nature, Feb. 9, 1989, vol. 337, pp. 525-531.

Cardoso et al., "Broadly Neutralizing Anti-HIV Antibody 4E10 Recognizes a Helical Conformation of a Highly Conserved Fusion-Associated Motif in gp41", Immunity, Feb. 2005, vol. 22, pp. 163-173.

Charnow et al., "Immunoadhesins: principles and applications", Tibtech, Feb. 1996, vol. 14, pp. 52-60.

Cheung et al., "Distribution of Amantadine-Resistant H5N1 Avian Influenza Variants in Asia", JID, Jun. 15, 2006, vol. 193, pp. 1626-1629.

Collaborative Computational Project, No. 4, "The *CCP4* Suite: Programs for Protein Crystallography", Acta Cryst., 1994, vol. D50, pp. 760-763.

Colleluori et al., "Expression, purification, and characterization of recombinant cyanovirin-N for vaginal anti-HIV microbicide development", Protein Expression and Purification, 2005, vol. 39, pp. 229-236.

Dacheux et al., "Evolutionary Dynamics of the Glycan Shield of the Human Immunodeficiency Virus Envelope during Natural Infection and Implications for Exposure of the 2G12 Epitope", Journal of Virology, Nov. 2004, vol. 78, No. 22, pp. 12625-12637.

Daëron, "Fc Receptor Biology", Annu. Rev. Immunol., 1997, vol. 15, pp. 203-234.

De Jong et al., "Oseltamivir Resistance during Treatment of Influenza A (H5N1) Infection", N Engl J Med, Dec. 22, 2005, vol. 353, No. 25, pp. 2667-2672.

Dey et al., "Multiple Antiviral Activities of Cyanovirin-N: Blocking of Human Immunodeficiency Virus Type 1 gp120 Interaction with CD4 and Coreceptor and Inhibition of Diverse Enveloped Viruses", Journal of Virology, May 2000, vol. 74, No. 10, pp. 4562-4569.

Dumont et al., "Delivery of an Erythropoietin-Fc Fusion Protein by Inhalation in Humans through an Immunoglobulin Transport Pathway", Journal of Aerosol Medicine, 2005, vol. 18, No. 3, pp. 294-303.

Dwyer et al., "Expression and Characterization of a DNase I-Fc Fusion Enzyme", The Journal of Biological Chemistry, Apr. 2, 1999, vol. 274, No. 14, pp. 9738-9743.

Emmert, "Treatment of Common Cutaneous Herpes Simplex Virus Infections", The American Academy of Family Physicians, Mar. 15, 2000, pp. 1-9.

Emsley et al., "*Coot*: model-building tools for molecular graphics", Acta Cryst., 2004, vol. D60, pp. 2126-2132.

Endsley et al., "Combining Drug and Immune Therapy: A Potential Solution to Drug Resistance and Challenges of HIV Vaccines?", Current HIV Research, 2008, vol. 6, pp. 401-410.

Enserink, "New Vaccine and Treatment Excite Ebola Researchers", Science, Nov. 14, 2003, vol. 302, pp. 1141-1142.

Mori et al., "Recombinant Production of Cyanovirin-N, a Potent Human Immunodeficiency Virus-Inactivating Protein Derived from a Cultured Cyanobacterium", Protein Expression and Purification, 1998, vol. 12, pp. 151-158.

Mossad, "Influenza update 2007-2008: Vaccine advances, pandemic preparation", Cleveland Clinic Journal of Medicine, Dec. 2007, vol. 74, No. 12, pp. 889-894.

Murshudov et al., "Refinement of Macromolecular Structures by the Maximum-Likelihood Method", Acta Cryst., 1997, vol. D53, pp. 240-255.

Ofek et al., "Structure and Mechanistic Analysis of the Anti-Human Immunodeficiency Virus Type 1 Antibody 2F5 in Complex with Its gp41 Epitope", Journal of Virology, Oct. 2004, vol. 78, No. 19, pp. 10724-10737.

O'Keefe et al., "Analysis of the Interaction between the HIV-Inactivating Protein Cyanovirin-N and Soluble Forms of the Envelope Glycoproteins gp120 and gp41", Mol Pharmacol, 2000, vol. 58, No. 5, pp. 982-992.

O'Keefe et al., "Potent Anti-Influenza Activity of Cyanovirin-N and Interactions with Viral Hemagglutinin", Antimicrobial Agents and Chemotherapy, Aug. 2003, vol. 47, No. 8, pp. 2518-2525.

Ong et al., "A Global Perspective on Avian Influenza", Ann Acad Med Singapore, Jun. 2008, vol. 37, No. 6, pp. 477-481.

Presta, "Molecular engineering and design of therapeutic antibodies", Immunology, 2008, vol. 20, pp. 460-470.

Presta, "Selection, design, and engineering of therapeutic antibodies", J Allergy Clin Immunol, Oct. 2005, vol. 116, pp. 731-736.

(56) References Cited

OTHER PUBLICATIONS

Proença-Módena, "H5N1 Avian Influenza Virus: An Overview", The Brazilian Journal of Infectious Diseases, 2007, vol. 11, No. 1, pp. 125-133.
Raghavan et al. "Fc Receptors and Their Interactions with Immunoglobulins", Annu. Rev. Cell Dev. Biol., 1996, vol. 12, pp. 181-220.
Reid et al., "The origin of the 1918 pandemic influenza virus: a continuing enigma", Journal of General Virology, 2003, vol. 84, pp. 2285-2292.
Reitter et al., "A role for carbohydrates in immune evasion in AIDS", Nature Medicine, Jun. 1998, vol. 4, No. 6, pp. 679-684.
Saphire et al., "Crystal Structure of a Neutralizing Human IgG Against HIV-1: A Template for Vaccine Design", Science, Aug. 10, 2001, vol. 293, pp. 1155-1159.
Sattentau et al., "Conformational Changes Induced in the Human Immunodeficiency Virus Envelope Glycoprotein by Soluble CD4 Binding", J. Exp. Med., Aug. 1991, vol. 174, pp. 407-415.
Shafer et al., "HIV-1 Drug Resistance Mutations: an Updated Framework for the Second Decade of HAART", AIDS, Rev. 2008, vol. 10, pp. 67-84.
Shapiro et al., "Expression of Sonic hedgehog-Fc fusion protein in *Pichia pastoris* identification and control of post-translational, chemical, and proteolytic modifications", Protein Expression and Purification, 2003, vol. 29, pp. 272-283.
Shenoy et al., "Multisite and Multivalent Binding between Cyanovirin-N and Branched Oligomannosides: Calorimetric and NMR Characterization", Chemistry & Biology, Oct. 2002, vol. 9, pp. 1109-1118.
Shenoy et al., "Selective Interactions of the Human Immunodeficiency Virus-Inactivating Protein Cyanovirin-N with High-Mannose Oligosaccharides on gp120 and Other Glycoproteins", The Journal of Pharmacology and Experimental Therapeutics, 2001, vol. 297, No. 2, pp. 704-710.
Shields et al., "High Resolution Mapping of the Binding Site on Human IgG1 for FcγRI, FcγRII, FcγRIII, and FcRn and Design of IgG1 Variants with Improved Binding to The FcγR", The Journal of Biological Chemistry, Mar. 2, 2001, vol. 276, No. 9, pp. 6591-6604.
Shields et al., "Lack of Fucose on Human IgG1 *N*-Linked Oligosaccharide Improves Binding to Human FcγRIII and Antibody-dependent Cellular Toxicity", The Journal of Biological Chemistry, Jul. 26, 2002, vol. 277, No. 30, pp. 26733-26740.
Shinkawa et al., "The Absence of Fucose but Not the Presence of Galactose or Bisecting *N*-Acetylglucosamine of Human IgG1 Complex-type Oligosaccharides Shows the Critical Role of Enhancing Antibody-dependent Cellular Cytotoxicity", The Journal of Biological Chemistry, Jan. 31, 2003, vol. 278, No. 5, pp. 3466-3473.
Sjölander et al., "N-Linked Glycans in the CD4-Binding Domain of Human Immunodeficiency Virus Type 1 Envelope Glycoprotein gp160 Are Essential for the in Vivo Priming of T Cells Recognizing an Epitope Located in Their Vicinity", Virology, 1996, vol. 215, pp. 124-133.
Smee et al., "Influenza A (H1N1) virus resistance to cyanovirin-N arises naturally during adaptation to mice and by passage in cell culture in the presence of the inhibitor", Antiviral Chemistry & Chemotherapy, Dec. 10, 2007, vol. 18, pp. 317-327.
Smee et al., "Treatment of influenza A (H1N1) virus infections in mice and ferrets with cyanovirin-N", Antiviral Research, 2008, vol. 80, pp. 266-271.
Stabila et al., "Cell surface expression of a human IgG Fc chimera activates macrophages through Fc receptors", Nature Biotechnology, Dec. 1998, vol. 16, pp. 1357-1360.
Stemmer et al., "Single-step assembly of a gene and entire plasmid from large numbers of oligodeoxyribonucleotides", Gene, 1995, vol. 164, pp. 49-53.
Sugrue, "Viruses and Glycosylation", Methods in Molecular Biology, Glycovirology Protocols, pp. 1-13.
Sugrue et al., "Antiviral Drugs for the Control of Pandemic Influenza Virus", Ann Acad Med Singapore, 2008, vol. 37, pp. 518-524.
Tosh et al., "Flu Myths: Dispelling the Myths Associated With Live Attenuated Influenza Vaccine", Mayo Clin Proc., Jan. 2008, vol. 83, No. 1, pp. 77-84.
Traggiai et al., "Development of a Human Adaptive Immune System in Cord Blood Cell-Transplanted Mice", Science, Apr. 2, 2004, vol. 304, pp. 104-107.
Trkola et al., "Cross-Clade Neutralization of Primary Isolates of Human Immunodeficiency Virus Type 1 by Human Monoclonal Antibodies and Tetrameric CD4-IgG", Journal of Virology, Nov. 1995, vol. 69, No. 11, pp. 6609-6617.
Trkola et al., "Human Monoclonal Antibody 2G12 Defines a Distinctive Neutralization Epitope on the gp120 Glycoprotein of Human Immunodeficiency Virus Type 1", Journal of Virology, Feb. 1996, vol. 70, No. 2, pp. 1100-1108.
Tsai et al., "Cyanovirin-N Gel as a Topical Microbicide Prevents Rectal Transmission of SHIV89.6P in Macaques", AIDS Research and Human Retroviruses, 2003, vol. 19, No. 7, pp. 535-541.
Tsai et al., "Cyanovirin-N Inhibits AIDS Virus Infections in Vaginal Transmission Models", AIDS Research and Human Retroviruses, 2004, vol. 20, No. 1, pp. 11-18.
Vigerust et al., "Virus glycosylation: role in virulence and immune interactions", Trends in Microbiology, 2007, vol. 15, No. 5, pp. 211-218.
Von Itzstein, "Avian influenza virus, a very sticky situation", Chemical Biology, 2008, vol. 12, pp. 102-108.
Webby et al., "Are We Ready for Pandemic Influenza?", Science, Nov. 28, 2003, vol. 302, pp. 1519-1522.
Wei et al., "Antibody neutralization and escape by HIV-1", Nature, Mar. 20, 2003, vol. 422, pp. 307-312.
Weingarten et al., "Barriers to influenza vaccine acceptance a survey of physicians and nurses", Am J Infect Control, Aug. 1989, vol. 17, No. 4, pp. 202-207.
Weis et al., "The C-type lectin superfamily in the immune system", Immunological Reviews, 1998, vol. 163, pp. 19-34.
West, Jr. et al., "Design and Expression of a Dimeric Form of Human Immunodeficiency Virus Type 1 Antibody 2G12 with Increased Neutralization Potency", Journal of Virology, Jan. 2009, vol. 83, No. 1, pp. 98-104.
Witvrouw et al., "Resistance of Human Immunodeficiency Virus Type 1 to the High-Mannose Binding Agents Cyanovirin N and Concanavalin A", Journal of Virology, Jun. 2005, vol. 79, No. 12, pp. 7777-7784.
Wolbank et al., "Characterization of Human Class-Switched Polymeric (Immunoglobulin M [IgM] and IgA) Anti-Human Immunodeficiency Virus Type 1 Antibodies 2F5 and 2G12", Journal of Virology, Apr. 2003, vol. 77, No. 7, pp. 4095-4103.
Yang et al., "Crystal Structure of Cyanovirin-N, a Potent HIV-inactivating Protein, Shows Unexpected Domain Swapping", J. Mol. Biol., 1999, vol. 288, pp. 403-412.
Zappe et al., "PEGylation of cyanovirin-N, an entry inhibitor of HIV", Advanced Drug Delivery Reviews, 2008, vol. 60, pp. 79-87.
Zhang et al., "HIV-1 infection and pathogenesis in a novel humanized mouse model", Blood, Apr. 1, 2007, vol. 109, No. 7, pp. 2978-2981.
Zhou et al., "Structural definition of a conserved neutralization epitope on HIV-1 gp120", Nature, Feb. 15, 2007, vol. 445, pp. 732-737.
Zhu et al., "Distribution and three-dimensional structure of AIDS virus envelope spikes", Nature, Jun. 15, 2006, vol. 441, pp. 847-852.
Esser et al., "Cyanovirin-N Binds to gp120 to Interfere with CD4-Dependent Human Immunodeficiency Virus Type 1 Virion Binding, Fusion, and Infectivity but Does Not Affect the CD4 Binding Site on gp120 or Soluble CD4-Induced Conformational Changes in gp120", Journal of Virology, May 1999, vol. 73, No. 5, pp. 4360-4371.
Fenouillet et al., "Role of N-Linked Glycans of Envelope Glycoproteins in Infectivity of Human Immunodeficiency Virus Type 1", Journal of Virology, Jun. 1990, vol. 64, No. 6, pp. 2841-2848.
Florese et al., "Evaluation of Passively Transferred, Nonneutralizing Antibody-Dependent Cellular Cytotoxicity-Mediating IgG in Protection of Neonatal Rhesus Macaques against Oral SIV$_{mac251}$ Challenge", The Journal of Immunology, 2006, vol. 177, pp. 4028-4036.
Fromme et al., "A Monovalent Mutant of Cyanovirin-N Provides Insight into the Role of Multiple Interactions with gp120 for Antiviral Activity", Biochemistry, 2007, vol. 46, pp. 9199-9207.

(56) References Cited

OTHER PUBLICATIONS

Fromme et al., "Conformational gating of dimannose binding to the antiviral protein cyanovirin revealed from the crystal structure at 1.35 Å resolution", Protein Science, 2008, vol. 17, pp. 939-944.

Gessner et al., "The IgG Fc receptor family", Ann Hematol, 1998, vol. 76, pp. 231-248.

Gómez-Román et al., "Vaccine-Elicited Antibodies Mediate Antibody-Dependent Cellular Cytotoxicity Correlated with Significantly Reduced Acute Viremia in Rhesus Macaques Challenged with $SIV_{mac251}$ [1]", The Journal of Immunology, 2005, vol. 174, pp. 2185-2189.

Gupta et al., "Targeted lysis of HIV-infected cells by natural killer cells armed and triggered by a recombinant immunoglobulin fusion protein: implications for immunotherapy", Virology, 2005, vol. 332, pp. 491-497.

Gurbaxani et al., "Development of new models for the analysis of Fc-FcRn interactions", Molecular Immunology, 2006, vol. 43, pp. 1379-1389.

He et al., "Amantadine-resistance among H5N1 avian influenza viruses isolated in Northern China", Antiviral Research, 2008, vol. 77, pp. 72-76.

Hedestam et al., "The challenges of eliciting neutralizing antibodies to HIV-1 and to influenza virus", Microbiology, Feb. 2008, vol. 6, pp. 143-155.

Helle et al., "Cyanovirin-N Inhibits Hepatitis C Virus Entry by Binding to Envelope Protein Glycans", The Journal of Biological Chemistry, Sep. 1, 2006, vol. 281, No. 35, pp. 25177-25183.

Hessell et al., "Fc receptor but not complement binding is important in antibody protection against HIV", Nature, Sep. 6, 2007, vol. 449, pp. 101-105.

Hinton et al., "Engineered Human IgG Antibodies with Longer Serum Half-lives in Primates", The Journal of Biological Chemistry, Feb. 20, 2004, vol. 279, No. 8, pp. 6213-6216.

Hinton et al., "An Engineered Human IgG1 Antibody with Longer Serum Half-Life", The Journal of Immunology, 2006, vol. 176, pp. 346-356.

Holl et al., "Nonneutralizing Antibodies Are Able to Inhibit Human Immunodeficiency Virus Type 1 Replication in Macrophages and Immature Dendritic Cells", Journal of Virology, Jun. 2006, vol. 80, No. 12, pp. 6177-6181.

Holl et al., "Efficient inhibition of HIV-1 replication in human immature monocyte-derived dendritic cells by purified anti-HIV-1 IgG without induction of maturation", Blood, Jun. 1, 2006, vol. 107, No. 11, pp. 4466-4474.

Hu et al., "High-mannose-specific deglycosylation of HIV-1 gp120 induced by resistance to cyanovirin-N and the impact on antibody neutralization", Virology, 2007, vol. 368, pp. 145-154.

"Report on the global AIDS epidemic", Joint United Nations Programme on HIV/AIDS (UNAIDS), 2008, pp. 1-362.

Huber et al., "Humoral immunity to HIV-1: neutralization and beyond", J Intern Med, 2007, vol. 262, pp. 5-25.

Huber et al., "Fc Receptor-Mediated Phagocytosis Makes a Significant Contribution to Clearance of Influenza Virus Infections", The Journal of Immunology, 2001, vol. 166, pp. 7381-7388.

Idusogie et al., "Engineered Antibodies with Increased Activity to Recruit Complement", The Journal of Immunology, 2001, vol. 166, pp. 2571-2575.

Imperial! et al., "Effect of N-linked glycosylation on glycopeptide and glycoprotein structure", Chemical Biology, 1999, vol. 3, pp. 643-649.

Jazayeri et al., "Fc-Based Cytokines", Biodrugs, 2008, vol. 22, No. 1, pp. 11-26.

Jefferis et al., "IgG-Fc-mediated effector functions: molecular definition of interaction sites for effector ligands and the role of glycosylation", Immunological Reviews, 1998, vol. 163, pp. 59-76.

Kang et al., "Modified HIV envelope proteins with enhanced binding to neutralizing monoclonal antibodies", Virology, 2005, vol. 331, pp. 20-32.

Kelley et al., "Engineering an Obligate Domain-Swapped Dimer of Cyanovirin-N with Enhanced Anti-HIV Activity", J. Am. Chem. Soc., 2002, vol. 124, pp. 3210-3211.

Krug, "The potential use of influenza virus as an agent for bioterrorism", Antiviral Research, 2003, vol. 57, pp. 147-150.

Kwong et al., "Structure of an HIV gp120 envelope glycoprotein in complex with the CD4 receptor and a neutralizing human antibody", Nature, Jun. 18, 1998, vol. 393, pp. 648-659.

Labrijn et al., "Access of Antibody Molecules to the Conserved Coreceptor Binding Site on Glycoprotein gp120 Is Sterically Restricted on Primary Human Immunodeficiency Virus Type 1", Journal of Virology, Oct. 2003, vol. 77, No. 19, pp. 10557-10565.

Langner et al., "Antiviral effects of different CD4-immunoglobulin constructs against HIV-1 and SIV: immunological characterization, pharmacokinetic data and in vivo experiments", Arch Virol, 1993, vol. 130, pp. 157-170.

Lazar et al., "Engineered antibody Fc variants with enhanced effector function", PNAS, Mar. 14, 2006, vol. 103, No. 11, pp. 4005-4010.

Le et al., "Isolation of drug-resistant H5N1 virus", Nature, Oct. 20, 2005, vol. 437, 1 pg.

Legrand et al., "Experimental Models to Study Development and Function of the Human Immune System In Vivo", The Journal of Immunology, 2006, vol. 176, pp. 2053-2058.

Leonard et al., "Assignment of Intrachain Disulfide Bonds and Characterization of Potential Glycosylation Sites of the Type 1 Recombinant Human Immunodeficiency Virus Envelope Glycoprotein (gp120) Expressed in Chinese Hamster Ovary Cells", The Journal of Biological Chemistry, Jun. 25, 1990, vol. 265, No. 18, pp. 10373-10382.

Li et al., "Genetic and Neutralization Properties of Subtype C Human Immunodeficiency Virus Type 1 Molecular *env* Clones from Acute and Early Heterosexually Acquired Infections in Southern Africa", Journal of Virology, Dec. 2006, vol. 80, No. 23, pp. 11776-11790.

Li et al., "Glycosylation Is Necessary for the Correct Folding of Human Immunodeficiency Virus gp120 in CD4 Binding", Journal of Virology, Jan. 1993, vol. 67, No. 1, pp. 584-588.

Li et al., "Human Immunodeficiency Virus Type 1 *env* Clones from Acute and Early Subtype B Infections for Standardized Assessments of Vaccine-Elicited Neutralizing Antibodies", Journal of Virology, Aug. 2005, vol. 79, No. 16, pp. 10108-10125.

Low et al., "Oral and pulmonary delivery of FSH-Fc fusion proteins via neonatal Fc receptor-mediated transcytosis", Human Reproduction, 2005, vol. 20, No. 7, pp. 1805-1813.

Malenbaum et al., "The N-Terminal V3 Loop Glycan Modulates the Interaction of Clade A and B Human Immunodeficiency Virus Type 1 Envelopes with CD4 and Chemokine Receptors", Journal of Virology, Dec. 2000, vol. 74, No. 23, pp. 11008-11016.

Mariner et al., "The HIV-Inactivating Protein, Cyanovirin-N, Does Not Block gp120-Mediated Virus-to-Cell Binding", Biochemical and Biophysical Research Communications, 1998, vol. 248, pp. 841-845.

Matei et al., "Solution and Crystal Structures of a Sugar Binding Site Mutant of Cyanovirin-N: No Evidence of Domain Swapping", Structure, Aug. 6, 2008, vol. 16, pp. 1183-1194.

McCoy et al., "Likelihood-enhanced fast translation functions", Acta Cryst., 2005, vol. D61, pp. 458-464.

McFadden et al., "A Recombinant Allosteric Lectin Antagonist of HIV-1 Envelope gp120 Interactions", Proteins: Structure, Function, and Bioinformatics, 2007, vol. 67, pp. 617-629.

Montefiori et al., "Role of protein N-glycosylation in pathogenesis of human immunodeficiency virus type 1", Proc. Natl. Acad. Sci. USA, Dec. 1998, vol. 85, pp. 9248-9252.

Mori et al., "Analysis of Sequence Requirements for Biological Activity of Cyanovirin-N, a Potent HIV (Human Immunodeficiency Virus)-Inactivating Protein", Biochemical and Biophysical Research Communications, 1997, vol. 238, pp. 218-222.

Mori et al., "Construction and Enhanced Cytotoxicity of a [Cyanovirin-N]-[*Pseudomonas* Exotoxin] Conjugate against Human Immunodeficiency Virus-Infected Cells", Biochemical and Biophysical Research Communications, 1997, vol. 239, pp. 884-888.

Mori et al., "Cyanovirin-N, a Potent Human Immunodeficiency Virus-Inactivating Protein, Blocks both CD4-Dependent and CD4-Independent Binding of Soluble gp120 (sgp120) to Target Cells,

(56) References Cited

OTHER PUBLICATIONS

Inhibits sCD4-Induced Binding of sgp120 to Cell-Associated CXCR4, and Dissociates Bound sgp120 from Target Cells", Antimicrobial Agents and Chemotherapy, Mar. 2001, vol. 45, No. 3, pp. 664-672.
Mori et al., "Functional homologs of cyanovirin-N amenable to mass production in prokaryotic and eukaryotic hosts", Protein Expression and Purification, 2002, vol. 26, pp. 42-49.
Keeffe et al., "Designed oligomers of cyanovirin-N show enhanced HIV neutralization", PNAS, Aug. 23, 2011, vol. 108, No. 34, pp. 14079-14084.
Michelow et al., "A Novel L-ficolin/Mannose-binding Lectin Chimeric Molecule with Enhanced Activity against Ebola Virus", The Journal of Biological Chemistry, Aug. 6, 2010, vol. 285, No. 32, pp. 24729-24739.
Nishi et al., "Development of highly stable galectins: Truncation of the linker peptide confers protease-resistance on tandem-repeat type galectins", FEBS Letters, 2005, vol. 579, pp. 2058-2064.
Aldaye et al., "Assembling Materials with DNA as the Guide", Science, Sep. 26, 2008, vol. 321, pp. 1795-1799.
Andersen et al., "Self-Assembly of a Nanoscale DNA Box With a Controllable Lid", Nature, May 7, 2009, vol. 459, pp. 73-77.
Bartel, "MicroRNAs: Target Recognition and Regulatory Functions", Cell, Jan. 23, 2009, vol. 136, pp. 215-233.
Bath et al., "DNA Nanomachines", Nature Nanotechnology, May 2007, vol. 2, pp. 275-284.
Bunka et al., "Aptamers Come of Age—At Last", Nature, Aug. 2006, vol. 4, pp. 588-596.
Carlson, "The Changing Economics of DNA Synthesis", Nature Biotechnology, Dec. 2009, vol. 27, No. 12, pp. 1091-1094.
Ding et al., "Operation of a DNA Robot Arm Inserted into a 2D DNA Crystalline Substrate", Science, Dec. 8, 2006, vol. 314, pp. 1583-1585.
Dirks et al., "Triggered Amplification by Hybridization Chain Reaction", PNAS, Oct. 26, 2004, vol. 101, No. 43, pp. 15275-15278.
Douglas et al., "Self-Assembly of DNA Into Nanoscale Three-Dimensional Shapes", Nature, May 21, 2009, vol. 459, pp. 414-418, 1154.
Frezza et al., "Modular Multi-Level Circuits from Immobilized DNA-Based Logic Gates", J. Am. Chem. Soc, 2007, vol. 129, pp. 14875-14879.
Gao et al., "Secondary Structure Effects on DNA Hybridization Kinetics: A Solution Versus Surface Comparison", Nucleic Acids Research, Jul. 5, 2006, vol. 34, No. 11, pp. 3370-3377.
Gartner et al., "DNA-Templated Organic Synthesis and Selection of a Library of Macrocycles", Science, Sep. 10, 2004, vol. 305, pp. 1601-1605.
Green et al., "Coordinated Chemomechanical Cycles: A Mechanism for Autonomous Molecular Motion", Physical Review Letters, Dec. 3, 2008, vol. 101, No. 238101, pp. 1-4.
Gu et al., "A Proximity-Based Programmable DNA Nanoscale Assembly Line", Nature, May 13, 2010, vol. 465, pp. 202-206.
Hamilton et al., "A Species of Small Antisense RNA in Posttranscriptional Gene Silencing in Plants", Science, Oct. 29, 1999, vol. 286, pp. 950-952.
Isaacs et al., "Engineered Riboregulators Enable Post-Transcriptional Control of Gene Expression", Nature Biotechnology, Jul. 2004, vol. 22, No. 7, pp. 841-847.
Joyce, "Directed Evolution of Nucleic Acid Enzymes", Annu. Rev. Biochem, 2004, vol. 73, pp. 791-836.
Krueger et al., "Redesigning the Architecture of the Base Pair: Toward Biochemical and Biological Function of New Genetic Sets", Chemistry & Biology, Mar. 27, 2009, vol. 16, pp. 242-248.
Lederman et al., "Deoxyribozyme-Based Three-Input Logic Gates and Construction of a Molecular Full Adder", Biochemistry, 2006, vol. 45, No. 4, pp. 1194-1199.
Levy et al., "Exponential Growth by Cross-Catalytic Cleavage of Deoxyribozymogens", PNAS, May 27, 2003, vol. 100, No. 11, pp. 6416-6421.
Lu et al., "Functional DNA Nanotechnology: Emerging Applications of DNAzymes and Aptamers", Current Opinion in Biotechnology, 2006, vol. 17, pp. 580-588.
Lu et al., "MicroRNA Expression Profiles Classify Human Cancers", Nature, Jun. 9, 2005, vol. 435, pp. 834-838.
Lund et al., "Molecular Robots Guided by Prescriptive Landscapes", Nature, May 13, 2010, vol. 465, pp. 206-210.
Mao et al., "A Nanomechanical Device Based on the B-Z Transition of DNA", Nature, Jan. 14, 1999, vol. 397, pp. 144-146.
Marras et al., "Efficiencies of Fluorescence Resonance Energy Transfer and Contact-Mediated Quenching in Oligonucleotide Probes", Nucleic Acids Research, 2002, vol. 30, No. 21, pp. 1-8.
Maune et al., "Self-Assembly of Carbon Nanotubes Into Two-Dimensional Geometries Using DNA Origami Templates", Nature Nanotechnology, Jan. 2010, vol. 5, pp. 61-66.
Omabegho et al., "A Bipedal DNA Brownian Motor with Coordinated Legs", Science, Apr. 3, 2009, vol. 324, pp. 67-71.
Owczarzy et al., "Predicting Stability of DNA Duplexes in Solutions Containing Magnesium and Monovalent Cations", Biochemistry, 2008, vol. 47, pp. 5336-5353.
Pyshnyi et al., "The Influence of Nearest Neighbours on the Efficiency of Coaxial Stacking at Contiguous Stacking Hybridization of Oligodeoxyribonucleotides", Nucleosides, Nucleotides & Nucleic Acids, 2004, vol. 23, No. 6 & 7, pp. 1057-1064.
Rinker et al., "Self-Assembled DNA Nanostructures for Distance-Dependent Multivalent Ligand—Protein Binding", Nature Nanotechnology, Jul. 2008, vol. 3, pp. 418-422.
Rosi et al., "Nanostructures in Biodiagnostics", Chemical Reviews, 2005, vol. 105, No. 4, pp. 1547-1562.
Rothemund, "Folding DNA to Create Nanoscale Shapes and Patterns", Nature, Mar. 16, 2006, vol. 440, pp. 297-302.
Rothemund et al., "Algorithmic Self-Assembly of DNA Sierpinski Triangles", PLOS Biology, Dec. 2004, vol. 2, No. 12, pp. 2041-2053.
Santalucia et al., "The Thermodynamics of DNA Structural Motifs", Annual Review of Biophysics and Biomolecular Structure 2004, vol. 33, pp. 415-440, C1, C-2.
Seelig et al., "Catalyzed Relaxation of a Metastable DNA Fuel", J. Am. Chemical Society, 2006, vol. 128, pp. 12211-12220.
Seelig et al., "Enzyme-Free Nucleic Acid Logic Circuits", Science, Dec. 8, 2006, vol. 314, pp. 1585-1588.
Seferos et al., "Nano-Flares: Probes for Transfection and mRNA Detection in Living Cells", J. American Chemical Society, 2007, vol. 129, pp. 15477-15479.
Shih et al., "Knitting Complex Weaves With DNA Origami", Current Opinion in Structural Biology, 2010, vol. 20, pp. 276-282.
Soloveichik et al., "DNA as a Universal Substrate for Chemical Kinetics", PNAS, Mar. 23, 2010, vol. 107, No. 12, pp. 5393-5398.
Stojanovic et al., "A Deoxyribozyme-Based Molecular Automaton", Nature Biotechnology, Sep. 2003, vol. 21, No. 9, pp. 1069-1074.
Tyagi et al., "Molecular Beacons: Probes that Fluoresce Upon Hybridization", Nature Biotechnology, Mar. 1996, vol. 14, pp. 303-308.
Venkataraman et al., "An Autonomous Polymerization Motor Powered by DNA Hybridization", Nature Nanotechnology, Aug. 2007, vol. 2, pp. 490-494.
Venkataraman et al., "Selective Cell Death Mediated by Small Conditional RNAs", PNAS, Sep. 28, 2010, vol. 107, No. 39, pp. 16777-16782.
Willner et al., "DNAzymes for Sensing, Nanobiotechnology and Logic Gate Applications", Chemical Society Reviews, 2008, vol. 37, pp. 1153-1165.
Win et al., "Higher-Order Cellular Information Processing with Synthetic RNA Devices", Science, Oct. 17, 2008, vol. 322, pp. 456-460.
Winfree et al., "Design and Self-Assembly of Two-Dimensional DNA Crystals", Nature, Aug. 6, 1998, vol. 394, pp. 539-544.
Xie et al., "Logic Integration of mRNA Signals by an RNAi-Based Molecular Computer", Nucleic Acids Research, 2010, vol. 38, No. 8, pp. 2692-2701.
Yan et al., "A Robust DNA Mechanical Device Controlled by Hybridization Topology", Nature, Jan. 3, 2002, vol. 415, pp. 62-65.

(56) References Cited

OTHER PUBLICATIONS

Yin et al., "Programming biomolecular self-assembly pathways", Nature, Jan. 17, 2008, vol. 451, p. 319.

Yurke et al., "A DNA-Fuelled Molecular Machine Made of DNA", Nature, Aug. 10, 2000, vol. 406, pp. 605-608.

Zamore et al., "RNAi: Double-Stranded RNA Directs the ATP-Dependent Cleavage of mRNA at 21 to 23 Nucleotide Intervals", Cell, Mar. 31, 2000, vol. 101, pp. 25-33.

Zhang et al., "Control of DNA Strand Displacement Kinetics Using Toehold Exchange", J. Am. Chem. Soc., 2009, vol. 131, pp. 17303-17314.

Zhang et al., "Dynamic Allosteric Control of Noncovalent DNA Catalysis Reactions", J. Am. Chem. Soc., 2008, vol. 130, pp. 13921-13926.

Zhang et al., "Dynamic DNA Nanotechnology Using Strand-Displacement Reactions", Nature Chemistry, Feb. 2011, vol. 3, pp. 103-113.

Zhang et al., "Engineering Entropy-Driven Reactions and Networks Catalyzed by DNA", Science, Nov. 16, 2007, vol. 318, pp. 1121-1125, 1.

Zheng et al., "From Molecular to Macroscopic via the Rational Design of a Self-Assembled 3D DNA Crystal", Nature, Sep. 3, 2009, vol. 461, pp. 74-77.

\* cited by examiner

ENGINEERED LECTIN OLIGOMERS WITH ANTIVIRAL ACTIVITY

CROSS-REFERENCE TO RELATED APPLICATIONS

The current application claims priority to U.S. Provisional Application No. 61/130,633, filed Jun. 2, 2008, the disclosure of which is incorporated herein by reference.

STATEMENT OF FEDERAL FUNDING

The federal government has rights to the current invention pursuant to funding provided in accordance with grant numbers HR0011-05-1-004 and F49620-03-1-0291, issued by the Defense Advanced Research Projects Agency; and grant number N00244-09-1-0011, issued by the National Security Science and Engineering Faculty Fellowship.

FIELD OF THE INVENTION

The current invention is related to engineered lectins designed to neutralize viruses having glycosylated envelope proteins; and more particularly to lectin oligomers and lectin-antibody hybrids for the treatment or prevention of disease caused by enveloped viruses such as influenza, Ebola, chicken pox, SARS (severe acute respiratory syndrome), small pox, hepatitis C, herpes and HIV.

BACKGROUND OF THE INVENTION

Viruses are subcellular agents that rely on the molecular machinery of a host cell to replicate. They have evolved to infect almost every organism and are increasingly being employed in scientific research. Although viruses contain very small genomes encoding only a few necessary proteins, they have adapted to evade immune systems and transmit efficiently from host to host. (See, e.g., Fields, B. N., et al., *Fields Virology*, 5th edit, 2007; and Strauss, J. H. & Strauss, E. G., *Viruses and Human Disease*, 2nd edit, 2008, the disclosures of which are incorporated herein by reference.)

Viruses come in different shapes, sizes, and types of genomic information, one such sub-type are the "enveloped viruses". Enveloped viruses are a class of viruses that bud from the plasma or internal membrane of plants or animals during their replication. The newly budded viral particle contains the genomic material inside a protein capsid, which in turn is surrounded by membrane from the host and envelope proteins. Envelope proteins are often heavily glycosylated by the host machinery, and therefore are often not immediately recognized by the immune system. These envelope glycoproteins are usually involved in interactions with cellular receptors on target host cells, triggering membrane fusion and infection.

Enveloped viruses cause many well known diseases, including influenza, Ebola, chicken pox, SARS (severe acute respiratory syndrome), small pox, and AIDS. (See, e.g., Fields, et al., cited above.) Human immunodeficiency virus (HIV), the virus that causes AIDS, affects approximately 33 million people throughout the world and causes approximately 2 million HIV-related deaths per year. (See, e.g., UNAIDS, *Report On The Global AIDS Epidemic*, 2008, the disclosure of which is incorporated herein by reference.) While current retroviral therapies have extended the length and quality of life of those infected with HIV, resistant strains are becoming increasingly common, and additional treatments and a broad spectrum vaccine are necessary to prevent additional infections. In turn, although influenza does not typically cause the mortality of HIV, it is a highly contagious virus that can be lethal, usually in the very young and very old, and in those with immune deficiencies. Moreover, influenza pandemics, such as the one in 1918 when an estimated 40 million people worldwide were killed, are capable of causing a significant number of deaths, including in healthy young adults. (See, e.g., Reid, A. H., et al., *J Gen Virol*, 84, 2285-92, 2003, the disclosure of which is incorporated herein by reference.)

Current treatment for viral infection varies widely for different viruses. Effective vaccines are available for smallpox, measles, hepatitis, and varicella-zoster (chicken pox) viruses, among others. However, there are significant limitations to current vaccines. For example, influenza vaccines are typically effective against the strains included in the vaccine, but must be readministered every year due to the rapid mutation rate of the virus. (See, e.g., Mossad, S. B. *Cleve Clin J Med*, 74, 889-94, 2007, the disclosure of which is incorporated herein by reference.) Moreover, for some enveloped viruses there is no vaccine and therefore treatment of the infection is the primary clinical goal. For example, there are currently no vaccines available for Ebola virus, herpes viruses, hanta viruses, HIV, and many other potentially deadly viruses. For many of these diseases, treatment is administered to make the patient more comfortable, provide symptom relief, or decrease the viral load to allow the immune system to more easily fight off the infection. (See, e.g., Enserink, M., *Science*, 302, 1141-2, 2003 and Emmert, D. H., *Am Fam Physician*, 61, 1697-706, 1708, 2000, the disclosures of which are incorporated herein by reference.)

Efforts to develop a vaccine for HIV have met with limited success, with promising laboratory results thus far leading only to failures in clinical trials. (See, e.g., Burton, D. R., et al., *Nat Immunol*, 5, 233-6, 2004; Karlsson Hedestam, G. B., et al., *Nat Rev Microbiol*, 6, 143-55, 2008; Endsley, A. N., et al., *Curr HIV Res*, 6, 401-10, 2008; Burton, D. R., et al., *Proc Natl Acad Sci USA*, 102, 14943-8, 2005; Cardoso, R. M., et al., *Immunity*, 22, 163-73, 2005; Trkola, A., et al., *J Virol*, 70, 1100-8, 1996; and Burton, D. R., et al., *Science*, 266, 1024-7, 1994, the disclosures of each of which are incorporated herein by reference.)

While research continues on developing an effective and cross-reactive vaccine, patients currently rely on antiviral drugs to decrease their viral load and prolong their lives. HIV antiviral therapy usually consists of three or more antiretroviral drugs from at least two inhibitory classes in a therapeutic regimen known as highly active antiretroviral therapy (HAART). (See, e.g., Endsley, A. N., et al., 2008, cited above.) As of 2008, 32 antivirals have been approved by the FDA for treatment of HIV-1 infections. Although HAART has been quite successful at reducing the viral load of patients, the rapid mutation rate of HIV often eventually leads to drug resistant strains, rendering antiviral treatment ineffective. (See, e.g., Shafer, R. W. & Schapiro, J. M., *AIDS Rev* 10, 67-84, 2008, the disclosure of which is incorporate herein by reference.)

Unlike for HIV, there is a very effective vaccine for influenza. However, the inconvenience and cost of yearly immunization, as well as the unpredictable mutation of influenza, means that millions of people are susceptible to infection every year. (See, e.g., Tosh, P. K., et al., *Mayo Clin Proc*, 83, 77-84, 2008; and Weingarten, S., et al., *Am J Infect Control*, 17, 202-7, 1989.) In addition, the recent emergence of a highly lethal H5N1 strain ("bird flu"), and concerns over the recent outbreak of H1N1 ("swine flu"), has led to concerns that these strains could become easily transmittable from human to human or weaponized, creating a massive influenza pandemic. (See, e.g., Webby, R. J. & Webster, R. G., *Science*, 302, 1519-22, 2003; von Itzstein, M., *Curr Opin Chem Biol*, 12, 102-8, 2008; Ong, A., et al., *Ann Acad Med Singapore*, 37, 477-81, 2008; and Krug, R. M. *Antiviral Res*, 57, 147-50, 2003, the disclosures of each of which are incorporated herein by reference.) Although Influenza A, including H5N1 strains, can be treated with antiviral medications, including oseltamivir (Tamiflu) and zanamivir (Relenza), resistance to oseltamivir and other common influenza antivirals have already been reported in H5N1 cases. (See, e.g., Sugrue, R. J., et al., *Ann Acad Med Singapore*, 37, 518-24, 2008; Proenca-Modena, J. L., et al., *Braz J Infect Dis*, 11, 125-33; de Jong, M. D., et al., *N Engl J Med*, 353, 2667-72, 2005; Le, Q. M., et al., *Nature*, 437, 1108, 2005; He, G., et al., *Antiviral Res*, 77, 72-6, 2008; and Cheung, C. L., et al., *Infect Dis*, 193, 1626-9, 2006, the disclosures of each of which are incorporated herein by reference.)

As described above, traditional approaches for preventing and treating viral infection largely rely on vaccination and small molecule anti-viral drug treatment, respectively. Whether induced by vaccination, natural infection, or directly injected, antibodies that leverage the natural host immune system provide a powerful countermeasure to viral infection. Unfortunately, by its very nature the immune system relies on highly specific interactions with the antigen, which can be defeated by escape mutations that either arise naturally in the viral population or that are engineered. Similarly, escape mutations can render ineffective the beneficial action of antiviral medications.

However, enveloped viruses by their nature contain structures that may provide a new therapeutic target. Specifically, enveloped viruses commonly contain glycosylated envelope proteins that can function in host cell recognition as well as in host immune system evasion by protecting otherwise antigenic protein sites via glycosylation. It has been recently recognized that reagents (such as lectins), that target the carbohydrate portion of glycoproteins, have the potential to neutralize viral infection by blocking binding interactions required for target cell recognition. (See, e.g., Balzarini, J., *Nature Reviews Microbiology*, 5: 583-597, 2007, the disclosure of which is incorporated herein by reference.) Importantly, such reagents have the potential to drive viral evolution toward lower glycosylation levels, which could expose hidden antigenic regions that will then be subject to antibody-based immune action. (See, Smee D. F., et al., *Antivirial Chemistry and Chemotherapy*, 18: 317-327, 2008, the disclosure of which is incorporated herein by reference.) However, to date no therapeutically successful agents targeted at the envelope regions of these viruses have been developed.

In summary, although treatment options of variable effectiveness are available for many envelope type viruses, a need exists for new and improved small molecule and protein-based therapeutics that limit the development of drug resistant strains. Such therapeutics, along with the creation of effective vaccines, will greatly improve the outlook for currently infected patients as well as being beneficial in the case of a pandemic, especially for medical personnel and first-line defenders.

SUMMARY OF THE INVENTION

The current invention is directed to novel therapeutic agents comprising engineered lectins that are designed to bind to and neutralize a broad range of viruses containing glycosylated envelope proteins.

In one embodiment, the invention is directed to a neutralization agent for enveloped viruses having at least two lectins (dimers, trimers, etc.) covalently linked at their termini to form a lectin oligomer. The lectins in such dimers and trimers may be the same or different and may be chosen from the following lectin species, including cyanovirin-N lectin (CVN), griffithsin (GRFT), scytovirin, actinohivin, defensins (such as RC2 and HNPs), *Microcystis viridis* lectin (MVL), *Oscillatoria agardhii* agglutinin, Hippeastrum hybrid agglutinin (HHA), mannose-binding lectin (MBL), and *Urtica dioica* agglutinin (UDA). In one such embodiment, the lectin oligomer is designed to be operative to bind to at least one carbohydrate site on a glycosylated envelope protein of a target virus.

In another embodiment, the lectin oligomers of the current invention are covalently linked through a flexible polypeptide linker. In one such embodiment, the flexible polypeptide linker may comprise anywhere between 1 and 20 amino acids.

In still another embodiment, the oligomerization of the at least two lectins stabilizes the lectin oligomer in an intramolecularly domain-swapped form.

In yet another embodiment, the at least two lectins are cyanovirin-N lectins.

In still yet another embodiment, the target virus is HIV and the oligomer shows cross-clade and cross-strain reactivity. In one such embodiment, the oligomer binds to the gp120 glycoprotein of the HIV virus envelope.

In still yet another embodiment, the invention is directed to a lectibody viral neutralization agent comprising a chimera containing a lectin and the Fc region of an antibody. In one such embodiment the lectin is stabilized in a monomeric state. In another such embodiment, the lectibody is an oligomer containing at least two repeat chimeras. In such an embodiment, the at least two repeat chimeras are covalently linked through a flexible polypeptide linker and the flexible polypeptide linker may contain between 1 and 20 amino acids.

In still yet another embodiment, the target virus is at least one virus selected from the group consisting of HIV, influenza, the pox viruses, the Hanta viruses, hepatitis C, herpes, SARS, and hemorrhagic fever viruses including but not limited to Ebola.

In still yet another embodiment, the lectin portion of the chimera is a cyanovirin-N lectin. In one such embodiment the chimera is a cyanovirin-N-Fc having N30S and P51G mutations.

In still yet another embodiment, the lectibody demonstrates at least one Fc-mediated effector function. In one such embodiment, the at least one Fc-mediated effector function is selected from the group consisting of antibody-dependent cell-mediated cytotoxicity (ADCC), increased half-life, and complement-dependent cytotoxicity (CDC).

In still yet another embodiment, the Fc portion of the chimera binds to the neonatal Fc receptor such that the lectibody is capable of transcytosis.

In still yet another embodiment, the invention is directed to methods of treating a patient diagnosed with an enveloped viral infection and preventing the infection of a patient by an enveloped virus by administering a therapeutically effective amount of a lectin oligomer.

In still yet another embodiment, the invention is directed to methods of treating a patient diagnosed with an enveloped virus infection and preventing the infection of a patient by an enveloped virus by administering a therapeutically effective amount of a lectibody itself comprising a chimera containing a lectin and the Fc region of an antibody.

BRIEF DESCRIPTION OF THE DRAWINGS

The description will be more fully understood with reference to the following figures and data graphs, which are presented as exemplary embodiments of the invention and should not be construed as a complete recitation of the scope of the invention.

FIG. 5 provides WT CVN cross-clade reactivity data compared to broadly HIV neutralizing antibodies. WT CVN effectively neutralized all of the HIV pseudoviruses from clades A, B, and C. The 2G12 HIV neutralizing antibody neutralized some lade A and clade B viruses, but is not effective against any lade C viruses. The 2F5 neutralizing antibody works against only a few lade C envelopes and the IgG1B12 antibody is not fully effective against lade A envelopes. 4E10 is the only HIV neutralizing antibody with comparative cross-clade reactivity to WT CVN, neutralizing all viruses tested.

FIG. 6 provides relative efficacy against HIV strains as compared to broadly neutralizing anti-HIV antibodies. Engineered $CVN_2$ variants neutralize most HIV pseudoviruses with a lower $IC_{50}$ compared to the most effective broadly neutralizing antibody (NAb). For each envelope, the neutralizing antibody with the lowest $IC_{50}$ was chosen for comparison (see Table 2). CVN, $CVN_2$ L0, and CVN2 L10 were evaluated against this "best Nab" from each envelope. CVN $IC_{50}$s that were lower than the NAb $IC_{50}$ are labeled ("Fold lower than WT"). For variants with higher $IC_{50}$s than the NAb, the "Fold worse than best NAb" is the negative inverse of "Fold lower than WT" to provide clarity in the plot. Variants that have $IC_{50}$s lower than the best NAb are shown with positive bars and those with $IC_{50}$s higher than the best NAb are shown with negative bars. (A) Clade A envelopes. (B) Clade B envelopes. (C) Clade C envelopes.

FIG. 7 provides data showing evidence that engineered CVN variants are more effective at neutralizing various HIV strains than WT CVN. For every virus tested, $CVN_2$ L10 neutralized with a lower $IC_{50}$ than WT CVN. For all viruses except one (a clade C envelope), CVN2 L0 neutralized with a lower $IC_{50}$ that $CVN_2$ L10. $CVN_2$ L0 was up to 35-fold better at neutralizing HIV as compared to WT. $CVN_2$ L10 was at most 15-fold better neutralizing than WT.

FIG. 8 provides cellular toxicity assay data for CVN and $CVN_2$s. An XTT-based assay was used to determine whether CVN and $CVN_2$ variants are toxic to Tzm-Bl cells in culture. The CVNs are not toxic at the concentrations used in the HIV neutralization assay (up to 200 nM), but some toxicity was observed at higher concentrations.

DETAILED DESCRIPTION OF THE INVENTION

Figure 1:
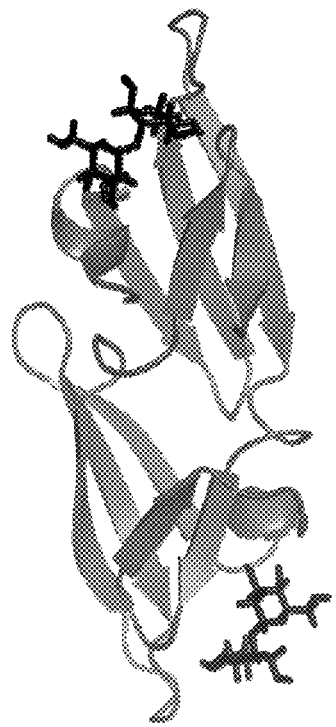
FIG. 1 provides a diagram of a wild-type (WT) CVN structure. In solution, WT CVN exists mainly as a monomer (A), while it crystallizes as a domain-swapped dimer (B). CVN is shown in gray ribbons to indicate protein chains. Carbohydrates are shown in a stick model with black atoms. The monomer and the left half of the dimer are in approximately the same orientation.
Figure 1:
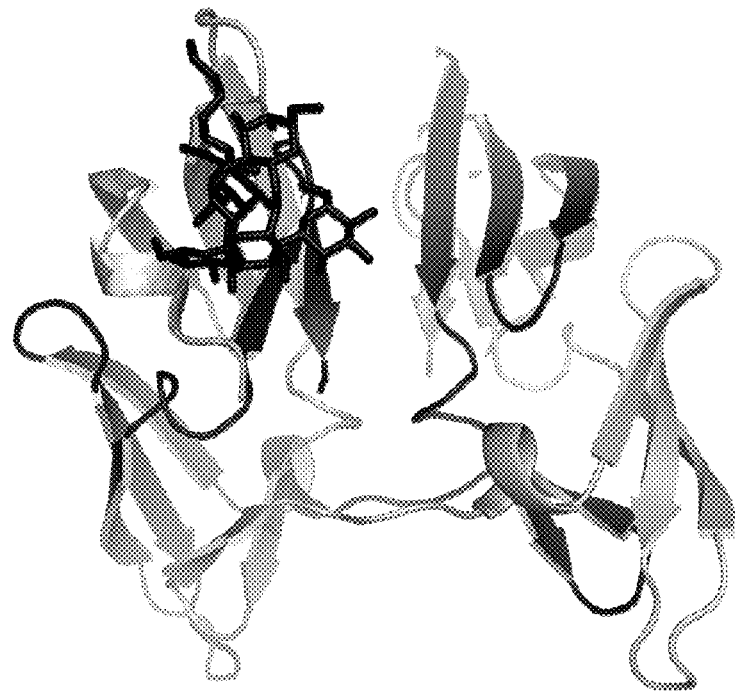

The current invention is directed to novel engineered lectins designed to bind to and neutralize a broad range of viruses containing glycosylated envelope proteins. The invention pursues two distinct but related lines of revolutionary antiviral protein reagents: the enhancement of the natural mode of action of lectins through linked multimerization, and the development of novel lectin-based reagents that have the dual capability of neutralizing viral infection by binding carbohydrates on glycoproteins involved in target cell recognition and by recruiting host immune effector function.

Before discussing the details of the invention, it is important to understand the basic mechanism of conventional lectins. Lectins are sugar-binding proteins, which are highly specific for their sugar moieties. They typically play a role in biological recognition phenomena involving cells and proteins. For example, some viruses use lectins to attach themselves to the cells of the host organism during infection. Lectins are also known to play important roles in the immune system by recognizing carbohydrates that are found exclusively on pathogens, or that are inaccessible on host cells. Examples are the lectin complement activation pathway and mannose binding lectin.

Naturally occurring lectins are known to bind to and neutralize a broad range of viruses making them excellent starting materials for protein engineering efforts aimed at developing novel therapeutic agents. For example, lectins have been shown to be powerful reagents for the neutralization of virus infection with a mechanism of action related to their ability to bind carbohydrates on the glycoproteins of enveloped viruses. (See, Balzarini, 2007, cited above.) Virus neutralization is achieved, because the lectins physically obstruct the interaction of virus and target cells, and as such, lectins can be useful prophylactic reagents for preventing viral infection (e.g., the lectin cyanovirin-N (CVN) is being pursued as a potential therapeutic for preventing HIV infection because of its ability to bind to glycosylated gp120).

The current invention is directed to engineered lectins for use as reagents for both preventing and treating a broad array of viral infections. The invention engineers lectins in two ways, first through the enhancement of the natural mode of action of lectins against viruses through linked multimerization, and second through the creation of a new class of reagents, hereinafter referred to as a "lectibody" or "lectibodies", that engage host immune function in addition to simply binding glycosylated viral proteins via the creation of a chimera made by fusing a lectin and the Fc region of an antibody in order to drive ADCC-like (antibody-dependent cell-mediated cytotoxicity) immune function and other Fc-mediated effector functions in response to a lectin-mediated carbohydrate-binding event.

Accordingly, in a first embodiment the invention is directed to lectins engineered with improved properties through linked multimerization. As discussed above, lectins operate to neutralize viruses by binding to glycosylated envelope proteins of these viruses and blocking critical interactions between the virus and the host cell, thus preventing infection. In this embodiment, multimeric lectin variants that contain a tandem repeat of the lectin are covalently linked through a flexible polypeptide linker.

It has been surprisingly discovered that covalently linking lectins to form multimeric structures stabilizes the active domains of the lectin, thereby allowing for better control of the position of the carbohydrate binding sites. In particular, it is possible to engineer the distances between carbohydrate binding sites so that they are more consistent and so that these distances better match the distance between the binding sites in the target virus envelope. In addition, it has been found that it is possible to further tailor the properties of these multimeric lectins by varying the length of the linker. For example, several multimeric cyanovirin-N (CVN) lectins were engineered in accordance with the current invention. A full discussion of the potency and properties of these multimeric CVN antiviral proteins are provided below; however, a brief explanation of the process is provided here to elucidate the general principals of the invention.

CVN is an antiviral lectin originally isolated from the cyanobacterium *Nostoc ellipsosporum* that has broad specificity for enveloped viruses. In particular, CVN has been shown to effectively neutralize various enveloped viruses, including HIV, influenza, and Ebola. (See, Boyd, M. R., et al., *Antimicrob Agents Chemother*, 41, 1521-30, 1997; O'Keefe, B. R., et al., *Antimicrob Agents Chemother*, 47, 2518-25, 2003; and Barrientos, L. G., et al., *Antiviral Res*, 58, 47-56, 2003, the disclosures of which are incorporated herein by reference.) CVN specifically binds α1-2 linked oligomannose sites on the glycosylated envelope proteins of these viruses and blocks critical interactions between the virus and the host cell, thus preventing infection.

Dimeric CVN variants ($CVN_2s$) that contain a tandem repeat of CVN linked through a flexible polypeptide linker were created in accordance with the current invention. These proteins consist of two copies of wild-type (WT) CVN linked with a flexible linker of varying length. Linker lengths ranging from 0 amino acids (L0) to 20 amino acids (L20) were tested, and it was found that some of the variants displayed significantly better HIV neutralization than WT. Specifically, $CVN_2$ L0 was up to 35 times more effective than WT against HIV.

Structural studies show that $CVN_2$ L0, $CVN_2$ L1, and $CVN_2$ L10 all crystallize as intramolecularly domain-swapped dimers and have a great degree of similarity to WT CVN domain-swapped structures. There were no major differences between the linked dimers and WT CVN, and therefore major structural changes do not contribute to the increase in HIV neutralization. However, in the engineered CVN variants, the distance between carbohydrate binding sites in CVN become more consistent and these distances are similar to the distance between the binding sites in the broadly neutralizing anti-HIV antibody, 2G12. Accordingly, it has been shown that it is possible to engineer multimeric lectins in accordance with this invention such that the carbohydrate binding sites of the lectins can be positioned at the ideal geometric position to best neutralize the target virus resulting in dramatically enhanced viral neutralization potency.

As described briefly above, in another embodiment the invention is directed to a new class of chimeric molecule made via the combination of a lectin and the Fc region of an antibody. The unique combination of the carbohydrate binding ability of a lectin with the immune system activating ability of an antibody allows for viral neutralization by a completely novel mode of action, and have the potential to act both in a pre-exposure prophylactic mode as well as a post-exposure therapeutic mode. Moreover, as with the lectin multimers, these lectibodies are also dimerized through the Fc domain.

The lectibody also has the potential for Fc-mediated effector functions as described above. Previous studies have shown that antibody-dependent cellular cytotoxicity (ADCC) plays a role in protection against HIV and that ADCC and other FcR-mediated effector functions provide some protection against viruses even when associated with non-neutralizing antibodies. (See, Hessell, A. J., et al., *Nature*, 449, 101-4, 2007; Florese, R. H., et al., *J Immunol*, 177, 4028-36, 2006; Gomez-Roman, V. R., et al., *J Immunol*, 174, 2185-9, 2005; Huber, V. C., et al., *J Immunol*, 166, 7381-8, 2001; Baldridge, J. R. & Buchmeier, M. J., *J Virol*, 66, 4252-7, 1992; Holl, V., et al., *J Virol*, 80, 6177-81, 2006; and Holl, V., et al., *Blood*, 107, 4466-74, 2006, the disclosures of each of which are incorporated herein by reference.) However, beyond ADCC function, these lectibodies can also be designed to exhibit other effector functions such as, for example, complement-dependent cytotoxicity (CDC), and antibody-dependent cell-mediated phagocytosis (ADCP). It is also anticipated that this lectibody construct will have a longer half-life in vivo due to the addition of the Fc region. A study on an exemplary lectin, CVN, showed that after subcutaneous injection in mice, WT CVN was mostly cleared from the bloodstream after 7 to 24 hours. (See, Bringans, S. D., et al., *Anal Bioanal Chem*, 380, 269-74, 2004, the disclosure of which is incorporated herein by reference.) Since a daily injection to maintain therapeutic levels would most likely not be feasible, a variant with a longer half-life would make a potential therapeutic more practical.

Moreover, lectibodies can be targeted to viruses of interest by fusing Fc to lectins known to preferentially bind specific viral targets. In addition, the risk of non-specific binding to endogenous host glycoproteins can be mitigated by screening computationally designed combinatorial libraries generated to have amino acid sequence diversity in the lectin carbohydrate binding region. Negative selection in cell-based assays can be used to identify lectibody variants that are both active against virus and diminished for non-specific binding.

A particularly exciting prospect for lectibodies is the potential to use these constructs in a prophylactic format in an aerosolized preparation that would be delivered to the lungs in order to provide pre-exposure protection to airborne agents. In this mode, the lectibody would initially reside on the surface of lung epithelial cells and would neutralize viruses by preventing interaction with host factors. Because the lectibody contains an Fc domain, the lectibody would also be transferred to the blood stream via transcytosis using the neonatal Fc receptor (FcRn), which also serves to protect Fc containing molecules (e.g., antibodies) from destruction and/or clearance, providing long-term protection against any current or subsequent infection. The concept of pulmonary delivery of Fc-containing proteins has already been demonstrated in non-human primates and is currently being developed for clinical applications by Syntonix. (See, Bitonti, A. J., et al., *Proc Natl Acad Sci USA*, 101, 9763-8, 2004; Dumont, J. A., et al., *J Aerosol Med*, 18, 294-303, 2005; and Low, S. C., et al., *Hum Reprod*, 20, 1805-13, 2005, the disclosures of each of which are incorporated herein by reference.)

Although the above examples have focused on CVN variants, it should be understood that the techniques of the current invention are generic to any lectin suitable for binding with glycosylated viral envelope proteins, such as, for example, griffithsin (GRFT), scytovirin, actinohivin, defensins (such as RC2 and HNPs), *Microcystis viridis* lectin (MVL), *Oscillatoria agardhii* agglutinin, Hippeastrum hybrid agglutinin (HHA), mannose-binding lectin (MBL), and *Urtica diolca* agglutinin (UDA). (See, Botos, I., and Wlodawer, A., *Prog Biophys Mol Bio*, 88(21, 233-282, 2005; Balzarini, J., et al., *J Virol*, 80(17), 8411-8421, 2006; Saidi, H., et al., *J Transl Med*, 5, 28-36, 2007; Balzarini, J., *Antivir Chem Chemother*, 18(1), 1-11, 2007; Bokesch, H. R., et al., *Biochem*, 42(9), 2578-2584, 2003; McFeeters, R. L., et al., *J Mol Bio*, 369(2), 451-461, 2007; Li, Y., et al., *Curr Med Chem*, 15(11), 1096-1104, 2008; O'Keefe, B. R., et al., *Proc Natl Acad Sci USA*, 106(15), 6029-6030, 2009; Emau, P., et al., *J Med Primatol*, 36, 244-253, 2007; Willaims, D. C. Jr., et al., *J Biol Chem*, 280(32), 29269-29276, 2005; Bewley, C. A., et al., *J Mol Bio*, 339, 901-914, 2004; Chiba, H., et al., *Biochem Biophys Res Comm*, 282, 595-601, 2001; Bokesch, H. R., et al., *FEBS Letters*, 567, 287-290, 2004; Leikina, E., et al., *Nature Immunology*, 6(10), 995-1001, 2005; Wang, W., et al., *J Immunology*, 173, 515-520, 2004; and Ji, X., et al., *J General Virology*, 86, 2535-2542, 2005; the disclosures of each of which are incorporated herein by reference.) For example, tandem repeat lectin oligomers could be formed from these non-CVN lectins, or multi-species lectin dimers and trimers (e.g., CVN2-UDA, CVN2-MBL, GRFT2-MVL, or MVL-CVN2).

In addition, these non-CVN lectins could be used to form lectibodies with the Fc region of an antibody as described in the exemplary embodiment below.

Finally, although the above discussion has focused on the engineered lectins themselves, it should also be understood the current invention is further directed to the treatment and prevention of enveloped virus infections in patients by the administration of therapeutically effective amounts of the engineered lectins in accordance with the current invention.

Once engineered lectins have been identified as eliminating, ameliorating or preventing the effects of a particular enveloped virus, these compounds can be used as therapeutic agents, provided they are biocompatible with the animals, preferably humans, to whom they are administered.

The therapeutic agents of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. Administration of the compounds can be administered in a variety of ways known in the art, as, for example, by oral, buccal, rectal, parenteral, intraperitoneal, intradermal, transdermal, intratracheal, inhalation, intranasal, etc., administration.

Depending upon the particular route of administration, a variety of pharmaceutically acceptable carriers, well known in the art can be used. These carriers include, but are not limited to, sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water. Preservatives and other additives can also be present. For example, antimicrobial, antioxidant, chelating agents, and inert gases can be added (see, generally, Remington's Pharmaceutical Sciences, 16th Edition, Mack, (1980)).

The concentration of therapeutically active compound in the formulation may vary from about 0.1-100 wt. %.

Those of skill will readily appreciate that dose levels can vary as a function of the specific therapeutic agents, the severity of the symptoms and the susceptibility of the subject to side effects. Preferred dosages for a given therapeutic agent are readily determinable by those of skill in the art by a variety of means. A preferred means is to measure the physiological potency of a given therapeutic agent as is known in the art.

EXEMPLARY EMBODIMENTS

The person skilled in the art will recognize that additional embodiments according to the invention are contemplated as being within the scope of the foregoing generic disclosure, and no disclaimer is in any way intended by the foregoing, non-limiting examples.

Although the methods of engineering lectins in accordance with the current invention are generic to all lectins, the following examples focus on reengineering cyanovirin-N (CVN), a potent antiviral lectin. CVN was investigated because it is well positioned to become a novel therapeutic and prophylactic for the prevention and treatment of infections from enveloped viruses. CVN is a small 11-kDa protein that was originally isolated from the cyanobacterium *Nostoc ellipsosporum* during a high-throughput screen intended to discover novel anti-HIV activities, and has been shown to interact with the HIV envelope glycoprotein gp120, and to be active against various strains of HIV, including primary isolates of HIV-1, T-lymphocyte-tropic strains, macrophage-tropic strains, and HIV-2. (See, e.g., Boyd, M. R., et al., *Antimicrob Agents Chemother*, 41, 1521-30, 1997, the disclosure of which is incorporated herein by reference.)

In addition to its potent activity against HIV, CVN has also been shown to effectively neutralize influenza, Ebola, hepatitis C, herpes virus, and measles virus. (See, e.g., Tsai, C. C., et al., *AIDS Res Hum Retroviruses*, 20, 11-8, 2004; Tsai, C. C., et al., *AIDS Res Hum Retroviruses*, 19, 535-41, 2003; Balzarini, J., et al., *J Virol*, 80, 8411-21, 2006; O'Keefe, B. R., et al., *Antimicrob Agents Chemother*, 47, 2518-25, 2003; Smee, D. F., et al., *Antivir Chem Chemother*, 18, 317-27, 2007; Barrientos, L. G. & Gronenborn, A. M., *Mini Rev Med Chem*, 5, 21-31, 2005; Barrientos, L. G., et al., *Antiviral Res*, 58, 47-56, 2003; and Helle, F., et al., *J Biol Chem*, 281, 25177-83, 2006, the disclosures of each of which are incorporated herein by reference.)

In short, CVN has great potential therapeutic value both as a prophylactic as well as a treatment for viral infection. In fact, wild type CVN is currently in clinical trials as a prophylactic gel (Cellegy Pharmaceuticals, Inc.), and has been shown to be effective against both rectal and vaginal SIV/HIV-1 transmission in non-human primate studies when used as a topical microbicide. (See, Tsai, C. C., et al., *AIDS Res Hum Retroviruses*, 20, 11-8, 2004; and Tsai, C. C., et al., *AIDS Res Hum Retroviruses*, 19, 535-41, 2003, the disclosures of each of which are incorporated herein by reference.) Additionally, it has been shown that CVN has limited toxicity in tissue culture, in mice, and in non-human primate models, although a recent study indicates that CVN can increase the levels of chemokines in treated cells and potentially allow much higher susceptibility for viral replication after CVN is removed. (See, e.g., Tsai, et al., 2004 & 2003, cited above; Esser, M. T., et al., *J Virol*, 73, 4360-71, 1999; Bringans, S. D., et al., *Anal Bioanal Chem*, 380, 269-74, 2004; Zappe, H., et al., *Adv Drug Deliv, Rev* 60, 79-87, 2008; and Sugrue, R. J., *Methods Mol Biol*, 379, 1-13, 2007, the disclosures of each of which are incorporated herein by reference.)

Additionally, CVN can be prepared in large quantities, is stable for long periods of time, and is extremely resistant to degradation. (See, e.g., Mori, T., et al., *Protein Expr Purif*, 26, 42-9, 2002; Mori, T., et al., *Protein Expr Purif*, 12, 151-8, 1998; and Colleluori, D. M., et al., *Protein Expr Purif*, 39, 229-36, 2005, the disclosures of each of which are incorporated herein by reference.) It was also demonstrated that WT CVN can be specifically PEGylated to increase the serum half-life while retaining most of the anti-HIV activity. (See, Zappe, H., et al., *Adv Drug Deliv Rev*, 60, 79-87, 2008, the disclosure of which is incorporated herein by reference.)

Although the viral neutralization activity of CVN is important in the prevention of infection, this function may prove even more beneficial as a potential therapeutic. Because CVN specifically targets glycosylation on viral envelopes, escape variants will likely appear upon treatment with this lectin. Under evolutionary pressure by CVN and other carbohydrate-binding proteins, HIV and influenza have both been shown to eliminate N-linked glycosylation sites on their envelope proteins to escape neutralization. (See, e.g., Hu, Q., et al., *Virology*, 368, 145-54, 2007; Witvrouw, M., et al., *J Virol*, 79, 7777-84, 2005; Wei, X., et al., *Nature*, 422, 307-12, 2003; Balzarini, J., et al., *J Biol Chem*, 280, 41005-14, 2005; and Balzarini, J., et al., *Mol Pharmacol*, 67, 1556-65, 2005, the disclosures of each of which are incorporated herein by reference.)

However, HIV-1 and other viruses use glycosylation to prevent recognition by the innate and adaptive immune systems. (See, e.g., Balzarini, J., *Nat Rev Microbiol*, 5, 583-97, 2007, the disclosure of which is incorporated herein by reference.) With the removal of glycosylation and the exposure of antigen, these viruses may become more sensitive to neutralization and clearance by the immune system. (See, Kang, S. M., et al., *Virology*, 331, 20-32, 2005; Kwong, P. D., et al., *Nature*, 393, 648-59, 1998; and Malenbaum, S. E., et al., *J Virol*, 74, 11008-16, 2000, the disclosures of each of which are incorporated herein by reference.) In fact, Reitter et al. found this to be true when rhesus monkeys were infected with SIV (simian immunodeficiency virus, an HIV homolog) lacking various glycosylation sites. In this case, the viruses were significantly more susceptible to antibody neutralization. (See, Reitter, J. N., et al., *Nat Med*, 4, 679-84, 1998, the disclosure of which is incorporated herein by reference.) Additionally, glycosylation of these viral proteins is often necessary for their proper folding and function, and therefore treatment with CVN or other lectins may decrease their viability. (See, e.g., Li, Y., et al., *J Virol*, 67, 584-8, 1993; and Sjolander, S., et al., *Virology*, 215, 124-33, 1996, the disclosures of each of which are incorporated herein by reference.)

Various attempts to increase the HIV neutralization of CVN have met with some success. Mori et al. showed that a chimera of CVN and an exotoxin from *Pseudomonas* had enhanced cytotoxicity to HIV-infected cells. (See, Mori, T., et al., *Biochem Biophys Res Commun*, 239, 884-8, 1997, the disclosure of which is incorporated herein by reference.) Another chimera between CVN and an allosteric peptide inhibitor of HIV-1 fusion also showed synergy between the two components, creating a more effective compound against HIV. (See, McFadden, K., et al., *Proteins* 67, 617-29, 2007, the disclosure of which is incorporated herein by reference.) Attempts to engineer CVN itself, however, have not resulted in variants with increased potency.

Exemplary Embodiment 1

Lectin Oligomerization Applied to HIV Neutralization

In a first embodiment of the invention, engineered lectins are described that have dramatically enhanced neutralization for targeted enveloped viruses. In particular, it has been surprisingly discovered that linked oligomerization of lectins results in a more than 10-fold enhancement of the intrinsic neutralization capability of CVN through engineered linked dimerization. Accordingly, in a first embodiment a lectin, such as, for example, CVN is oligomerized to enhance the interaction of the protein against specific glycosylation sites on the protein envelope of viruses.

Treatment and prevention of HIV-1 have proven to be difficult and complex problems. Vaccines thus far have been unsuccessful in generating broadly reactive neutralizing antibodies that confer immunity to the virus, partly because of HIV-1's rapid mutation rate and partly because of the lack of epitopes on its envelope proteins. The HIV-1 envelope is composed mainly of two proteins: gp41 and gp120, which are products of a single precursor protein, gp160. gp41 contains a transmembrane region, which anchors the envelope protein to the membrane, as well as a region that interacts specifically with gp120; gp120 contains binding sites for the primary receptor, CD4, and coreceptors, CCR5 and CXCR4. These gp41-gp120 dimers form trimers on the surface of the virus, creating the envelope spikes. (See, Zhu, P., et al., *Nature*, 441, 847-52, 2006, the disclosure of which is incorporated herein by reference.) While gp41 and gp120 by nature must contain some invariable regions, these conserved regions are typically masked or difficult to access. For example, the CD4 binding site is located in a cleft in the protein, allowing this region to evade the human immune system, and the binding sites for the co-receptors are revealed only after a conformational change induced by CD4 binding. (See, Burton, D. R., et al., *Proc Natl Acad Sci, USA* 102, 14943-8, 2005; Zhou, T., et al., *Nature*, 445, 732-7, 2007; and Sattentau, Q. J. & Moore, J. P., *J Exp Med*, 174, 407-15, 1991, the disclosures of each of which are incorporated herein by reference.) Additionally, gp120 and gp41 are both heavily glycosylated, obscuring many potential epitopes. In fact, approximately 50% of the apparent molecular weight of gp120 is attributed to complex carbohydrates. (See, Leonard, C. K., et al., *J Biol Chem*, 265, 10373-82, 1990, the disclosure of which is incorporated herein by reference.) This "silent face" of the HIV envelope is fairly resistant to the human immune system, because it is generated by the host and often recognized as "self."

In addition to the lack of functional epitopes on the envelope proteins of HIV-1, HIV is a retrovirus, and therefore has a very high mutation rate due to the error-prone reverse-transcriptase. Because of this rapid mutation rate, there is a great deal of variation in HIV viruses within an individual, between individuals, and geographically. A successful treatment or vaccine must therefore induce a broadly neutralizing response such that it affects many strains and many clades. Thus far, however, only a few broadly neutralizing antibodies have been isolated that are capable of neutralizing primary isolates of HIV-1. (See, Li, M., et al., *J Virol*, 79, 10108-10125, 2005; Li, M., et al., *J Virol*, 80, 11776-90, 2006; Trkola, A., et al., *J Virol*, 69, 6609-17, 1995; Binley, J. M., et al., *J Virol*, 78, 13232-52, 2004; and Karlsson Hedestam, G. B., et al., *Nat Rev Microbiol*, 6, 143-55, 2008, the disclosures of each of which are incorporated herein by reference.)

To date, four broadly neutralizing antibodies have been discovered and extensively studied. The first, IgG1b12, recognizes a conserved, recessed area of gp120 that overlaps with the CD4 binding site. IgG1b12 is capable of neutralizing approximately half of HIV-1 strains tested, including some strains from each clade. The monoclonal antibodies 4E10 and 2F5 both recognize conserved areas of gp41, near the viral membrane, but differ in their abilities to neutralize HIV-1. 4E10 is the most broadly reactive of these neutralizing antibodies, neutralizing all 93 strains tested from 12 different clades. (See, Ofek, G., et al., *J Virol*, 78, 10724-37, 2004; and Cardoso, R. M., et al., *Immunity*, 22, 163-73, 2005, the disclosures of each of which are incorporated herein by reference.) Unfortunately, although it is able to neutralize broadly, it does so with only modest potency. (See, Binley, J. M., et al., 2004, cited above.) 2F5, on the other hand, is not capable of neutralizing most viruses from lade C and is effective against only approximately 50% of lade B viruses. (See, e.g., Binley, J. M., et al., 2004, cited above.) The final anti-HIV antibody is 2G12. 2G12 differs from the other broadly neutralizing antibodies in that it recognizes the carbohydrates on gp120 and not the actual protein itself. (See, Trkola, A., et al., *J Virol*, 70, 1100-8, 1996, the disclosure of which is incorporated herein by reference.) In contrast to the standard "Y" structure of antibodies, the Fabs of 2G12 form a domain-swapped structure that allows it to bind two carbohydrate chains approximately 35 Å apart. (See, Calarese, D. A., et al., *Science*, 300, 2065-71, 2003, the disclosure of which is incorporated herein by reference.) 2G12 is mostly effective against viruses from clade B and exhibits limited or no neutralization of viruses from other clades. (See, e.g., Binley, J. M., et al., 2004, cited above.)

CVN is uniquely suited to play a role in HIV treatment and prevention. (See, Boyd, M. R., et al., *Antimicrob Agents Chemother*, 41, 1521-30, 1997, the disclosure of which is incorporated herein by reference.) CVN, like the 2G12 antibody, binds specifically to α1-2 oligomannose molecules, which are highly expressed on gp120, and neutralizes enveloped viruses including HIV, Ebola, and influenza. (See, Boyd, M. R., et al., *Antimicrob Agents Chemother*, 41, 1521-30, 1997; Bewley, C. A., *Structure*, 9, 931-40, 2001; Barrientos, L. G., et al., *Antiviral Res*, 58, 47-56, 2003; and O'Keefe, B. R., et al., *Antimicrob Agents Chemother*, 47, 2518-25, 2003, the disclosures of each of which are incorporated herein by reference.) Also like 2G12, CVN contains two carbohydrate-binding sites per molecule, indicating there is a potential avidity effect upon binding. (See, Bewley, C. A., 2001, cited above.) CVN is also distinctive in its small size. The 11-kDa protein is much smaller than even a single-chain Fv fragment (scFv) and therefore has the ability to bind to areas on gp120 that are sterically occluded from scFv, Fab, or IgG binding. (See, Labrijn, A. F., et al., *J Virol*, 77, 10557-65, 2003, the disclosure of which is incorporated herein by reference.) Additionally, unlike 2G12, which is specific to carbohydrates on specific residues, CVN is specific only to the type of linkage and therefore less sensitive to escape mutations that eliminate a single glycosylation site. (See, Balzarini, J., *Antivir Chem Chemother*, 18, 1-11, 2007, the disclosure of which is incorporated herein by reference.) In fact, glycosylation on gp120 has been shown to increase over the course of infection and act as a mechanism for escape from neutralizing antibodies. (See, Dacheux, L., et al., *J Virol*, 78, 12625-37, 2004; and Wei, X. P., et al., *Nature*, 422, 307-312, 2003, the disclosures of each of which are incorporated herein by reference.) CVN may be an optimal therapeutic in these cases due to its reaction to a broad range of high mannose carbohydrates.

Because of its promise, the structure of CVN has been extensively studied to attempt to elucidate a mechanism for its broad antiviral activity. Accordingly, much is known about how naturally occurring, or wild-type, CVN operates to neutralize viruses. As described above, CVN is a lectin with two carbohydrate binding sites that specifically bind to $\alpha(1-2)$ linked oligomannose moieties within Man-8 or Man-9 glycosylation sites. (See, e.g., Bolmstedt, A. J., et al., *Mol Pharmacol*, 59, 949-54, 2001; Bewley, C. A. & Otero-Quintero, S., *J Am Chem Soc* 123, 3892-902, 2001; Shenoy, S. R., et al., *Chem Biol*, 9, 1109-18, 2002; and Shenoy, S. R., et al., *J Pharmacol Exp Ther*, 297, 704-10, 2001, the disclosures of each of which are incorporated herein by reference.) Interestingly, high mannose glycosylation is very uncommon in mammalian oligosaccharides, but is often seen on the surface of viruses and microorganisms, creating an important distinction between the recognition of pathogens during potential treatment with CVN. (See, Weis, W. I., et al., *Immunol Rev*, 163, 19-34, 1998, the disclosure of which is incorporated herein by reference.) The two carbohydrate binding sites in CVN show distinct affinities for Man-9: the "high affinity" binding site has a $K_a$ of $7.2 \times 10^6$ M, and the "low affinity" binding site has an approximately 10-fold lower affinity. Later studies confirmed that both binding sites are important for HIV neutralization, and the destruction of either site renders the CVN variant inactive. (See, e.g., Fromme, R., et al., *Protein Sci* 17, 939-44, 2008; Fromme, R., et al., *Biochemistry*, 46, 9199-207, 2007; and Matei, E., et al., *Structure*, 16, 1183-94, 2008, the disclosures of each of which are incorporated herein by reference.)

These two binding sites provide a mechanism for high affinity and high avidity interactions with glycosylated envelope proteins on viruses. In each case, CVN binds specifically to high mannose glycosylation sites on envelope glycoproteins and inhibits vital interactions between the virus and the host cell. To date, CVN has shown no antiviral activity against any non-enveloped viruses, including rhinoviruses and enteric viruses, and also appears to be inactive against some enveloped viruses, including vaccinia. (See, Dey, B., et al., *J Virol*, 74, 4562-9, 2000, the disclosure of which is incorporate herein by reference.)

In the case of influenza, CVN interacts with glycosylation sites on hemagglutinin, one of the two surface glycoproteins expressed on influenza particles. CVN showed highly potent antiviral activity against strains of influenza A, including H1N1 and N3N2, exhibited moderate neutralization against influenza B strains, and was able to protect mice from a highly fatal strain of influenza when administered before infection or up to six hours post-infection. (See, Smee, D. F., et al., *Antiviral Res*, 80, 266-71, 2008, the disclosure of which is incorporated herein by reference.) Unfortunately, WT CVN showed no apparent activity against H5N1 strains ("bird flu"). (See, Smee, 2007, cited above.) However, with increased understanding of the specific interactions between CVN and hemagglutinin, engineered variants may provide increased neutralization of H5 and other strains, allowing a broad and potentially successful method for preventing infection in the case of an influenza outbreak in the absence of an effective vaccine.

Similarly to the mechanism for influenza neutralization, CVN inhibits HIV by binding to glycosylated surface proteins. In this case, CVN binds specifically and with high affinity to glycosylated gp120 and with significantly lower affinity to gp41. (See, O'Keefe, B. R., et al., *Mol Pharmacol*, 58, 982-92, 2000, the disclosure of which is incorporated herein by reference.) CVN binds with approximately 5:1 stoichiometry to soluble gp120, indicating that there are not only multiple sites of glycosylation to which CVN can bind, but that avidity may also play a significant role in the neutralization of HIV. Additionally, studies have shown that CVN does not bind to a single glycan on gp120, but instead three to five separate N-linked glycosylation sites must be mutated before CVN resistance is incurred. (See, e.g., Hu, O., et al., *Virology*, 368, 145-54, 2007; and Witvrouw, M., et al., *J Virol*, 79, 7777-84, 2005, the disclosures of each of which are incorporated herein by reference.) Although CVN-treated gp120 can still bind to soluble CD4, membrane-bound CD4 binding is inhibited, due to steric constraints. (See, e.g., Mariner, J. M., et al., *Biochem Biophys Res Commun*, 248, 841-5, 1998.) CVN also blocks the interaction between gp120 and the CCR5 co-receptor, adding a secondary inhibitory effect. These two mechanisms together make CVN an efficient inhibitor of the premembrane fusion event of HIV infection.

In addition to elucidating the binding sites targeted by CVN, structural studies have also examined the role the conformation of the protein plays in neutralizing viral species. CVN exists in solution mainly as a monomer, but a trapped, metastable domain-swapped dimer can be formed. In crystal form, however, wild-type (WT) CVN is only seen as a domain-swapped dimer, as shown in FIG. 1.

The monomer contains two pseudo domains that display high sequence homology. Interestingly, however, the gene does not appear to result from a simple gene duplication since the first domain contains residues 1-39 and 90-101, and the second domain contains residues 39-89. (See, Bewley, C. A., et al., *Nat Struct Biol*, 5, 571-8, 1998, the disclosure of which is incorporated herein by reference.) Instead, there was probably a gene duplication then rearrangement or an uneven recombination event that resulted in the CVN gene. Monomeric CVN also contains two native disulfide bridges: between residues 8 and 22, and between residues 58 and 73. These two disulfide bridges are located near each end of the molecule and anchor the secondary structure.

The dimer contains the same topology, but is domain-swapped at residues 51-53. (See, Yang, F., et al., *J Mol Biol*, 288, 403-12, 1999, the disclosure of which is incorporated herein by reference.) In the dimeric structure, the first domain of one chain (A) forms a "monomer-like" structure with the second domain of the other chain (B) in an almost symmetric domain swapping, as shown in FIG. 1B. The two quasi-monomers can sample different orientations relative to each other due to the flexibility of the domain-swapped region, and the orientation appears to be pH dependent in crystal structures. (See, e.g., Botos, I. & Wlodawer, A., *Cell Mol Life Sci*, 60, 277-87, 2003, the disclosure of which is incorporated herein by reference.)

A number of groups have attempted to modulate the domain swapping of CVN to determine whether this property is a crystallographic artifact or a biologically relevant state. Because the domain-swapped dimer of WT CVN is metastable at physiological temperatures, purified dimer quickly converts to monomer during the course of a neutralization assay. (See, Barrientos, L. G., et al., *Structure*, 10, 673-86, 2002, the disclosure of which is incorporated herein by reference.) Variants have been generated that stabilize both the monomeric state and the dimeric state. (See, Kelley, B. S., et al., *J Am Chem Soc*, 124, 3210-1, 2002; and Barrientos, L. G., et al., *Structure*, 12, 1799-807, 2004, the disclosures of each of which are incorporated herein by reference.) However, until now the effect of dimerization has remained unclear, since some groups have concluded that the dimeric state is more active than monomeric WT CVN (Kelly, B. S., et al., 2002, cited above) and others have shown that monomeric and dimeric variants have the same antiviral activity (Barrientos, L. G., et al., 2004, cited above).

In the current invention it has been surprisingly discovered that engineered multimeric (dimeric and trimeric) CVN variants display dramatically increased HIV neutralization activity. Data from potency and structural studies are provided below.

Potency Data

In this study, results are presented proving the increased potency of dimeric and trimeric variants of CVN for neutralizing HIV-1. The molecules were expressed and purified to homogeneity and then assessed for their ability to prevent HIV-1 infection in a cell culture-based neutralization assay. It was surprisingly discovered that covalently linking two CVN monomers ($CVN_2$) through a flexible polypeptide linker decreased the concentration of protein at which 50% of the virus was neutralized ($IC_{50}$) up to thirty-five-fold compared to wild-type CVN. In addition, a linker-length dependence in the neutralization activity is presented, which allows for further tailoring of the potency of these novel species. In addition, CVN and dimeric variants in accordance with the current invention, displayed significant cross-clade and cross-strain reactivity against 33 strains of HIV-1 and neutralized most strains with decreased $IC_{50}$s compared to the most effective broadly neutralizing antibody tested.

In a first exemplary embodiment the lectin, CVN, was oligomerized to see if it was possible to increase the protein's efficacy of neutralization for HIV-1 and other enveloped viruses by engineering the number of binding sites and by varying the distances between those sites. Previous studies of 2G12 indicated that higher order oligomers are more effective at neutralizing HIV. West et al. showed that natural dimers of 2G12 are up to 80-fold more potent than the monomer, and the oligomeric 2G12-IgM engineered antibody tested by Wolbank et al. exhibited up to 28-fold greater efficacy than 2G12-IgG. (See, West, A. P., Jr., et al., *J Virol.*, 2008; and Wolbank, S., et al., *J Virol*, 77, 4095-103, 2003, the disclosures of which are incorporated herein by reference.)

Although CVN can also exist in a domain-swapped form, it was previously unknown whether the domain-swapped dimer exhibits similar increases in neutralization to 2G12, since differing accounts have been published. (Yang, F., et al., *J Mol Biol*, 288, 403-12, 1999; Barrientos, L. G., et al., *Structure*, 12, 1799-807, 2004; and Kelley, B. S., et al., *J Am Chem Soc*, 124, 3210-1, 2002, the disclosure of each of which are incorporated herein by reference.) The current invention shows that by dimerizing or trimerizing CVN, it is possible to both increase the number of binding sites and therefore potentially affect the avidity of binding, and also effectively increase the separation of binding sites and therefore possibly crosslink glycosylation sites that are separated by a greater distance.

Figure 2:
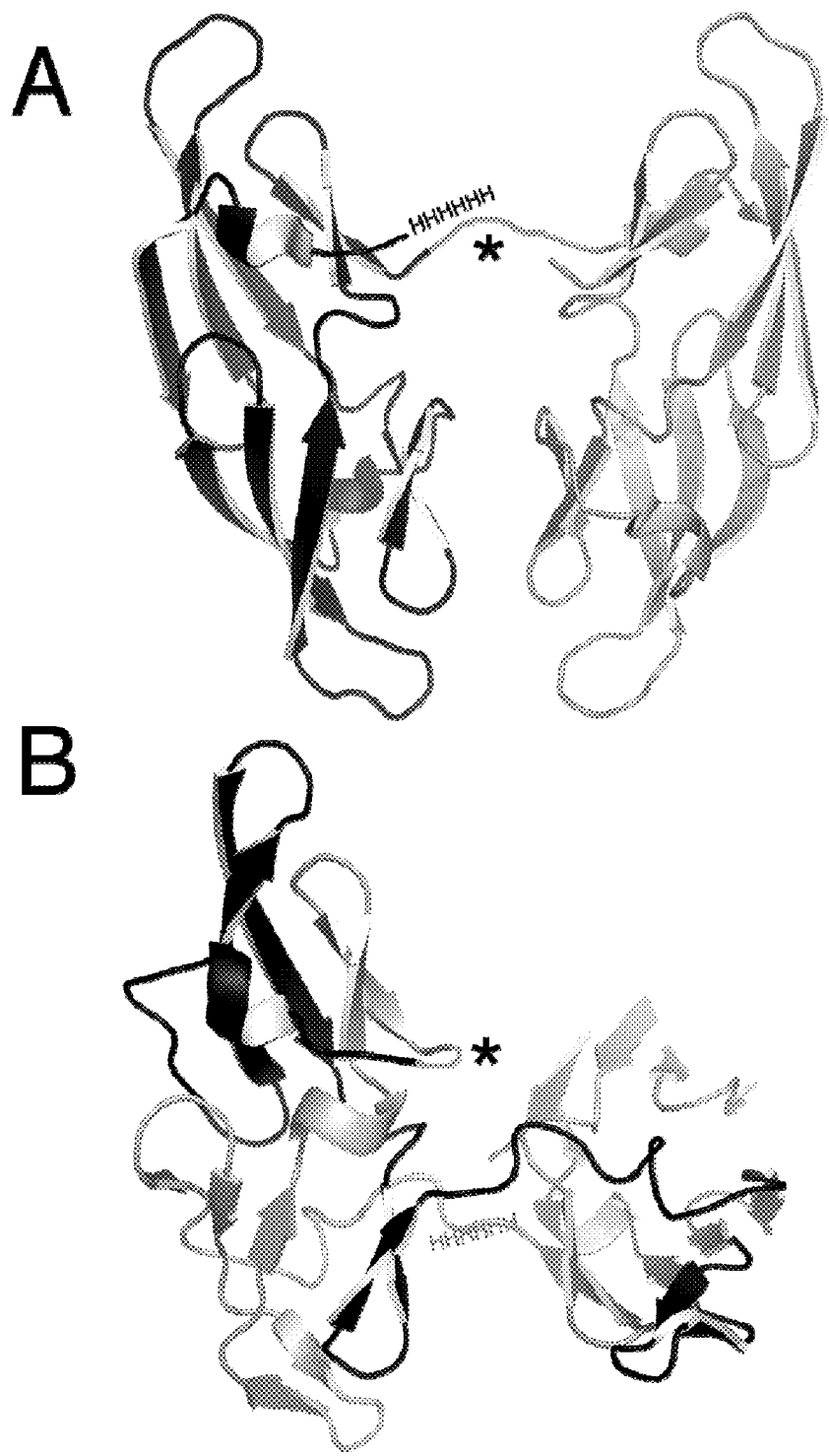
FIG. 2 provides a model of a generic $CVN_2$ protein. The CVN repeats are shown in light gray and dark gray and the flexible polypeptide linker is shown with an asterisks (*) marker. The N-terminal His-tag is depicted as HHHHHH. The $CVN_2$ structures may adopt a linked monomer structure (A) or a linked domain-swapped structure (B). These representations were created using solved WT CVN structures.

In addition to determining the effect of oligomerization on CVN efficacy, the current study also tested these variants against a large number of HIV-1 strains to ascertain their cross-clade neutralization. Through the instant invention linked dimers ($CVN_2$) and trimers ($CVN_3$) of CVN have been formed, and their HIV neutralization function assayed against 33 viruses from three clades. These variants were engineered with a polypeptide linker of varying length (L0 to L20) connecting the C-terminus of one CVN to the N-terminus of another, as shown in FIG. 2.

Methods

Construct generation. The gene for wild-type (WT) CVN was constructed using a recursive PCR method with 40-mer synthesized oligos, and cloned into the NdeI and BamHI sites of pET11a. (See, Stemmer, W. P., et al., *Gene*, 164, 49-53, 1995, the disclosure of which is incorporated herein by reference.) The protein contained an N-terminal 6-histidine purification tag followed by a Factor Xa protease cleavage site. $CVN_2$ L5 and $CVN_2$ L10 were constructed using PCR-based cloning to insert a tandem repeat of the WT CVN gene into the WT plasmid. The $CVN_3$ L5 gene was created by inserting an *Escherichia coli*-optimized WT CVN DNA sequence between the two existing copies of the WT gene in $CVN_2$ L5. Other dimeric and trimeric genes of varying linker lengths were constructed using the QuikChange Site-Directed Mutagenesis Kit to insert or delete codons corresponding to linker amino acids (Stratagene). All constructs were verified through DNA sequencing and restriction analysis to ensure the correct sequence and number of CVN repeats. (See, e.g., Kelley, B. S., et al., *J Am Chem Soc*, 124, 3210-1, 2002, the disclosure of which is incorporated herein by reference.)

Expression and Purification.

WT CVN and all oligomeric variants were expressed in BL21(DE3) *E. coli* cells in LB including ampicillin. The cultures were induced with 1 mM ITPG when the cells reached mid-log and grown for an additional 3-5 hours at 37° C. The harvested cells were lysed using an EmulsiFlex-C5 (Avestin, Inc.) and the insoluble fraction was resuspended in buffer containing 6 M GnHCl and 10 mM imidazole and centrifuged to remove debris. The solubilized CVN was then purified using a denatured protocol on a Ni-NTA gravity column (Qiagen). The protein was eluted in buffer containing 6 M GnHCl and 250 mM imidazole and transferred to dialysis tubing with a MWCO of 5,000 Da. WT CVN and all variants were refolded by dialyzing the Ni-NTA eluate against native buffer overnight at room temperature. (See, Barrientos, L. G., et al., *Proteins*, 46, 153-60, 2002, the disclosure of which is incorporated herein by reference.) Following refolding, the solution was filtered to remove any precipitant and concentrated using Amicon 5000 MWCO centrifugal concentrators to approximately 0.5 mL (Millipore). The proteins were then additionally purified on a Superdex-75 column and eluted in 25 mM sodium phosphate pH 7.4, 150 mM NaCl. Pure protein was concentrated or stored as eluted at 4° C. Attempts to cleave the His-tag using Factor Xa were unsuccessful under several conditions, so the tag was left intact for the studies described here. Amino acid analysis was performed on WT CVN, $CVN_2$ L5, $CVN_2$ L10, $CVN_3$ L5, and $CVN_3$ L10 to determine extinction coefficients at 280 nm. These experimentally determined extinction coefficients (WT: 10471 $M^{-1}cm^{-1}$, $CVN_2S$: 20800 $M^{-1}cm^{-1}$, $CVN_3s$: 32000 $M^{-1}cm^{-1}$) were used to calculate the protein concentration.

Surface Plasmon Resonance (SPR) Assays.

SPR (Biacore) experiments were performed on a T100 instrument (Biacore). Approximately 30 response units (RUs) of WT CVN were immobilized on flow cells 2 through 4 of a CM5 chip through standard amine coupling. Flow cell 1 was reserved as a control. All assays were conducted in HBS-EP buffer (10 mM HEPES pH 7.4, 150 mM NaCl, 0.0005% v/v Surfactant P20, 1 mM EDTA; Biacore). Various analytes were injected over the surface for 60 seconds at a flow rate of 30 µL/min. The chip was regenerated with two pulses of 50 mM NaOH. In some cases, complete regeneration was not achieved and a new chip was created. The data were analyzed for binding or lack of binding based on the sensorgram.

Cell Viability Assays.

Cellular toxicity was assayed using an XTT cell proliferation kit (MD Biosciences). This assay is based on the observation that live cells can reduce XTT and other tetrazolium salts, resulting in a colored solution. Cells that are not metabolically active, however, are not able to reduce XTT and therefore there is no color change after the addition of the reagent. WT CVN or a variant protein was incubated with approximately 5000 Tzm-Bl cells in D-MEM high glucose medium with L-glutamine, sodium pyruvate, 50 µg/mL gentamicin, and 10% heat inactivated BSA at 37° C. in a CO2 incubator for 48 hours. The prepared XTT reagent was added to each well and incubated for an additional two hours. The plates were shaken gently and the absorbance at 450 nm (the absorbance of the reduced XTT product) was measured on a Safire2 plate reader (Tecan). Each protein was assayed in triplicate, and the average absorbance values were used to determine the percent of cells that were viable (% Viable) using Equation 1, below, where $A_{CVN}$ is the absorbance of the well containing cells and CVN, $A_{negative}$ is the average absorbance of wells containing no cells or protein, and $A_{cell}$ is the average absorbance of wells containing cells but no CVN. The percent of viable cells was plotted as a function of the CVN concentration.

$$\% \text{ Viable} = \frac{A_{CVN} - A_{negative}}{A_{cell} - A_{negative}} * 100 \quad \text{(Eq. 1)}$$

HIV Neutralization Assays.

HIV neutralization assays were performed according to the methods by Li et al. (See, Li, M., et al., *J Virol,* 79, 10108-10125, 2005, the disclosure of which is incorporated herein by reference.) The assays used Tzm-Bl cells, a HeLa cell line that expresses CD4 and the HIV coreceptors CCR5 and CXCR4 and contains a viral Tat-induced luciferase reporter gene. Only when infected by the HIV-1 pseudovirus will these cells express luciferase, allowing a high-throughput measurement of neutralization. HIV-1 pseudovirus particles from pseudotyped primary virus strains were prepared as described. (See, Wei, X. P., et al., *Nature,* 422, 307-312, 2003, the disclosure of which is incorporated herein by reference.) The SC422661.8 strain (clade B) was used for all assays unless otherwise noted. One column of 8 wells in a 96-well plate contained cells but no virus and was used to determine the background level of luminescence (cell control). Additionally, one column contained cells and virus but no inhibitory compound, acting as both a positive control and a maximal signal of infection (viral control). In the remaining wells, approximately 250 $TCID_{50}$ of virus was incubated with varying amounts of CVN or CVN variant in triplicate for one hour at 37° C. Each plate contained WT in triplicate as an internal control. Typically eight threefold dilutions starting with 200 nM protein were tested to create a neutralization curve. Approximately 10,000 freshly trypsinized cells were added to each well and the plate was incubated for 48 hours. The cells were then lysed using Bright Glo Luciferase Assay Buffer (Promega), which was diluted 4×. The lysate was then transferred to a new plate and the luminescence was measured on a Victor3 Multilabel Counter (PerkinElmer, Inc.). To determine the $IC_{50}$ of neutralization, the luminescence corresponding to a given protein concentration was first averaged across the three replicates, then the percent neutralization (% Neutralization) was calculated based on Equation 2, where RLU is the average relative luminescence for a given concentration, CC is the average luminescence from the cell control wells, and VC is the average luminescence from the viral control wells.

$$\% \text{ Neutralization} = \left(1 - \frac{RLU - CC}{VC - CC}\right) * 100 \quad \text{(Eq. 2)}$$

The percent of virus neutralized was then plotted as a function of neutralizing protein in Kaleidograph (Synergy Software) and fitted to Equation 3, where $IC_{50}$ is the concentration of CVN at which 50% of the virus is neutralized and C is the concentration of CVN. The reported error is the error associated with the curve fit to the experimental data.

$$\% \text{ Neutralization} = \frac{100}{1 + \frac{IC_{50}}{C}} \quad \text{(Eq. 3)}$$

To minimize the plate-to-plate deviations between assays, each variant's $IC_{50}$ was normalized compared to WT $IC_{50}$ on the same plate. These data are presented as "$IC_{50}$:fold lower than WT" and were calculated by dividing the $IC_{50}$ for WT by the $IC_{50}$ for the variant. Each variant was independently tested between one and five times. Error bars were calculated by propagating the error from the WT and variant curve fits as well as multiple trials if applicable, according to standard methods. (See, Mori, T., et al., *Protein Expr Purif,* 26, 42-9, 2002, the disclosure of which is incorporated herein by reference.)

In addition to the above-described assays, WT CVN and two dimer variants were tested against multiple envelopes from various HIV-1 clades through the Collaboration for AIDS Vaccine Discovery (CAVD) Neutralizing Antibody Laboratory. These assays were performed according to the same protocol described above, but pseudoviruses from clades A, B, and C were tested to determine the cross-clade reactivity. (See, Vigerust, D. J. & Shepherd, V. L., *Trends Microbiol,* 15, 211-8, 2007, the disclosure of which is incorporated herein by reference.) The data were analyzed as described above.

Results

Dimer and trimer variants. To directly assay the effects of dimerization and trimerization on the activity of CVN, proteins were generated consisting of two or three tandem repeats of CVN, as shown in FIG. 2. The resulting proteins had one copy of the protein linked through its C-terminus to the N-terminus of the next copy through a flexible polypeptide linker encoded in the gene. In this study, dimers (CVN$_2$s) were tested with 14 different linkers ranging from 0 to 20 amino acids (all Gly or Ser) for their ability to neutralize HIV in a cell-based assay. In addition, trimers (CVN3s) were assayed with three linkers comprised of 0, 5, or 10 amino acids, see Table 1, below.

TABLE 1

CVN$_2$ and CVN$_3$ Linker Sequences

| Variant | Linker Sequence | Seq. ID. No |
|---|---|---|
| CVN$_2$ L0 | N/A | N/A |
| CVN$_2$ L1 | G | N/A |
| CVN$_2$ L3 | GSG | N/A |
| CVN$_2$ L5 | GGSGG | SEQ. ID 1 |
| CVN$_2$ L6 | GSGGSG | SEQ. ID 2 |
| CVN$_2$ L7 | (GGS)$_2$G | SEQ. ID 3 |
| CVN$_2$ L8 | (GGS)$_2$GG | SEQ. ID 4 |
| CVN$_2$ L9 | GGSGGGSGG | SEQ. ID 5 |
| CVN$_2$ L10 | (GGSGG)$_2$ | SEQ. ID 6 |
| CVN$_2$ L11 | (GGS)$_3$GG | SEQ. ID 7 |
| CVN$_2$ L13 | GGS(GGGS)$_2$GG | SEQ. ID 8 |
| CVN$_2$ L15 | (GGSGG)$_3$ | SEQ. ID 9 |
| CVN$_2$ L17 | GGS(GGGS)$_3$GG | SEQ. ID 10 |
| CVN$_2$ L20 | (GGSGG)$_4$ | SEQ. ID 11 |
| CVN$_3$ L0 | N/A | N/A |
| CVN$_3$ L5 | GGSGG | SEQ. ID 1 |
| CVN$_3$ L10 | (GGSGG)$_2$ | SEQ. ID 6 |

Expression and Purification.

WT and all CVN variants were expressed into inclusion bodies at 37° C. using standard *E. coli* expression protocols. After solubilizing the proteins in 6 M GnHCl and running a Ni-NTA purification step, the proteins were refolded by dialyzing against native buffer. Most of the refolded protein solutions, including those for WT, CVN$_2$ L0, CVN$_2$ L10, and CVN$_3$ variants, had little or no precipitation after dialysis, indicating the conditions were sufficient for refolding without favoring aggregation. Some variants, however, including CVN$_2$ L1 and CVN$_2$ L3, experienced significant precipitation during the refolding step. These solutions were filtered before continuing with the purification protocol. Gel filtration was performed on the refolded proteins to separate the desired species (WT: monomer; CVN$_2$s: dimer; CVN$_3$s: trimer) from higher molecular weight species including domain-swapped dimmers or tetramers and aggregates. WT CVN eluted at approximately 0.59 CV, CVN$_2$s eluted at approximately 0.54 CV, and CVN$_3$s eluted at approximately 0.50 on the gel filtration column. Reinjection of purified sample indicated the protein was stable in its purified oligomeric state for weeks to months when stored at 4° C.

Surface Plasmon Resonance (Biacore) Assays.

To assess the efficacy of the refolding protocol, WT CVN was assayed for its ability to bind gp120. WT CVN was immobilized to a Biacore chip and 100 nM gp120HxBc2 was flowed over. Significant binding was observed at all surface densities tested and the binding was virtually irreversible (data not shown). Various regeneration conditions including low pH, high pH, and high concentrations of NaCl were used, but the chip was never fully regenerated. It can therefore be concluded that WT CVN was properly folded and able to bind specifically to gp120.

The WT CVN was also tested for domain-swapping and aggregation on the surface. WT CVN was immobilized and WT and various CVN$_2$ proteins were analyzed for binding. No binding was observed for WT, CVN$_2$ L0, CVN$_2$ L1 or CVN$_2$ L10 (data not shown). These proteins did not aggregate on the surface or bind to WT CVN. No intermolecular domain-swapping was observed under these conditions.

HIV Neutralization Assays.

WT CVN was tested for its ability to neutralize HIV pseudovirus in cell culture. The IC$_{50}$ of CVN is reported to be in the low nanomolar range. (See, e.g., Colleluori, D. M., et al., *Protein Expr Purif*, 39, 229-36, 2005; Mori, T., et al., *Protein Expr Purif*, 26, 42-9, 2002; and Mori, T., et al., *Biochem Biophys Res Commun*, 238, 218-22, 1997, the disclosures of which are incorporated herein by reference.) In the assays, WT CVN neutralized HIV envelope SC422661.8 with IC$_{50}$s between 2 and 14 nM over 16 independent trials, consistent with published values. To minimize any plate-to-plate deviations due to incubation conditions, viral particle preparation, or other systematic differences, all variant data are reported relative to the WT IC$_{50}$ from the same 96-well plate.

Figure 3:
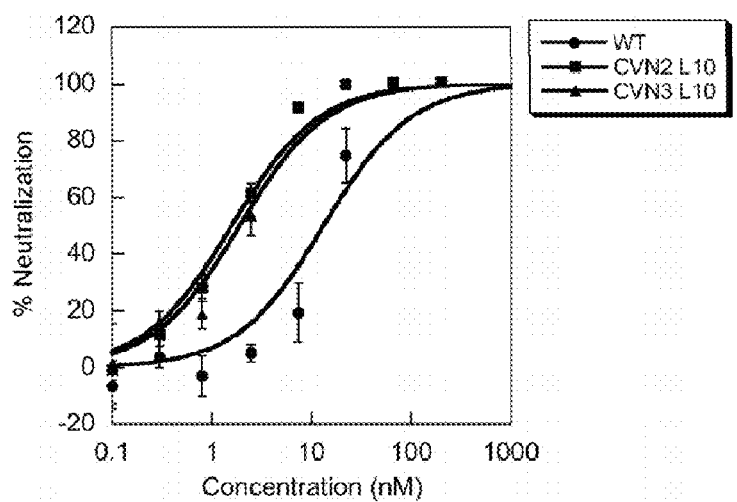
FIG. 3 provides HIV neutralization assay results. (A) Shows typical neutralization data for WT CVN and two variants run on the same plate. The data are analyzed and fit as described in the methods. (B) Provides a summary of $IC_{50}$s from various $CVN_2$s of differing linker lengths as compared to WT on the same plate. $CVN_2$ L0, $CVN_2$ L5, and $CVN_2$ L10 show the largest increase in efficacy over WT. All linked dimers, however, are at least two-fold more effective than WT.
Figure 3:
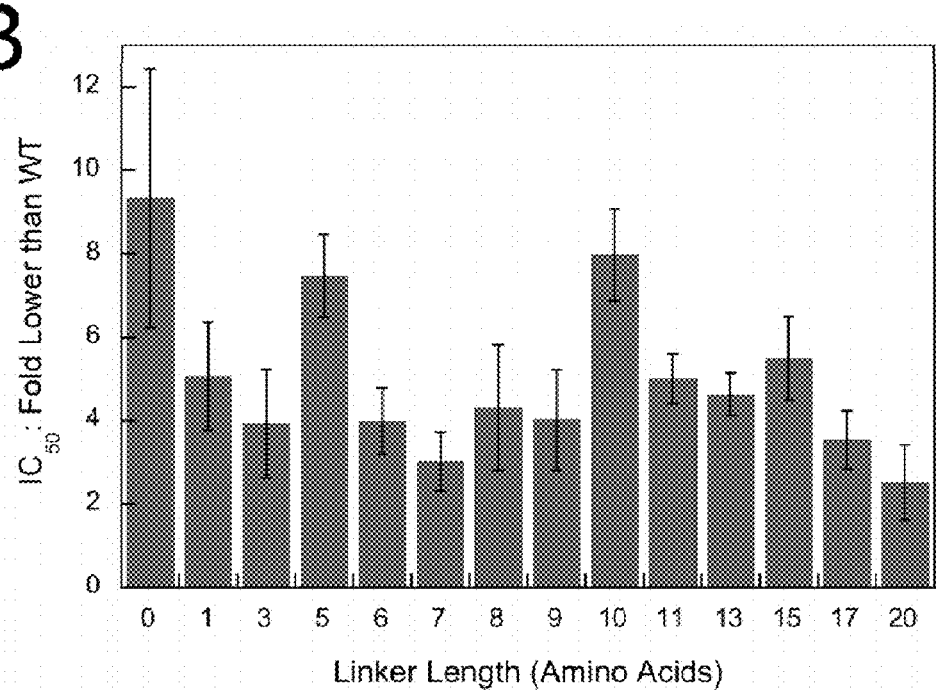

Dimeric CVN$_2$ proteins were also tested for their ability to neutralize HIV strain SC422661.8. This data is summarized in the data plot provided in FIG. 3. All variants displayed IC$_{50}$s lower than WT CVN, showing enhanced neutralization compared to WT. For CVN$_2$ L0 and CVN$_2$ L10, the increase in efficacy is nearly ten-fold. As shown, there is a linker-length dependence to the data, indicating that the activity of multimeric CVN may be engineered by varying the length of the linker.

Figure 4:
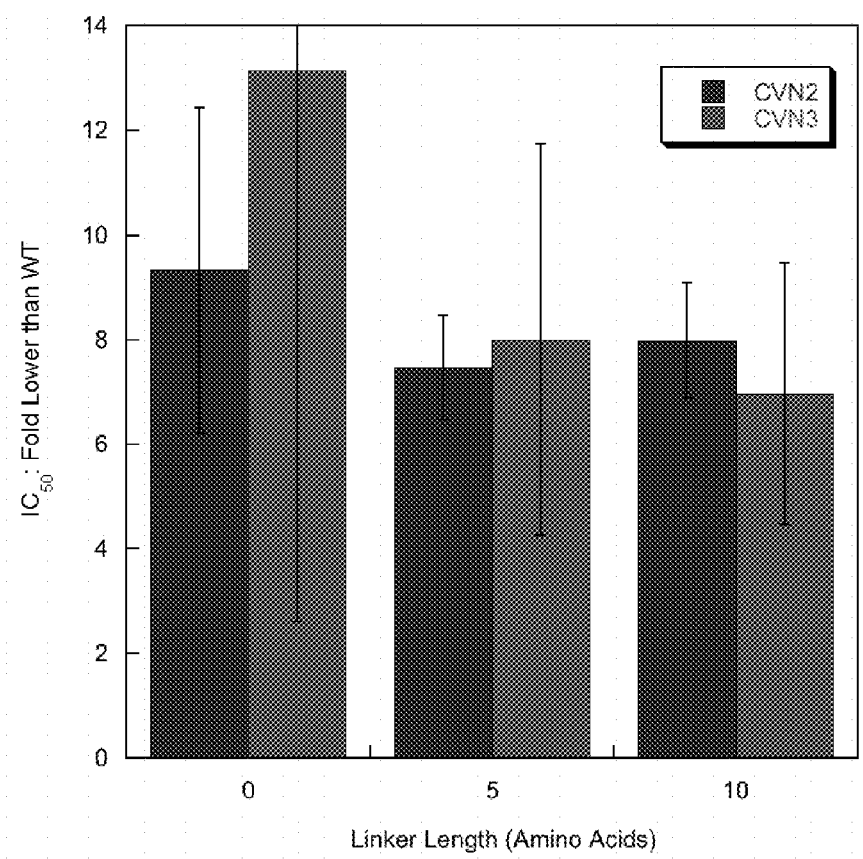
FIG. 4 provides $CVN_3$ HIV neutralization data. The $CVN_3$ variants are all significantly more effective at neutralizing HIV than WT, but there is no significant difference between $CVN_2$s (dark bars) and $CVN_3$s (light bars) of these linker lengths.

To test the hypothesis that more binding sites make better neutralizing variants, trimeric CVN$_3$ molecules were also engineered. Similar to the CVN$_2$ results, these variants were significantly more effective at HIV neutralization than WT. However, compared to the CVN$_2$ variant, adding an additional CVN repeat did not increase the efficacy of HIV neutralization, and the three variants tested (CVN$_3$ L0, CVN$_3$ L5, and CVN$_3$ L10) did not have significantly different activities from their CVN$_2$ counterparts. This data is summarized in the plots provided in FIG. 4.

After identifying CVN$_2$ L0 and CVN$_2$ L10 as the best performing oligomeric variants against the SC422661.8 strain, these proteins and WT CVN were also assayed for their cross-clade reactivity. The proteins were tested against a total of 33 viruses from three clades of HIV. The results of these experiments are provided in Table 2, below.

TABLE 2

IC$_{50}$ of CVN and HIV Neutralizing Antibodies (nM)[a]

| Clade | Envelope | 4E10 | 2G12 | 2F5 | IgG1b12 | CVN | CVN$_2$L0 | CVN$_2$L10 |
|---|---|---|---|---|---|---|---|---|
| A[b] | DJ263.8 | N/A | N/A | N/A | N/A | 7.48 | 0.46 | 0.48 |
| | Q23.17 | 108.75 | >300 | 46.25 | >300 | 15.4 | 1.35 | 2.59 |
| | Q842.d12 | 87.5 | >300 | 53.75 | >300 | 19.1 | 2.83 | 3.34 |
| | Q259.d2.17 | 89.375 | >300 | 66.25 | >300 | 162.6 | 13.79 | 41.1 |

TABLE 2-continued

IC$_{50}$ of CVN and HIV Neutralizing Antibodies (nM)[a]

| Clade | Envelope | 4E10 | 2G12 | 2F5 | IgG1b12 | CVN | CVN$_2$L0 | CVN$_2$L10 |
|---|---|---|---|---|---|---|---|---|
| | 3718.v3.c11 | 71.875 | >300 | 21.25 | >300 | 64.33 | 4.01 | 8.89 |
| | 0330.v4.c3 | 36.25 | 4.375 | 59.375 | >300 | 2.69 | 0.11 | 0.25 |
| | 3415.v1.c1 | 146.875 | 13.125 | 227.5 | 156.25 | 5.69 | 0.28 | 0.44 |
| B[c] | SF163.LS | 1.875 | 3.75 | 0.625 | 0.0625 | 16.43 | 1.05 | 1.69 |
| | PV0.4 | 40.625 | 7.5 | >300 | >300 | 4.09 | 0.23 | 0.49 |
| | CAAN5342.A2 | 16.875 | >300 | 22.5 | >300 | 34.29 | 9.49 | 14.61 |
| | W1TO4160.33 | 1.875 | 6.875 | 3.75 | 19.375 | 1.85 | 0.1 | 0.12 |
| | AC10.2.29 | 1.875 | >300 | 8.125 | 11.875 | 5.01 | 0.27 | 0.79 |
| | SC422661.8 | 5.625 | 13.125 | 4.375 | 1.25 | 4.21 | 0.24 | 0.42 |
| | 6535.3 | 1.25 | 12.5 | 11.875 | 8.75 | 18.26 | 1.35 | 2.56 |
| | THRO4156.18 | 1.875 | >300 | >300 | 3.125 | 7.75 | 0.59 | 0.74 |
| | REJO4541.67 | 4.375 | >300 | 3.75 | 4.375 | 11.48 | 0.5 | 0.68 |
| | TRJO4551.58 | 28.125 | >300 | >300 | >300 | 4.48 | 0.13 | 0.35 |
| | QH0692.42 | 8.75 | 17.5 | 6.25 | 1.875 | 14.32 | 1.02 | 2.39 |
| | TRO.11 | 1.875 | 2.5 | >300 | >300 | 9.57 | 0.53 | 0.85 |
| | RHPA4259.7 | 43.125 | >300 | 75 | 0.625 | 11.57 | 1.14 | 2.04 |
| C[d] | MW965.26 | N/A | N/A | N/A | N/A | 7.06 | 0.4 | 0.89 |
| | ZM197M.PB7 | 3.125 | >300 | 76.875 | 124.375 | 4.34 | 0.41 | 0.49 |
| | ZM249.PL1 | 13.125 | >300 | >300 | 20 | 22.93 | 1.93 | 2.31 |
| | ZM53M.PB12 | 43.75 | >300 | >300 | 161.875 | 19.24 | 1.41 | 3.42 |
| | ZM214M.PL15 | 25 | >300 | >300 | 18.75 | 29.35 | 1.46 | 2.59 |
| | Du156.12 | 1.25 | >300 | >300 | 5 | 24.32 | 1.99 | 3.8 |
| | Du442.1 | 4.375 | >300 | >300 | 1.25 | 5.02 | 0.28 | 0.48 |
| | Du172.17 | 1.875 | >300 | >300 | 6.25 | 3.31 | 0.33 | 0.38 |
| | CAP45.2.00.G3 | 16.25 | >300 | >300 | 4.375 | 1.21 | 0.17 | 0.41 |
| | CAP210.2.00.E8 | 7.5 | >300 | >300 | 127.5 | 16.75 | 1.43 | 1.03 |
| | ZM233M.PB6 | 7.5 | >300 | >300 | >300 | 4.56 | 0.24 | 0.29 |
| | ZM109F.PB4 | 3.75 | >300 | >300 | >300 | 18 | 2.77 | 5.49 |
| | ZM135M.PL10a | 3.75 | >300 | >300 | >300 | 16.79 | 1.89 | 3.08 |

[a]A molecular weight of 160,000 g/mol was used to convert neutralizing antibody data (4E10, 2G12, 2F5, IgG1b12) from μg/mL to nM.
[b-d]neutralizing antibody data obtained from third party sources.

Figure 5:
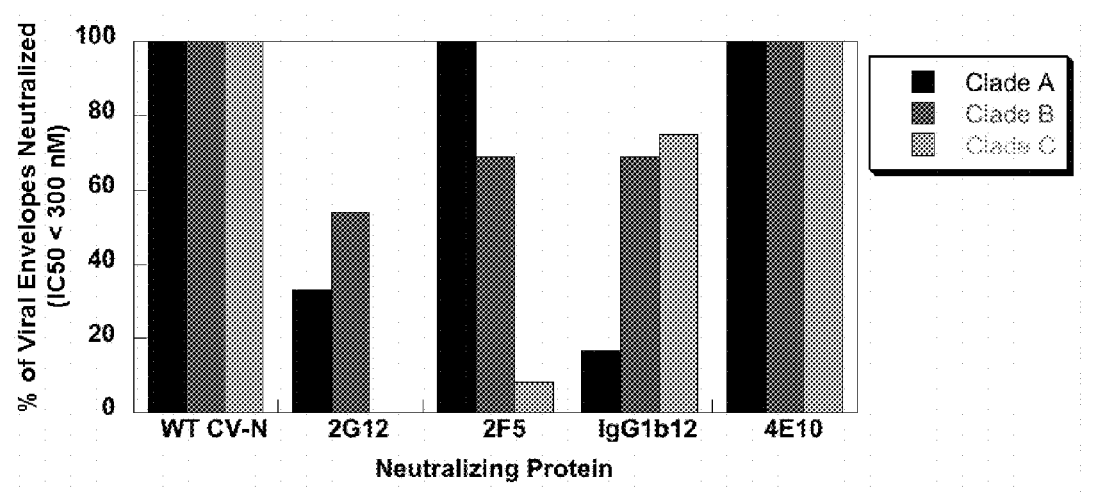

One of the most difficult obstacles in developing HIV neutralizing monoclonal antibodies (NAbs) is their lack of cross-clade reactivity. Most NAbs effectively neutralize viruses from one or two clades, but often are not effective against other clades. It is important for a potential therapeutic to be effective against as broad a range of viruses as possible. As shown in the data above, in the case of WT CVN and the dimeric mutants in accordance with the current invention, all 33 of the HIV pseudoviruses were neutralized with IC$_{50}$s less than 300 nM. A summary of this data is provided in FIG. 5. Only the 4E10 NAb was as cross-clade reactive, while 2G12 and 2F5 were not effective at neutralizing clade C viruses, and IgG1b12 was not effective against clade A viruses.

Figure 6:
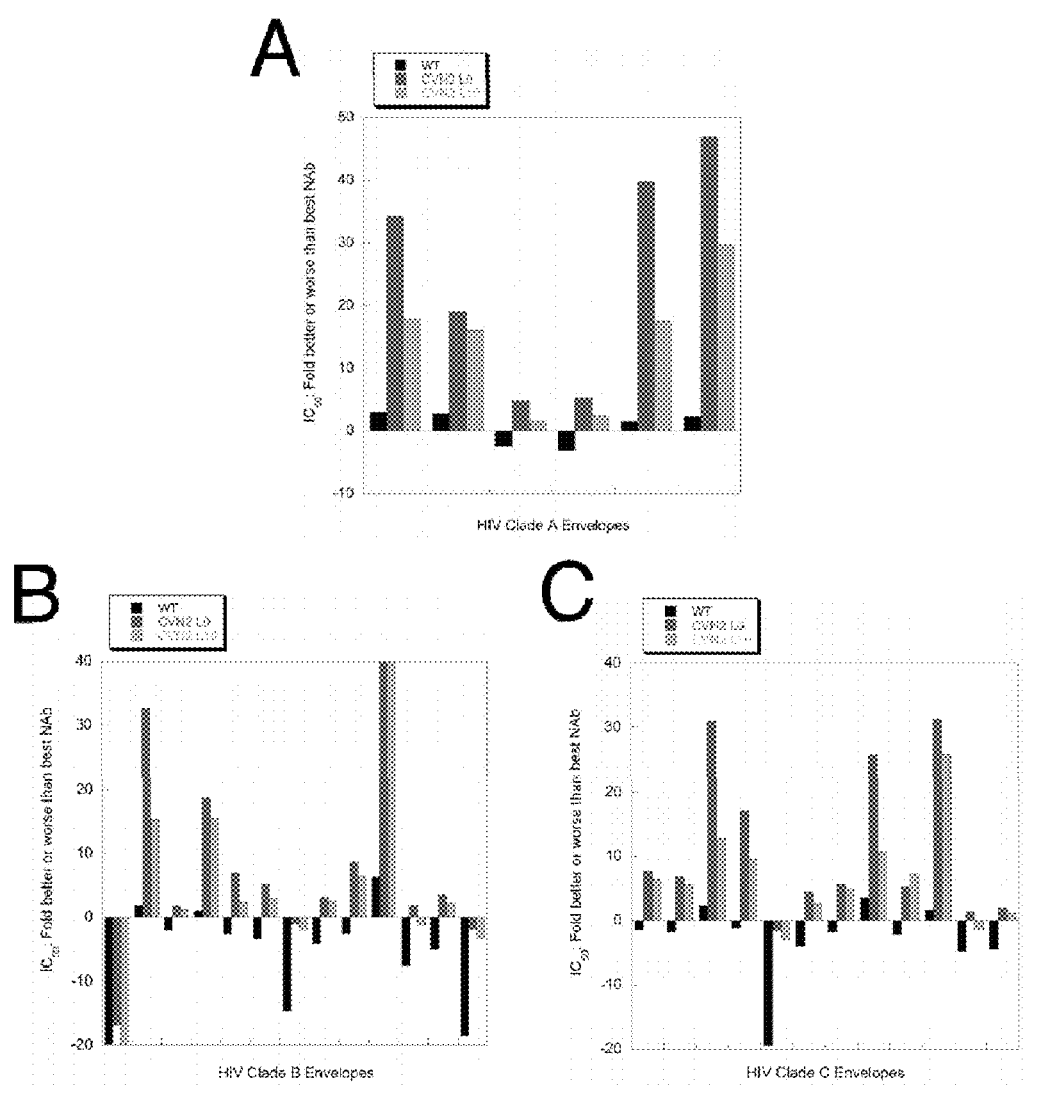

In addition to the broad cross-clade reactivity of WT CVN and the CVN$_2$ variants, the overall efficacy of the CVN proteins was compared to the NAbs. To simplify the analysis, the NAb with the lowest IC$_{50}$ for each individual envelope was chosen, and WT CVN, CVN$_2$ L0, and CVN$_2$ L10 was compared to that variant, as shown in FIG. 6. This comparison indicates that the engineered CVNs in accordance with the current invention are effective in comparison with the best of the broadly neutralizing antibodies for each strain. For many strains, WT CVN is less effective than the best NAb, as indicated by bars with negative values. However, by dimerizing the protein, the efficacy of neutralization was increased and new variants were generated that exhibit better neutralization than the best NAb against a given HIV strain. In fact, CVN$_2$ L0 is better at neutralizing HIV than the best NAb for every virus tested except for 4 out of 31 cases (2 of the 33 viruses did not have corresponding NAb data). Although it is only moderately more effective against some strains, CVN$_2$ L0 is at least 5-fold better than the best NAb against 19 out of 31 envelopes and at least 10-fold better against 11 envelopes. Additionally, CVN$_2$ L0 has an IC$_{50}$ 215-fold lower than the NAbs in one case (clade B, TRJ04551.58).

Figures 7, 8:
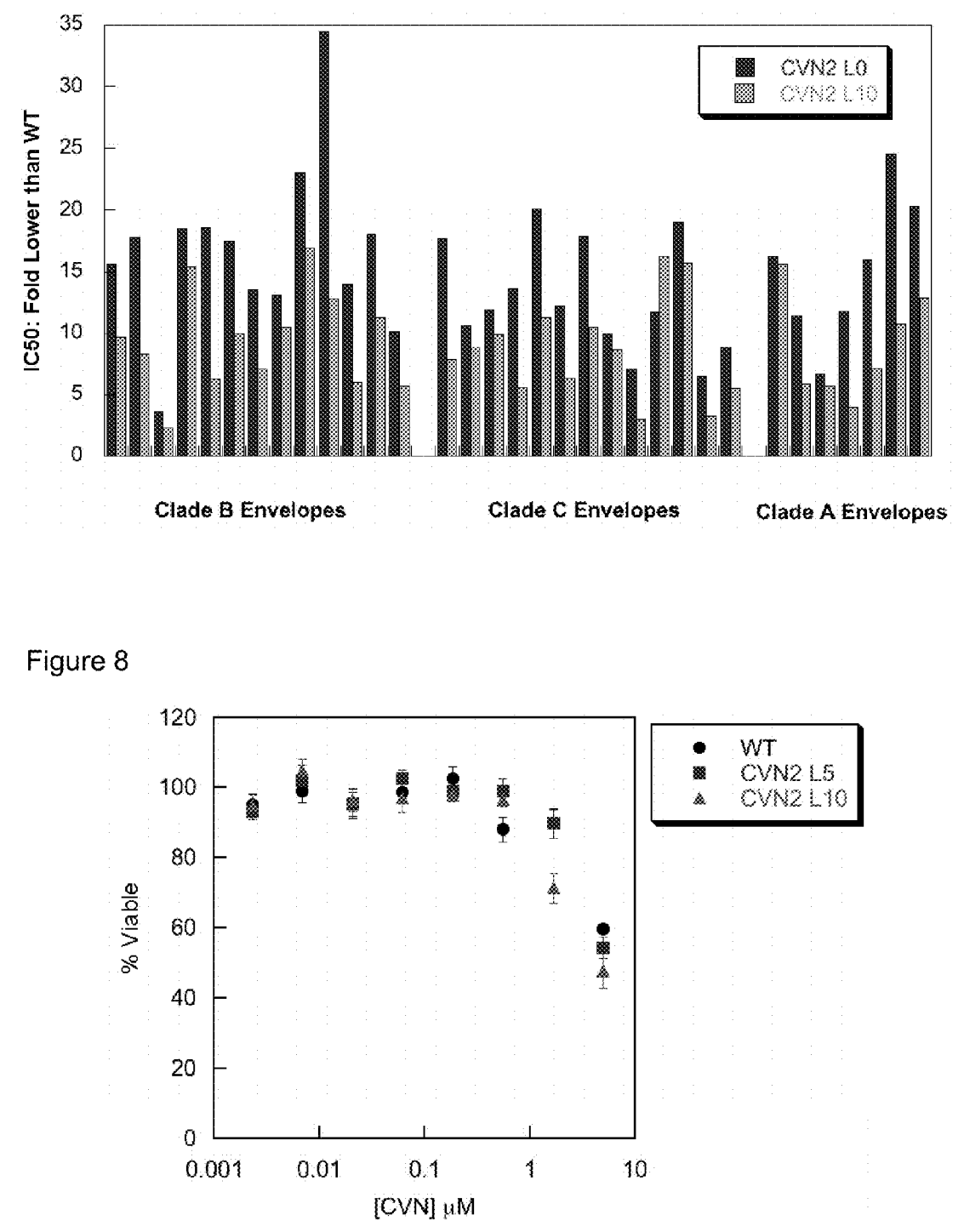

In summary, through dimerization, a variant has been created that is not only broadly cross-clade reactive, but is also more effective at neutralizing HIV-1 than the commonly studied NAbs. Similar to the results from neutralization assays on SC422661.8, the cross-clade data indicate that the dimerized variants are significantly more effective at neutralizing various strains of HIV-1 than WT CVN, as shown in FIG. 7. Specifically, CVN$_2$ L0 neutralized with a lower IC$_{50}$ than CVN$_2$ L10 in 32 out of 33 cases, and CVN$_2$ L10 neutralized with a lower IC$_{50}$ than WT in all 33 cases.

Cell Viability Assays.

An alternative explanation to the HIV neutralization assay data is that CVN is not in fact neutralizing HIV, but instead killing the host cell. In this case, the cell would not express luciferase upon infection because its cellular machinery would be nonfunctional. To test this hypothesis, WT CVN, CVN$_2$ L5, and CVN$_2$ L10 were each checked for toxicity against Tzm-Bl cells using an XTT cell proliferation assay. Concentrations up to 25-fold higher than the highest concentration used in the HIV neutralization assays were tested. The results indicate that at the concentrations relevant for the neutralization assays, CVN and the CVN$_2$ variants are not toxic as shown in FIG. 8. Limited toxicity both by the XTT assay as well as visual inspection of the cells at protein concentrations above 1 μM was observed. This result is consistent with published reports and indicates the activity of the engineered lectins of the current invention against HIV is in fact neutralization of the virus and not toxicity to the host cell. (See, e.g., Esser, M. T., et al., *J Virol*, 73, 4360-71, 1999, the disclosure of which is incorporated herein by reference.)

Mouse Toxicity.

Single subcutaneous injections containing various doses of WT CVN or CVN$_2$ L0 were injected into mice to determine the acute toxicity of the proteins in vivo. The mice were monitored over seven days for various signs of illness or toxicity according to an approved animal handling protocol. It was found that the mice could tolerate doses much higher than the expected therapeutic dose for both WT and CVN$_2$L0. The LD$_{50}$ (the dose which is toxic to half of the animals tested) was approximately 100 mg/kg for both WT and CVN$_2$L0.

Discussion

In accordance with the current invention, dimeric and trimeric CVN variants were successfully engineered that have significantly enhanced anti-HIV activity compared to WT CVN. These variants show excellent cross-clade and cross-strain reactivity and are more effective at neutralizing HIV than the most broadly neutralizing HIV antibodies.

Although not to be bound by theory, it is believed that differences in domain swapping may lead to an increase in efficacy. Previous reports have been divided about this issue, and because of the meta-stable state of domain-swapped WT, it has to-date been difficult to assay the dimerized form. The current invention provides variants, however, that are covalently linked at their termini, and as such have a much higher local concentration of CVN and therefore may be more stable as a domain-swapped dimer, even at physiological temperatures. Additionally, for variants with short linker lengths, the link may force a domain-swapped structure and may sterically hinder a monomeric-like form. An image of the dimeric CVN in accordance with the current invention is provided as FIG. 2.

Figure 9:
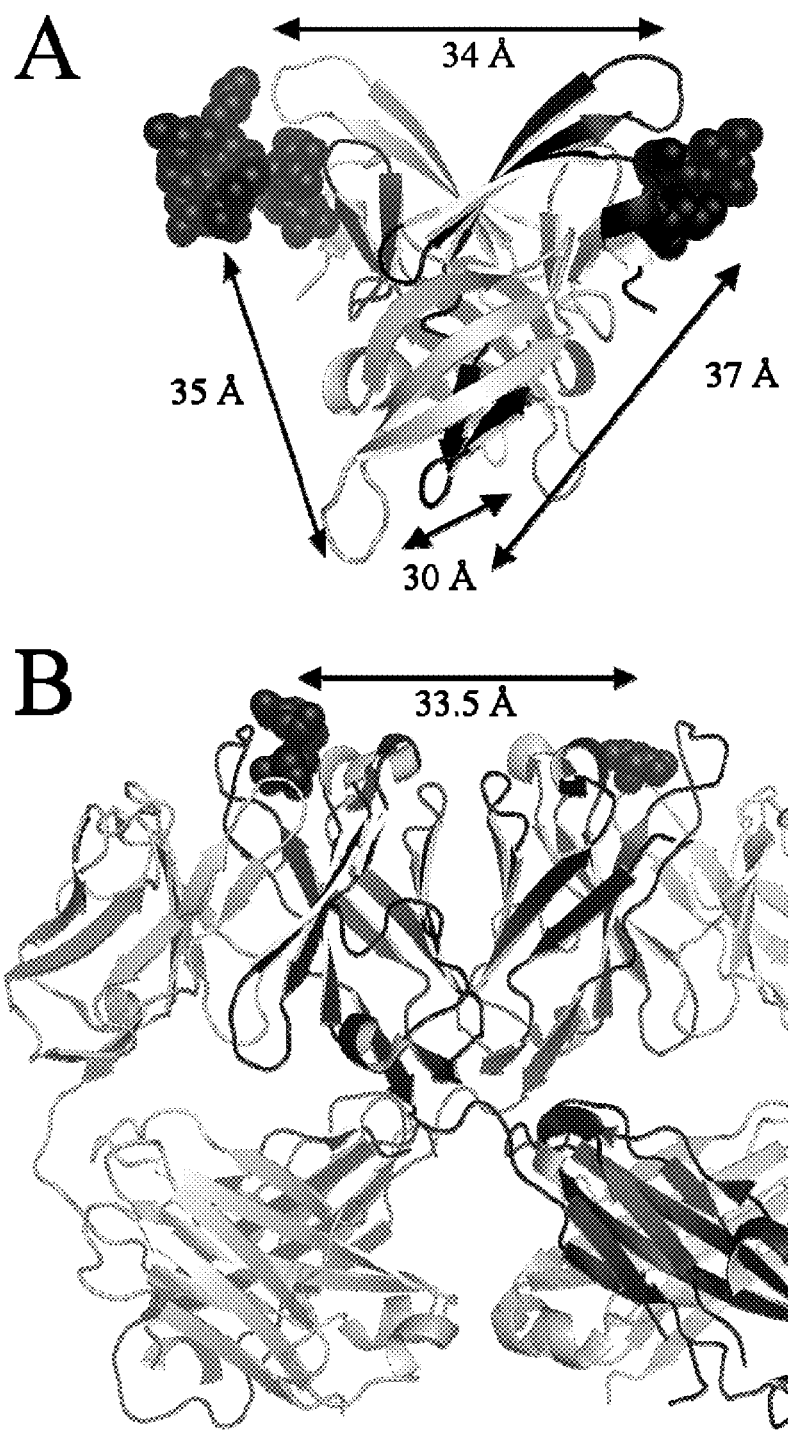
FIG. 9 provides carbohydrate binding site spacing in CVN and the 2G12 anti-HIV Fab. (A) Each of the four carbohydrate binding sites in the WT CVN crystal structure ($P4_12_12$ space group) is approximately 30 to 40 Å from the other sites. (B) The 2G12 Fab, which is specific to carbohydrates on gp120 and is broadly neutralizing, has an unusual domain-swapped form in the crystal structure. This domain-swapping rigidifies the carbohydrate binding sites with respect to each other and holds them approximately 35 Å apart. The carbohydrates in both structures are shown as black space filling models.

In addition to potential differences in domain swapping, the simple increase in carbohydrate binding sites may increase the avidity of the CVN-gp120 interaction. WT CVN itself has a very high affinity for gp120 but an increase in avidity in the CVN$_2$ variants may provide an extra force to prevent possible dissociation and escape of the virus. An alternate mechanism for increased neutralization is that the CVN$_2$s, with binding sites that are further apart than in WT CVN, are able to crosslink glycosylation sites on a single gp120 or crosslink multiple gp120 subunits on an envelope spike or, less likely, multiple spikes. This cross-linking would sterically hinder more gp120 subunits from binding to CD4 than would be blocked by WT CVN, thus decreasing the IC$_{50}$. An interesting note is that in the domain-swapped structure of WT CVN, every pair of carbohydrate binding sites is approximately 30 to 40 Å apart, as shown in FIG. 9. The neutralizing antibody 2G12, which also binds the glycosylation site on gp120 and is also domain-swapped, has carbohydrate binding sites that are also approximately 35 Å apart. (See, Calarese, D. A., et al., *Science*, 300, 2065-71, 2003, the disclosure of which is incorporated herein by reference.) One possibility is that by stabilizing the domain-swapped structure of CVN, the carbohydrate binding sites of the CVN$_2$ variants are optimally positioned to interact with gp120 and neutralize the virus.

While the addition of a second CVN molecule increases the efficacy of HIV neutralization significantly, the addition of a third CVN repeat (CVN$_3$) does not significantly increase it further. This result implicates domain-swapping, because if increased domain-swapping is involved, an unpaired, third CVN may not significantly increase the neutralization. Alternatively, due to the close proximity of the N- and C-termini in the WT structure and their proximity to the low affinity carbohydrate binding site, the third CVN molecule may sterically prohibit access to some of the carbohydrate binding sites in the molecule, rendering those sites nonfunctional and therefore not conveying any additional effect.

WT CVN and the CVN$_2$ molecules show excellent cross-clade and cross-strain reactivity. This property is promising for the development of these or other variants for therapeutic use as they can be used potentially throughout the world. In addition, CVN variants could be used in combination therapy to direct gp120 evolution toward decreased glycosylation. Glycosylation itself has been shown to be important in the folding and function of viral glycoproteins and in the case of HIV, deglycosylation of gp120 diminishes the binding to CD4, making the virus less infective. (See, Vigerust, D. J. & Shepherd, V. L., *Trends Microbiol*, 15, 211-8, 2007; Fenouillet, E., et al., *J Virol*, 64, 2841-8, 1990; and Montefiori, D. C., et al., *Proc Natl Acad Sci USA*, 85, 9248-52, 1988, the disclosures of each of which are incorporated herein by reference.) Alternatively, deglycosylation of gp120 could merely reveal more protein epitopes that can be recognized by the adaptive immune system, allowing our own bodies to fight off infection more effectively.

Exemplary Embodiment 2

Lectin Oligomerization on Other Viral Neutralization

Although CVN has long demonstrated significant utility at preventing HIV infections, it is only moderately active against the following enveloped viruses: influenza, Ebola (Ebo-Z), herpes simplex virus-1, Epstein-Barr virus, human herpes virus-6, and BVDV (a surrogate for hepatitis C). (See, Barrientos, L. G., et al., *Structure*, 12:1799-1807, 2004; Barrientos, L. G., et al., *Antiviral Res*, 58:47-56, 2003; and O'Keefe, B. R., et al., *Antimicrobial Agents & Chemo*, 47(8): 2518-2525, 2003, the disclosures of each of which are incorporated herein by reference.)

The glycoprotein GP1,2 present on the surface of Ebola virus particles displays oligosaccharides that are similar to those found on HIV's gp120; however, CVN's EC$_{50}$ for HIV is 0.1 to 5 nM (depending on the strain), while its EC$_{50}$ for Ebola (Ebo-Z) is 100 nM (i.e., it is 20 to 1,000-fold less effective against Ebola than it is against HIV). (See, e.g., Barrientos, L. G. & A. M. Gronenborn, *Mini-Rev. in Med, Chem.* 5:21-31, 2005, the disclosure of which is incorporated herein by reference.) The EC$_{50}$ indicates the concentration of CVN that is required to inhibit virus-induced cell death by 50%.

CVN also displays antiviral activity against most strains of influenza examined. (See, e.g., O'Keefe, B. R., et al., 2003, cited above.) CVN displayed anti-influenza EC$_{50}$ values that ranged from 5 ng/mL to 1.3 µg/ml when it was tested against a battery of strains that included seven types of influenza A (such as Sydney/05/97 (H3N2), Victoria/3/75 (H3N2), Mem/8/99 (H3N2), Mem/2/99 (H3N2), Beijing/262/95 (H1N1), Shangdong/09/93, and Shangdong/09/93-NIR—a neuraminidase-inhibitor resistant strain) and six strains of influenza B (Hong Kong/5/72, Yamanashi/166/98, Mem/3/99, Beijing/184/93, Sichuan/379/99, and Lee/40). (See, e.g., O'Keefe, B. R., et al., 2003, cited above.) CVN was able to neutralize many different strains of influenza in whole virus studies (−2.6 to −5.4 Δ log$_{10}$ in viral titers). (See, e.g., O'Keefe, B. R., et al., 2003, cited above.) CVN binds hemagglutinin (HA) in a concentration-dependent manner, and CVN's ability to bind HA is inhibited by free oligomannose in a concentration-dependent manner. (See, e.g., O'Keefe, B. R., et al., 2003, cited above.)

It is thought that the reason why CVN only has moderate activity against those other enveloped viruses most likely has to do with the density and/or the specific arrangement of the oligosaccharides that decorate those virus particles. (See, e.g., O'Keefe, B. R., et al., 2003, cited above.) In support of that notion, it has been shown in isothermal titration calorimetry studies that CVN's ability to bind to different glycoproteins is proportional to the amount of high-mannose oligosaccharides that decorate their surfaces. (See, Shenoy, S. R., et al., *J. of Pharmacology & Exp. Therapeutics,* 297(2):704-710, 2001, the disclosure of which is incorporated herein by reference.)

As previously discussed, by engineering chimeric multimers of CVN, the number and spacing of binding sites can be engineered in a controlled manner. Accordingly, these engineered multimers of CVN show the potential for stronger interactions with both virus particles that display a lower mannose density on their surface and also particles whose mannose units are farther away from the critical hot spots involved in virus—host cell fusion. Accordingly, studies were conducted to investigate the effects of engineered multimerization in accordance with the current invention on cyanovirin—N's broader antiviral activity.

Viral Neutralization of Vaccinia Virus

In addition to testing the efficacy of the engineered CVN lectins for HIV neutralization, the variants have also been tested against the vaccinia virus, a small pox model. The molecules described above were tested in duplicate in a spread assay at 500 nM and 250 nM.

All the CVN variants engineered in accordance with the current invention had similar inhibitory effects at 500 nM and at 250 nM. $CVN_2$ L0 was better than $CVN_2$ L10 (50% inhibition vs. ~30%). However, for whatever reason, in a few of the wells the cells lifted up, preventing a plaque count (the cells in both samples of WT CVN 250 nM lifted preventing a result for CVN at that concentration). This data indicates that the engineered CVN variants demonstrate increased potency in view of not just HIV, but also against a model pox virus, indicating that the variants in accordance with the current invention are more generally active against other enveloped viruses.

Viral Neutralization of Influenza Virus

Figure 10:
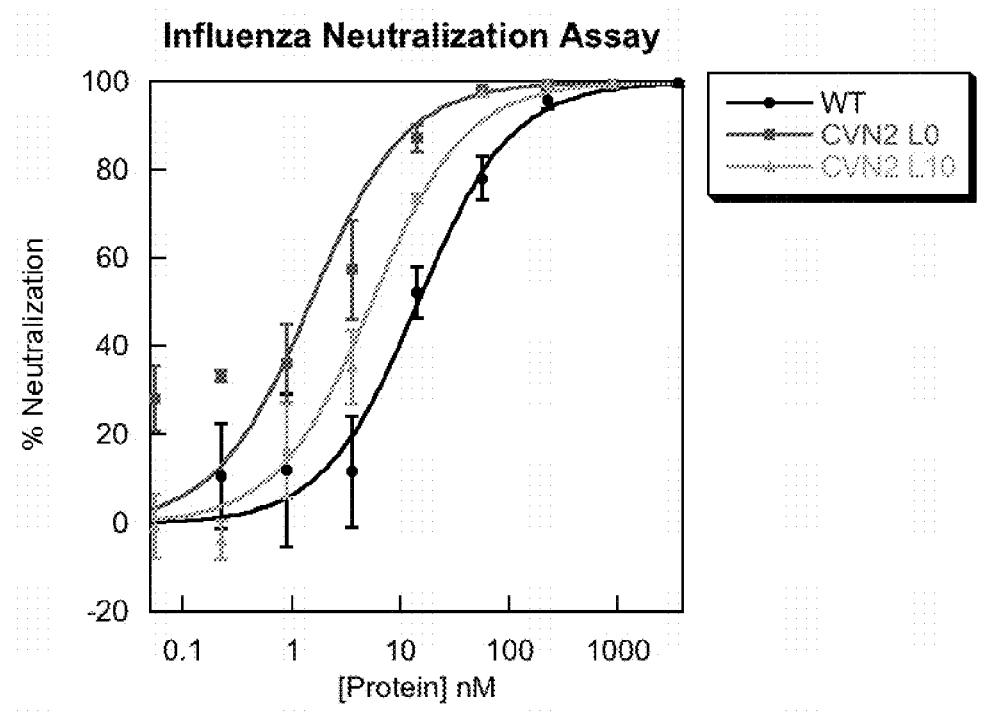
FIG. 10 provides data that CVN dimers show enhanced neutralization of influenza strain x31 (H3N2). $CVN_2$ L0 shows over 9-fold increase in influenza neutralization as compared to wild-type CVN, while $CVN_2$ L10 shows almost 3-fold increase in efficacy.

In addition to investigating the ability of the engineered CVN lectins in accordance with the current invention to neutralize HIV and the vaccinia virus, the ability to neutralize the influenza virus was also studied. A summary of the results is provided in FIG. 10. (The influenza assays were performed in accordance with the method described above with regard to the HIV neutralization assays, so the more the curve is shifted to the left, the "better" it is at neutralizing.) As shown, the CVN variants of the current invention show substantially greater potency at neutralizing the influenza virus.

The combined results of the potency studies against HIV, vaccinia and influenza collectively indicate that the increase in efficacy for the multimeric variants in accordance with the current invention applies to all or most enveloped viruses. The increased neutralization exhibited by these linked CVN variants and the broad cross-strain reactivity indicates clearly that the inventive CVN variants hold promise for the future therapeutic utility of these and other engineered CVN variants. In addition, since the human host cell controls the structure of the oligosaccharides (sugars) that are added to the surface of new strains of influenza when they arise, multimeric CVN in accordance with the current invention has the potential to be effective against new strains of influenza.

Exemplary Embodiment 3

Lectin Oligomerization Structural Studies

As previously discussed, CVN exists in solution both as a monomer and a domain-swapped dimer, as shown in FIG. 1. The monomer consists of two pseudo-domains that display high sequence homology. The first domain contains residues 1-39 and 90-101, and the second domain contains residues 39-89. (See, Bewley, C. A., et al., *Nat Struct Biol,* 5, 571-8, 1998, the disclosure of which is incorporated herein by reference.) CVN includes a three-stranded antiparallel β sheet and a β hairpin in each pseudo-domain. The pseudo-domains are connected through two helical turns. CVN also contains two native disulfide bridges: between residues 8 and 22, and between residues 58 and 73. These two disulfide bridges are located near each end of the molecule and anchor the first strand of the β sheet to the second strand. The dimer contains the same topology, but is domain-swapped at residues 51-53. (See, Yang, F., et al., *J Mol Biol,* 288, 403-12, 1999, the disclosure of which is incorporated herein by reference.) In this case, the first domain of one chain (A) forms a "monomer-like" structure with the second domain of the other chain (B') in an almost symmetric domain swapping, as shown in FIG. 1B. The two quasi-monomers can sample different orientations relative to each other due to the flexibility of the domain-swap region, and the orientation appears to be pH dependent in crystal structures. (See, Botos, I. & Wlodawer, A., *Cell Mol Life Sci,* 60, 277-87, 2003, the disclosure of which is incorporated herein by reference.)

As shown in FIG. 1A, CVN contains two carbohydrate-binding sites of differing affinities for α1-2 mannose: one at each end of the molecule. The high affinity site, located distal from the N- and C-termini, has a dissociation constant in the low nanomolar range, whereas the lower affinity site has approximately 10-fold weaker affinity. (See, Bewley, C. A. & Otero-Quintero, S., *J Am Chem Soc,* 123, 3892-902, 2001, the disclosure of which is incorporated herein by reference.) To date, no crystal structures have been solved of CVN with carbohydrate bound to the high affinity site. Although not to be bound by theory it is believed that it is due to crystallographic packing, which obstructs this binding site. However, numerous structures have been solved with carbohydrate bound to the low affinity sites, and these structures are very similar to the NMR structures. (See, Botos, I., et al., *J Biol Chem,* 277, 34336-42, 2002; and Fromme, R., et al., *Biochemistry,* 46, 9199-207, 2007, the disclosures of each of which are incorporated herein by reference.)

In solution, CVN exists mainly as a monomer, and NMR structures have been solved of monomeric CVN, both free and bound to carbohydrates. However, all crystal structures of the wild-type (WT) protein to date have yielded domain-swapped structures, a proposed artifact of the crystallographic process. (See Botos, I., et al., *J Biol Chem,* 277, 34336-42, 2002; Barrientos, L. G., et al., *Structure,* 10, 673-86, 2002; and Botos, I., et al., *Biochem Biophys Res Commun,* 294, 184-90, 2002, the disclosures of each of which are incorporated herein by reference.) The domain-swapped form is metastable in solution and rapidly coverts to the more stable monomer at physiological temperatures, but is stable for long periods of time at low temperature. However, in the crystallographic conditions of high protein concentration, extreme pH, and high precipitant concentration, the equilibrium is shifted from the purified monomer to the crystallized dimer. Solution structures of isolated dimer are similar to those solved using crystallography. Various constructs have been engineered to modulate the domain-swapping, including variants that preferentially form monomers and those that form dimers in solution. (See Kelley, B. S., et al., *J Am Chem Soc,* 124, 3210-1, 2002; and Barrientos, L. G., et al., *Structure,* 12, 1799-807, 2004; the disclosures of each of which are incorporated herein by reference.) One of these variants, a five-fold mutant including the P51G mutation, which stabilizes the monomeric state, was solved recently as a monomer using crystallography. (Fromme, R., et al., *Biochemistry*, 46, 9199-207, 2007, the disclosure of which is incorporated herein by reference.)

Although a great deal of work has been done to change the preference for monomeric or dimeric protein, there is still a controversy about the effect of dimerization on the antiviral activity of CVN. Because WT domain-swapped dimer converts to monomer during the course of a viral neutralization assay, it is difficult to assay the effect of dimerization directly. Therefore, various mutants have been generated to try to elucidate the relationship between oligomerization and activity. Kelley et al. created an obligate domain-swapped dimer by deleting one of the residues in the domain-swap region and observed a 3.5-fold reduction in the concentration at which half of the viral particles are neutralized ($IC_{50}$) of HIV fusion. They also showed a similar 3.5-fold reduction in the $IC_{50}$ for purified WT dimer. (See, Kelly, B. S., et al., 2004, cited above.) However, Barrientos et al. tested WT monomer, WT dimer, and various engineered mutants and found that regardless of the oligomerization state, all molecules had essentially the same activity against both HIV and Ebola Zaire. (See, Barrientos, et al., 2004, cited above.) Differences in the incubation time and assay conditions could explain the discrepancy, but the question still remains whether dimeric CVN is more effective at neutralizing viruses than monomeric CVN.

To confirm the mechanism for the increased efficacy that is seen for the dimeric and trimeric variants in accordance with the current invention, studies of the structures of the variants were conducted. Toward this goal, the crystal structures of $CVN_2$ L0, $CVN_2$ L1, and $CVN_2$ L10 were solved to determine whether simple structural differences account for the changes in activity.

Methods

Protein expression and purification. $CVN_2$ L0, $CVN_2$ L1, and $CVN_2$ L10 were expressed and purified as described in Exemplary Embodiment 1. After gel filtration, the proteins were concentrated using 5,000 MWCO Amicon Ultra concentrators (Millipore) to 25-30 mg/mL.

Crystallization.

Crystallization conditions were set up using a Mosquito automated nanoliter pipettor (TTP Labtech) in the Molecular Observatory at Caltech. Screening was done with 480 conditions in 96-well sitting drop plates using 0.3×0.3 µL drops. Each protein crystallized under many conditions, and suitable crystals were found for data collection from these initial screens. The best diffracting $CVN_2$ L0 crystals were grown in 0.1 M sodium HEPES pH 7.5, 0.8 M potassium dihydrogen phosphate, 0.8 M sodium dihydrogen phosphate. $CVN_2$ L1 data sets were collected on crystals from 0.1 M phosphate-citrate pH 4.2, 2.0 M sodium/potassium phosphate ($P3_221$ structure) and from 0.1 M CHES pH 9.5, 0.2 M lithium sulfate and 1 M potassium/sodium tartrate ($P4_12_12$ structure). The $CVN_2$ L10 data set was collected on a crystal grown in 0.2 M sodium fluoride and 20% PEG-3350.

Data Collection and Refinement.

All crystals except the CHES $CVN_2$ L1 crystal were cryoprotected in TMP oil. $CVN_2$ L1 crystals grown in the CHES/tartrate condition were cryoprotected using the reservoir condition including 20% glycerol. Data for the $CVN_2$ L0 and L1 structures were collected using a MicroMax-007HF X-ray generator with an RAXIS IV++ detector (Rigaku Corp.). The $CVN_2$ L10 data set was collected on the 12-2 beam line at the Stanford Synchrotron Radiation Lightsource (SSRL). All data were processed using CrystalClear (Rigaku Corp.) and Mosflm. (See, Leslie, A. G. W., *Joint CCP4+ESF-EAMCB Newsletter on Prot. Crystallography* 26, 1992, the disclosure of which is incorporated herein by reference.)

The indexed and scaled data were further evaluated using CCP4i. (See, *Acta Crystallogr D Biol Crystallogr*, 50, 760-3, 1994, the disclosure of which is incorporated herein by reference.) The molecular replacement for data sets indexed to the $P3_221$ space group were done using 3EZM as the starting model. (See, Yang, F., et al., *J Mol Biol*, 288, 403-12, 1999, the disclosure of which is incorporated herein by reference.) The molecular replacement of the $CVN_2$ L1 data in the $P4_12_12$ space group was done using 2Z21 as the starting model. (See, Fromme, R., et al., *Biochemistry*, 46, 9199-207, 2007, the disclosure of which is incorporated herein by reference.) Phaser version 1.3.3 was used for the molecular replacement. (See, McCoy, A. J., et al., *Acta Crystallogr D Biol Crystallogr*, 61, 458-64, 2005, the disclosure of which is incorporated herein by reference.) Further refinement was done using Coot and Refmac and omit maps were created using CNS. (See, e.g., Emsley, P. & Cowtan, K., *Acta Crystallogr D Biol Crystallogr*, 60, 2126-32, 2004; Murshudov, G. N., et al., *Acta Crystallogr D Biol Crystallogr*, 53, 240-55, 1997; Brunger, A. T., *Nat Protoc*, 2, 2728-33, 2007; Brunger, A. T., et al., *Acta Crystallogr D Biol Crystallogr*, 54, 905-21, 1998, the disclosure of each of which are incorporated herein by reference.) Figures were made using PyMOL. (See, DeLano, W. L. The PyMOL Molecular Graphics System, http://www.pymol.org, DeLano Scientific, Palo Alto, Calif., 2008, which is incorporated herein by reference.)

Results

Crystallization.

$CVN_2$ L0, $CVN_2$ L1, and $CVN_2$ L10 were chosen for structural characterization. As described in Exemplary Embodiment 1, $CVN_2$ L0 and $CVN_2$ L10 were the most active of the engineered dimers, while $CVN_2$ L1 was less active than $CVN_2$ L0 due to the single amino acid linker. Crystal structures of these proteins were therefore solved to determine whether any major structural differences could explain the changes in the HIV neutralization activity that are observed. All of the proteins were crystallized in 96-well plates with 0.6 µL drops. $CVN_2$ L0 crystallized in approximately 20 out of the 480 conditions tested. Most of these conditions contained sulfate or phosphate as the precipitant and low pH buffers, although the protein also crystallized well in 20% PEG 3350. $CVN_2$ L10 crystallized in similar conditions to $CVN_2$ L0, and crystals were observed in approximately 35 conditions. $CVN_2$ L1 crystallized in approximately 35 conditions as well, but in addition to crystal forms seen for $CVN_2$ L0 or $CVN_2$L10, new crystal forms were observed in high pH conditions. Approximately half of the crystal conditions for $CVN_2$ L0 were above neutral pH, while the $CVN_2$ L10 conditions were only about one-third above neutral pH. The structure for $CVN_2$ L1 was therefore determined from both a low pH condition ($P3_221$ space group) and a high pH condition ($P4_12_12$ space group). $CVN_2$L0 and $CVN_2$L10 structures were solved using the only well-diffracting crystals available, which were from low pH conditions ($P3_221$ space group).

Crystal Structure Refinement.

All of the $P3_221$ space group structures were solved using the domain-swapped WT structure 3EZM.pdb as the model for molecular replacement (see summary in Table 3, below). This WT structure was solved from the same space group, and the molecular replacement provided a good initial model. Further refinement on all structures yielded domain-swapped models that fit the density well. Omit maps were calculated for each of the structures, which agreed well with the models. The omit maps did not indicate any major differences for either the backbone or the side chains of the structure. Solvent molecules, including waters and sodium ions, were added to each structure when there were appropriate electron density and hydrogen bonding partners.

The structures solved from P3$_2$21 space group crystals contained only half of the CVN$_2$ dimer in the asymmetric unit, and the second tandem repeat of CVN was generated through crystallographic symmetry. However, because the two copies of CVN are covalently linked through a flexible polypeptide linker, this caused difficulty in the refinement. In order to properly model the termini as well as the linkage, the linker residues are at 50% occupancy. This is because half of the proteins are oriented in a way that the free termini are in a specific location, while the other half of the proteins have the linkage in that same location. The protein crystallized in both orientations with approximately the same frequency, resulting in symmetry with 50% occupancy of the termini.

In addition to the low pH structure, the CVN$_2$ L1 structure at high pH (P4$_1$2$_1$2 space group) was also determined (see Table 3, below). A molecular replacement with 3EZM.pdb was suboptimal, giving a solution and electron density map that did not correlate. However, replacement with a monomeric five-fold variant of WT CVN (2Z21.pdb) gave a model and map that were reasonable. Upon inspection of the map, it was clear that the structure was in fact domain-swapped, similarly to the P3$_2$21 structures. The structure model was modified to reflect the domain-swapping of the electron density, and solvent molecules were added.

To confirm that the crystallized protein in each case was in fact CVN$_2$ and not contamination from WT CVN, an SDS-PAGE gel was run on crystals grown in the same conditions as those the data sets were collected on. The crystals were rinsed to remove any non-crystallized protein before being denatured. The gel showed that all of the crystals were indeed CVN$_2$ with no WT contamination (data not shown), allowing for the conclusion that indeed only half of the molecule was present in the asymmetric unit in the P3$_2$21 space group cases and that it was reasonable to model in the linker at 50% occupancy.

CVN$_2$ L0 Structure.

Figure 11:
FIG. 11 provides a diagram of a $CVN_2$ L0 crystal structure compared to WT CVN. The $CVN_2$ L0 crystal structure (black) and domain-swapped WT CVN (3EMZ.pdb) (gray) have an RMSD of 0.239 Å. The structures are very similar with small deviations in the β strands and the domain swap area.

CVN$_2$ L0 is a domain-swapped dimer under low pH crystallographic conditions, see FIG. 11. Its structure is remarkably similar to WT CVN, with an RMSD of 0.239 Å. Although the refinement is not complete, it can be stated with certainty that there are no major disruptions of the structure by directly linking two CVNs together without a linker. There are, however, minor differences in the domain-swapped area compared to WT CVN.

Figure 12:
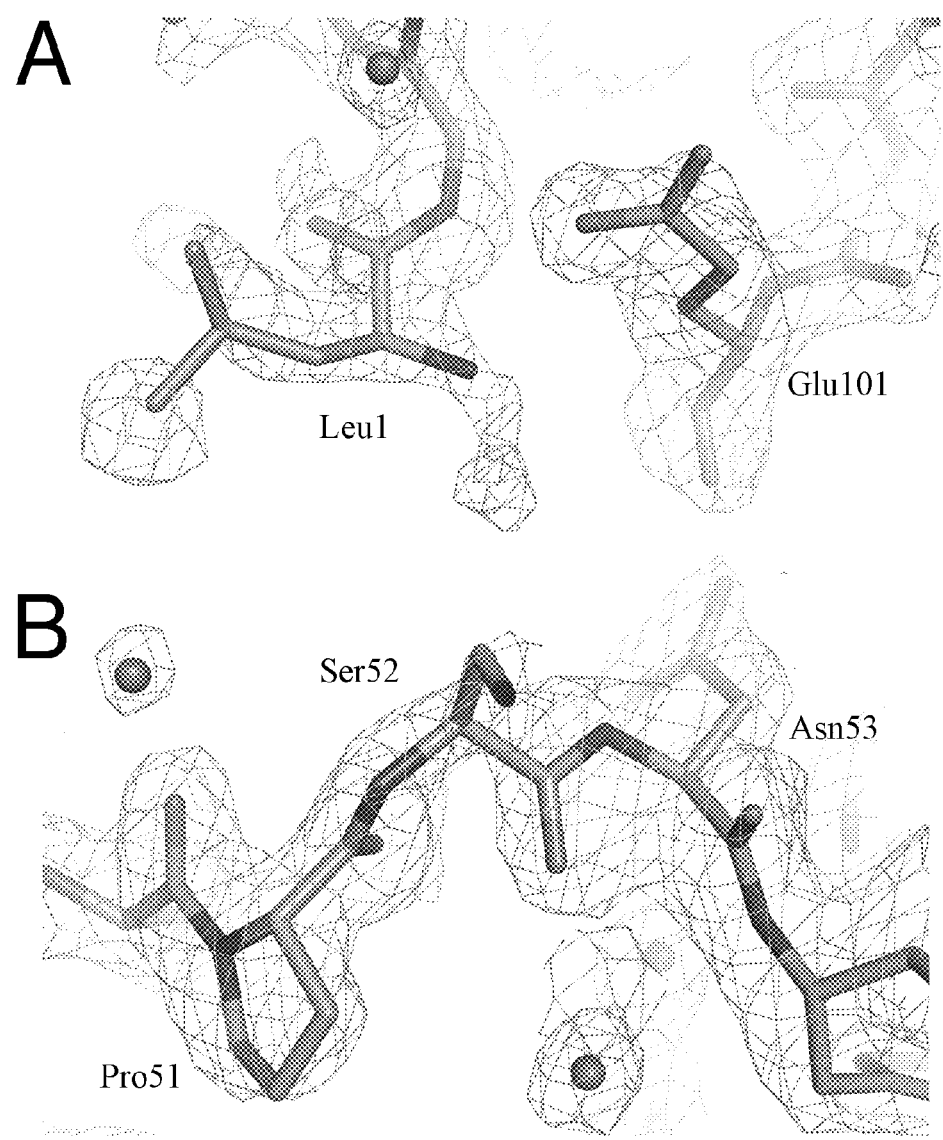
FIG. 12 provides a diagram of a $CVN_2$ L0 structure. Only half of the $CVN_2$ dimer was found in the asymmetric unit. The other half is generated through crystallographic symmetry, and the linker and free termini are each 50% occupied. The 2Fo-Fc electron density map is shown as light gray mesh. (A) The termini of $CVN_2$ L0 are not well defined. There is positive density where the linkage may occur. (B) $CVN_2$ L0 is domain-swapped in the crystal structure. The density in the swapped area is clear and definitive.

Because only one half of the CVN$_2$ L0 was in the asymmetric unit, as described above, the electron density at the termini is a composite from both the free and the linked termini. As shown in FIG. 12A, a view of the electron density fit to a free N- and C-terminus shows positive electron density between them, indicating the model does not fit well in this area. Although not to be bound by theory it is hypothesized that the free termini are in a significantly different conformation from the termini that are linked and that the electron density is a combination of these. Future rounds of refinement will be done to model both conformations separately at 50% occupancy in order to fit the experimental data.

In FIG. 12B it can clearly be seen from the electron density that CVN$_2$ L0 is a domain-swapped dimer under these conditions. Molecular replacement with a monomeric WT CVN resulted in density that also showed clear domain-swapping, indicating that model bias is not responsible for this density.

CVN$_2$ L1 Structures.

Figure 13:
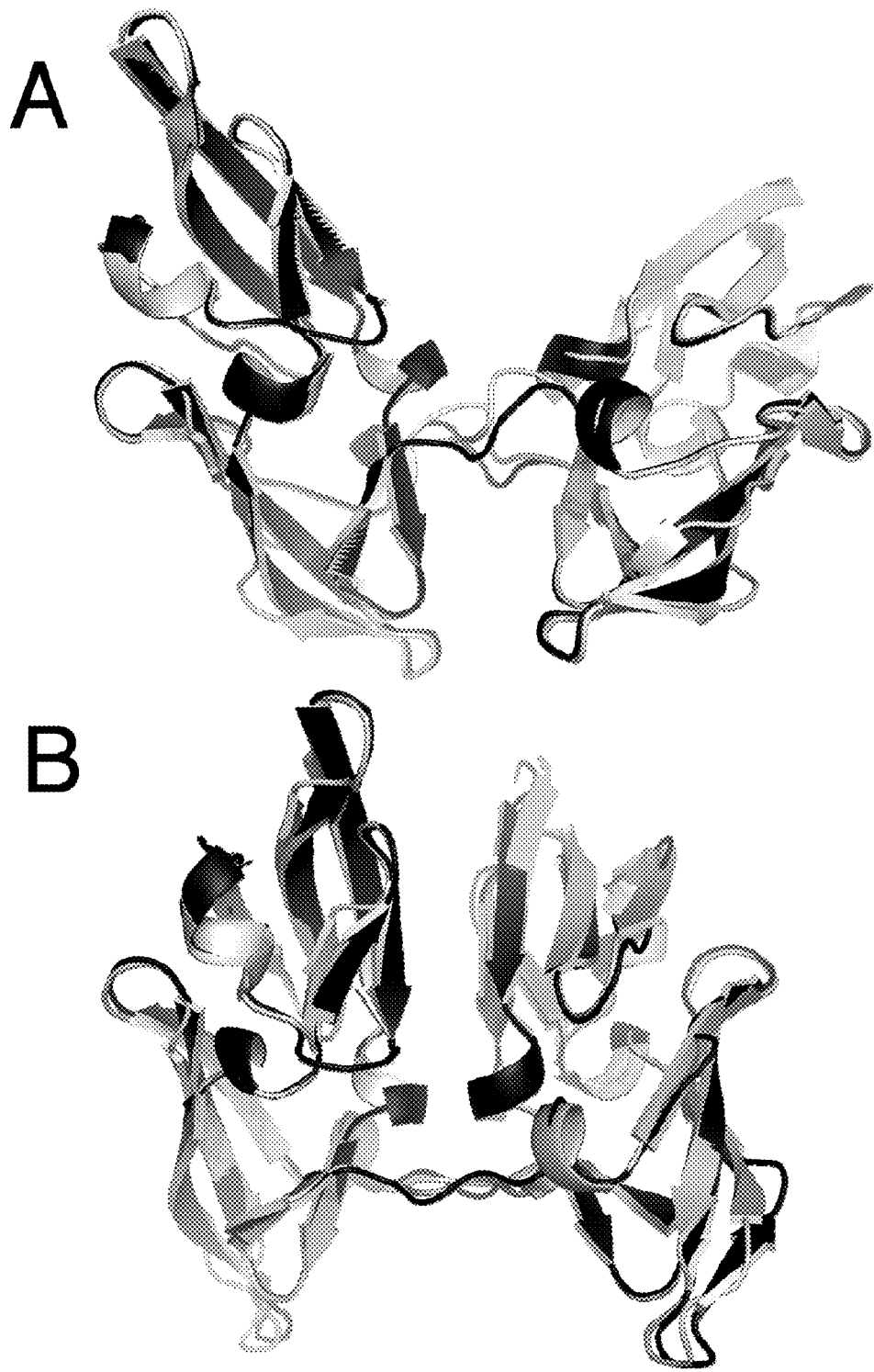
FIG. 13 provides diagrams of $CVN_2$ L1 crystal structures compared to WT CVN. $CVN_2$ L1 structures are shown in black and the WT CVN structures are shown in light gray. (A) $CVN_2$ L1 in the $P3_22_1$ space group, solved in low pH conditions, overlaid with domain-swapped WT CVN (3EZM.pdb). The RMSD of these structures is 0.283 Å, and the major differences are seen in the domain swap area. (B) $CVN_2$ L1 in the $P4_12_12$ space group, solved in high pH conditions, overlaid with domain-swapped WT CVN (1L5B.pdb). These structures have a 0.407 Å RMSD. The one residue linker can be seen in the structures in the domain on the left.

CVN$_2$ L1 crystallized with two major morphologies. Because of the difference in the shape of the crystals and because they were indexed to different space groups, two structures of CVN$_2$ L1: one from the P3$_2$21 space group and the other from the P4$_1$2$_1$2 space group were solved. Upon molecular replacement, it became clear that both structures were WT-like domain-swapped structures with slightly different orientations of the domains relative to each other, as shown in FIG. 13. It has been shown previously that WT CVN crystallizes in different space groups and different morphologies depending on the pH of the crystallization condition. (See, Botos, I. & Wlodawer, A., *Cell Mol Life Sci*, 60, 277-87, 2003, the disclosure of which is incorporated herein by reference.) This appears to be the case here as well.

The P3$_2$21 structure, solved from a low pH condition, is very similar to the WT low pH structure, with an RMSD of 0.283 Å. Like the other P3$_2$21 structures, there are minor deviations in the domain-swap area, but overall there are no major structural perturbations by linking two termini. The P4$_1$2$_1$2 also does not appear to be significantly different from WT CVN when compared to a structure solved at high pH, as shown in FIG. 13B. (See, Barrientos, L. G., et al., *Structure*, 10, 673-86, 2002, the disclosure of which is incorporated herein by reference.) The RMSD between WT CVN and the P4$_1$2$_1$2 is 0.407 Å. In this case as well, there are no major structural changes to CVN$_2$ L1 that would explain the vast increase in biological activity.

Figure 14:
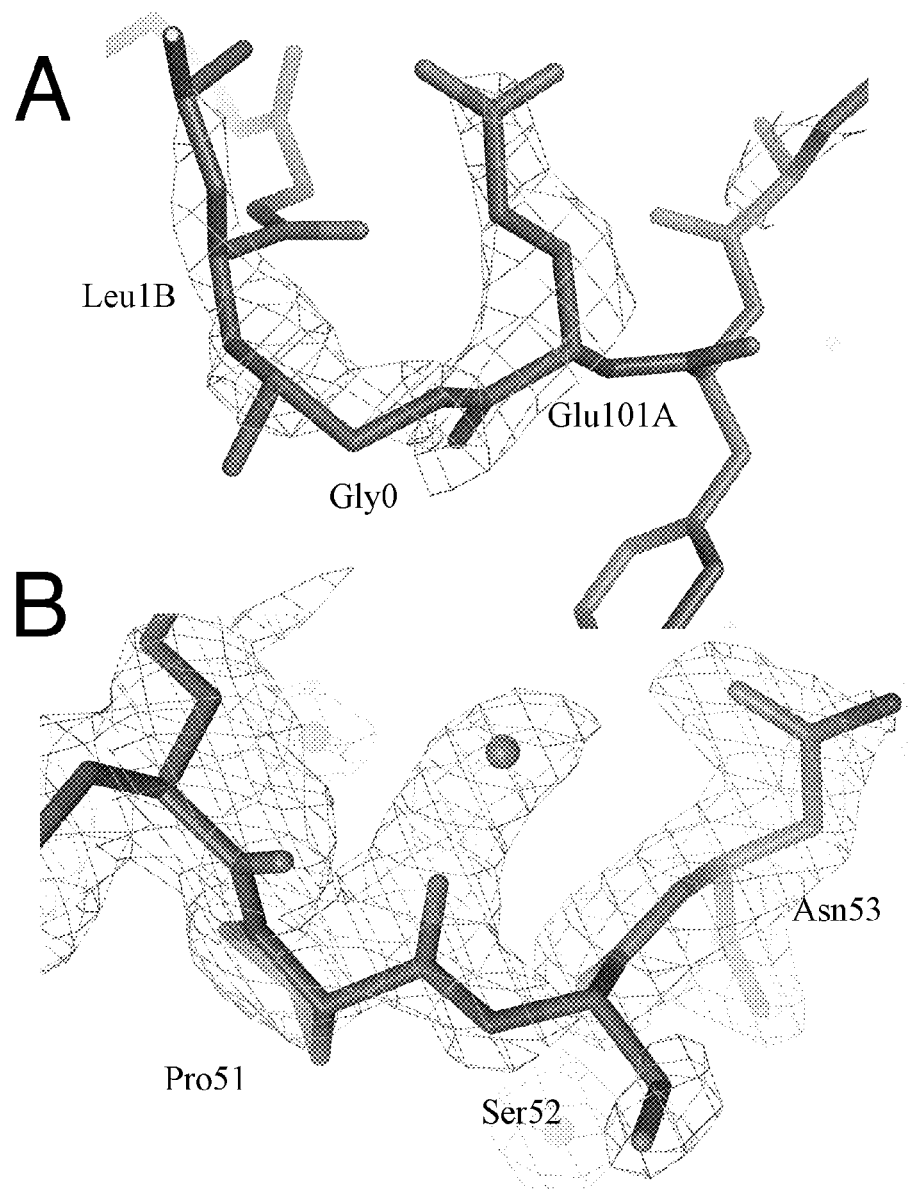
FIG. 14 provides a diagram of a $CVN_2$ L1 $P3_22_1$ structure. Only half of the $CVN_2$ molecule was in the asymmetric unit. The free termini and the linked termini are both represented with the same density, at 50% occupancy each. (A) The N- and C-termini of $CVN_2$ L1 with a 2Fo-Fc electron density map contoured at 1.0σ showing clear density for the single glycine residue linker. Gly0 shown in the figure is only 50% occupied. (B) The $CVN_2$ L1 in this crystal structure is clearly domain-swapped as evidenced by clear electron density in the domain swap region.

As shown in FIG. 14A, clear density was visible for a single glycine linker between the termini of the P3$_2$21 structure. However, due to the fact that only half of the molecule is in the asymmetric unit, the linker has been modeled in with 50% occupancy. Although not to be bound by theory it is believed that the free termini have significantly different conformations from the termini that are linked. Forty-five water molecules and two sodium ions were placed in the structure with high confidence.

Figure 15:
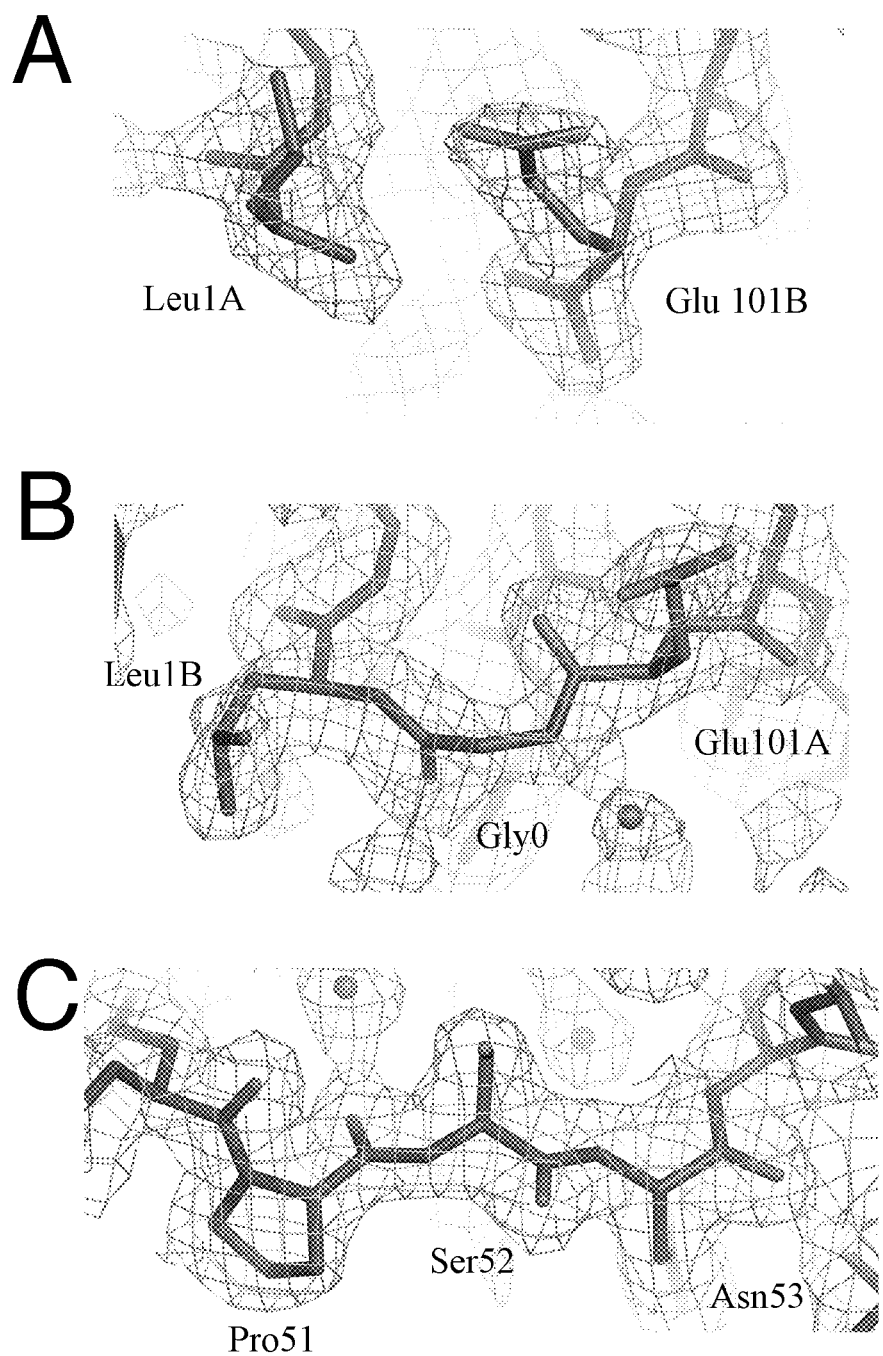
FIG. 15 provides a diagram of a $CVN_2$ L1 $P4_12_12$ structure. The entire $CVN_2$ L1 dimer was within the asymmetric unit in the $P4_12_12$ crystal structure. The free termini were clearly distinguishable from the linkage as determined by the 2Fo-Fc electron density contoured to 1.0σ. (A) The free N- and C-termini of CVN$_2$ L1. (B) The linked N- and C-termini of CVN$_2$ L1 and clear density for the single glycine linker. (C) Well defined density is seen in both chains for the domain swap residues 51 through 53.

In the P4$_1$2$_1$2 structure, 104 water molecules were added. There was also a CHES molecule near the high affinity carbohydrate binding site of one CVN domain, which broke the symmetry of the molecule, causing the entire CVN$_2$ L1 to be in the asymmetric unit, unlike the P3$_2$21 structures. The free termini and the linked termini were clearly distinguishable in the initial electron density map, and therefore, it was possible to model them separately, as shown in FIG. 15. In addition to different conformations for the linked residues, there was also clear density for the single glycine in the linker.

In both crystal forms, CVN$_2$ L1 forms a domain-swapped dimer similar to WT CVN, as shown in FIGS. 14B and 15C. The conformations of residues involved in the swap in the P4$_1$2$_1$2 structure are almost identical to the WT structure, but there are small differences in the conformations from the P3$_2$21 structure compared to WT. While these differences may be real, it is not expected that they fully explain the significant increase in activity of CVN$_2$ L1 over WT CVN in the neutralization assay.

Both CVN$_2$ L1 structures have unexpectedly high R$_{free}$ values (see Table 3, below). Omit maps on each structure indicate that there were no major problems with either the backbone or the side chains. Because the termini and the linkage are somewhat unstructured and the model is not perfectly matched to the electron density in this area, it is possible that there is some model bias. However, these small deviations should not have a significant impact on the overall structures. The addition of more water and solvent molecules may also decrease the R$_{free}$ and give more reasonable statistics.

TABLE 3

| | Crystallographic Statistics | | | |
|---|---|---|---|---|
| | $CVN_2$ L0 | $CVN_2$ L1 | $CVN_2$ L1 | $CVN_2$ L10 |
| Data Collection | | | | |
| Space Group | $P3_221$ | $P3_221$ | $P4_12_12$ | $P3_221$ |
| Cell Dimensions | | | | |
| a, b, c (Å) | 47.9, 47.9, 78.7 | 47.5, 47.5, 78.6 | 60.6, 60.6, 147.6 | 48.0, 48.0, 79.3 |
| α, β, γ (deg) | 90, 90, 120 | 90, 90, 120 | 90, 90, 90 | 90, 90, 120 |
| Resolution (Å)* | 2.0 (2.11-2.0) | 2.0 (2.11-2.0) | 2.1 (2.21-2.1) | 1.75 (1.84-1.75) |
| No. reflections | 42309 | 50188 | 206257 | 59304 |
| Unique reflections | 7456 | 7347 | 16878 | 11158 |
| $R_{merge}$ (%)* | 5.1 (22.8) | 3.7 (10.8) | 4.3 (27.6) | 10.3 (38.4) |
| $I/\sigma I$* | 23.6 (5.6) | 33.3 (13.5) | 42.9 (9.2) | 12.7 (4.2) |
| Completeness (%)* | 100.0 (100.1) | 99.9 (99.9) | 100.0 (100.0) | 100.0 (100.1) |
| Redundancy* | 5.7 (5.7) | 6.8 (6.7) | 12.2 (12.3) | 5.3 (5.2) |
| Refinement | | | | |
| Resolution (Å) | 23.9-2.0 | 28.4-2.0 | 27.1-2.1 | 36.8-1.75 |
| No. reflections | | | | |
| Working set | 6687 | 6642 | 15109 | 10060 |
| Test set | 341 | 340 | 851 | 528 |
| $R_{work}/R_{free}$ | 22.0/24.9% | 21.8/27.4% | 22.0/28.8% | 18.8/21.2% |
| No. atoms | | | | |
| Protein | 796 | 785 | 1567 | 823 |
| Solvent | 60 | 47 | 118 | 89 |
| B-factors | | | | |
| Protein | 31.2 | 31.0 | 32.4 | 19.3 |
| Water | 34.0 | 34.5 | 34.9 | 28.6 |
| R.m.s. deviations | | | | |
| Bond lengths (Å) | 0.012 | 0.011 | 0.011 | 0.011 |
| Bond angles | 1.375 | 1.307 | 1.215 | 1.351 |
| Ramachandran plot | | | | |
| Favored (%) | 89 | 90.2 | 88.3 | 98.2 |
| Allowed (%) | 11 | 9.8 | 12 | 10.8 |
| Generously allowed (%) | 0 | 0 | 0 | 0 |
| Disallowed (%) | 0 | 0 | 0 | 0 |

$CVN_2$ L10 Structure.

Figure 16:
FIG. 16 provides a diagram of the CVN$_2$ L10 structure compared to WT CVN. CVN$_2$ L10 is shown in black and the domain-swapped WT CVN (3EZM.pdb) is shown in gray. These structures have an RMSD of 0.353 Å. Four of the ten linker residues have electron density and are shown in the left domain of the structure. The other six residues are not modeled in this structure.

The crystal structure of $CVN_2$ L10 indicates that this protein is also very similar to WT CVN, as shown in FIG. 16. The two structures have an RMSD of 0.353 Å and the only significant differences between the two structures are in the domain-swap area and some of the backbone phi and psi angles of the beta strands. The $CVN_2$ L10 structure forms more optimal beta strands in many cases than previously solved WT structures.

Figure 17:
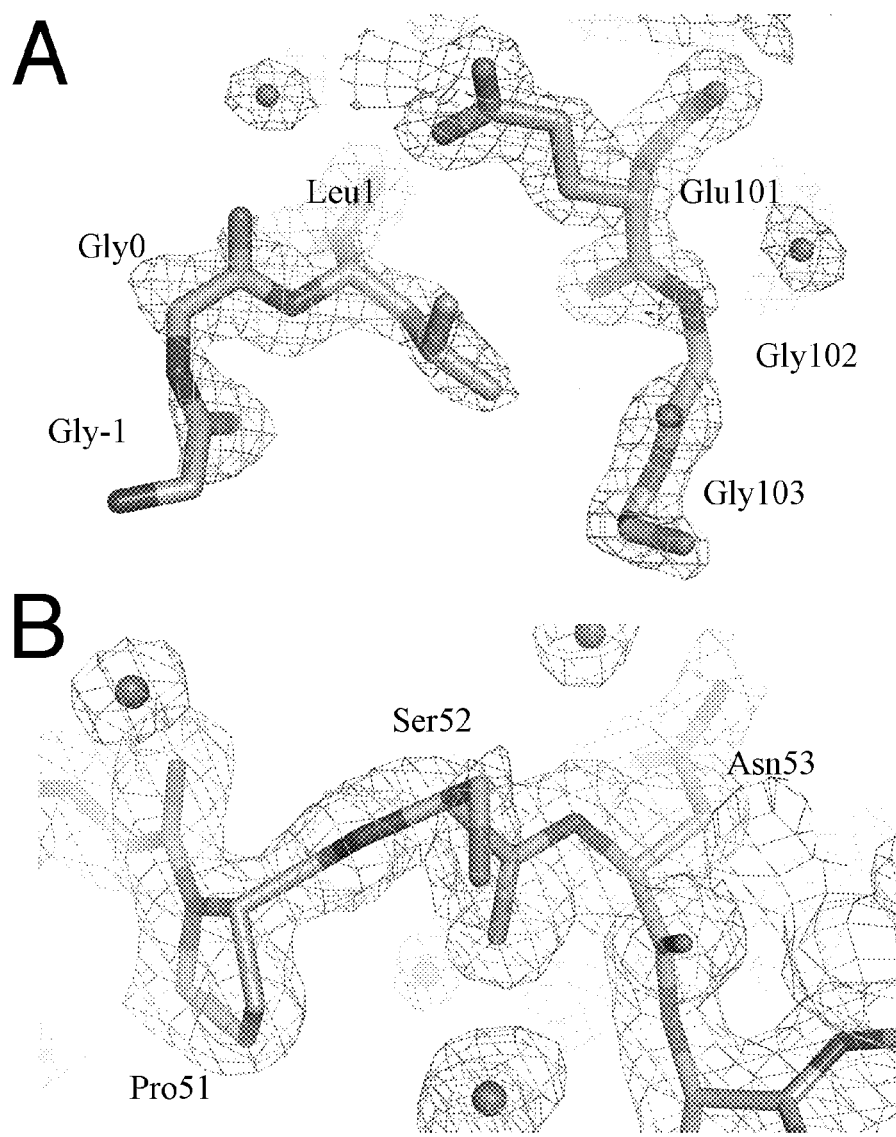
FIG. 17 provides a diagram of the CVN$_2$ L10 structure. Only half of CVN$_2$ L10 was in the asymmetric unit of this structure, therefore the linker residues are only 50% occupied. (A) The termini of the crystal structure with the 2Fo-Fc map contoured to 1.0σ. Leu1 and Glu101 are both occupied at 100%, whereas the four linker residues with visible density are at 50% occupancy. (B) This structure is domain-swapped as evidenced by the clear electron density in the domain-swapping region (residues 51-53).

Like all of the other $P3_221$ structures, only half of the $CVN_2$ L10 molecule is in the asymmetric unit. However, because the 10 amino acid linker is long and flexible, the N- and C-termini appear to be identical when free and when linked. It was therefore possible to fit four of the linker residues (two glycines on each terminus) at 50% occupancy while leaving Leu1 and Glu101 as 100% occupied, as shown in FIG. 17A. There was no clear density for the six residues in the center of the linker, so they are not included in the structure.

$CVN_2$ L10 is also definitively domain-swapped and contains several structural water molecules to stabilize this conformation, as shown in FIG. 17B. The $CVN_2$ L10 data set was molecularly replaced with a monomeric CVN model, and domain-swapping density was clear, indicating in this case, as in the previous cases, the domain swapping is not an artifact of the replacement and refinement process.

Conclusions

Four crystal structures of three different $CVN_2$ variants with linkers containing zero, one, and ten amino acids in accordance with the current invention were solved. Despite the increased potency of these proteins, the structures are all remarkably similar to domain-swapped WT CVN crystal structures. All four structures are intramolecularly domain-swapped and show varying amounts of density for the flexible polypeptide linker. The RMSDs for the structures as compared to WT were all less than 0.5 Å and the minor differences were typically observed in the domain-swap region.

Complicating the structure refinement was the fact that three of the four structures contained only half of the $CVN_2$ molecule in the asymmetric unit. In these cases, the molecule could align in two possible orientations: one with the free termini in a given location and another with the linked termini in the same location. This led to an additional plane of symmetry where the two halves of the $CVN_2$ were generated by crystallographic symmetry and the free and linked termini were each represented by the same density at 50% occupancy each.

The crystal structures of three $CVN_2$ molecules showed no major differences from WT CVN. Because the structures are remarkably similar, it is clear that linking two repeats of CVN, in accordance with the method of the current invention, does not negatively affect the structure and does not cause any major perturbations. In addition, the linkage stabilizes the domain-swapped form over the monomeric form due to the steric restraints provided by a short linker and the increase in local concentration; therefore, the proteins form obligate domain-swapped dimers. All of the structures are intramolecularly domain-swapped, and it is clear from these results that this is the biologically relevant conformation in solution. In contrast, had the crystals contained intermolecularly domain-swapped $CVN_2$ protein, it would have been possible to infer that the molecule in solution was monomeric-like.

Although not to be bound by theory, it is theorized that by stabilizing the domain-swapped dimer, the distances between the four carbohydrate binding sites in $CVN_2$ are being rigidified. Although the two domains may sample various conformations with respect to each other, as demonstrated by the differences between the $P3_221$ and $P4_12_12$ structures, the carbohydrate binding sites in both cases are brought together and held in close proximity in the domain-swapped form. For example, in the domain-swapped dimer crystal structure of WT CVN in the $P4_12_12$ space group, each of the four carbohydrate binding sites is approximately 30 to 40 Å from the other sites, as shown in FIG. 9. This geometry appears to be ideal for interacting with gp120 glycosylation, and by stabilizing this form it appears that the affinity of interaction is being increased. Additional support for this mechanism comes from the crystal structure of 2G12, a broadly neutralizing anti-HIV antibody that is also specific to the glycosylation on gp120. Unlike the standard "Y" shaped antibodies, 2G12 contains a domain swap in the Fab region, which brings the two carbohydrate binding sites approximately 35 Å apart, a similar distance to the distances in domain-swapped CVN as shown in FIG. 9B. (See, Calarese, D. A., et al., *Science*, 300, 2065-71, 2003, the disclosure of which is incorporated herein by reference.) Instead of being highly flexible, the antigen binding region of 2G12 is fixed to enhance the interaction with gp120. The similarity in the spacing between binding sites in domain-swapped CVN and 2G12 indicates that 30 to 40 Å spacing may be biologically ideal for gp120 glycosylation binding and that efficacy can be increased by stabilizing the domain-swapped form of CVN through the oligomerizing method in accordance with the current invention.

Exemplary Embodiment 5

Lectibodies

In another embodiment of the invention, a radical new class of therapeutic protein is presented that combines the carbohydrate binding ability of a lectin with the immune system activating ability of an antibody through the fusion of a lectin and the Fc region of an antibody. These new proteins, which are referred to herein as lectibodies, allow for viral neutralization by a completely novel mode of action, and have the potential to act both in a pre-exposure prophylactic mode as well as a post-exposure therapeutic mode.

In the following examples data is presented that demonstrates that a lectibody based on a CVN-Fc fusion is as effective at neutralizing HIV infection as is wild-type CVN. In addition, various molecules are proposed that would possess effector functions, such as, for example, ADCC-like immune function.

CVN-Fc Lectibody

As previously discussed, CVN is a protein that is a broadly potent inhibitor of many enveloped viruses, including HIV, Ebola, hepatitis C, herpes, and influenza. It acts to neutralize these viruses by binding to glycoproteins on the viral envelope and preventing viral fusion to the host cell. Although CVN has already been shown to be quite effective against these viruses, in another embodiment a variant of CVN is formed that has more potential therapeutic value by recruiting activities of the human adaptive immune system. Specifically, a CVN-Fc chimeric fusion protein has been formed in accordance with the current invention. This protein, termed a "lectibody" for its fusion of a lectin (CVN) and the constant region (Fc) of an antibody, is designed to incorporate the viral neutralization properties of CVN with Fc-mediated effector functions, such as antibody-dependent cell mediated cytotoxicity (ADCC), complement-dependent cytotoxicity (CDC), increased serum half-life, and antibody-dependent cell-mediated phagocytosis (ADCP).

Introduction

Antibodies are a vital component of the mammalian adaptive immune system. They are responsible for neutralizing infectious particles by binding to them and directly inhibiting them as well as by recruiting other components of the immune system, including macrophages, neutrophils, and natural killer (NK) cells, to the site of an infection. (See, Janeway, C., *Immunobiology: the immune system/in health and disease*, 6th edit, Garland Science Publishing, New York, N.Y., 2005; and Huber, M. & Trkola, A., *J Intern Med*, 262, 5-25, 2007, the disclosures of each of which are incorporated herein by reference.) As is well-known, an antibody consists of two major regions, the variable region (Fab) and the constant region (Fc). The Fab portion of the antibody is highly variable and is specific to the antigen, whereas the relatively conserved Fc portion contains binding sites for Fc receptors (FcRs) and engages the immune effector functions. There are five major isotypes of antibodies: IgM, IgA, IgD, IgE, and IgG; these differ in their heavy chain sequence and oligomerization state and mediate different responses. While all of these isotypes are important in an immune response, IgG is the most abundant antibody type found in humans, has the longest serum half-life, and is involved in most of the major effector functions. For these reasons, the Fc of IgG1 was chosen for this study, although other isotypes may prove to be beneficial in future constructs and designs.

In addition to direct neutralization of potential pathogens via the Fab regions of an antibody, effector functions mediated through Fc binding are vital to a normally functioning immune system. The Fc of IgG1 specifically interacts with FcRn and Fc receptors specific to the γ chain (FcγR), including FcγRI, FcγRII, and FcγRIII. (See, Daeron, M., *Annu Rev Immunol*, 15, 203-34, 2007; Raghavan, M. & Bjorkman, P. J., *Annu Rev Cell Dev Biol*, 12, 181-220, 1996; and Gessner, J. E., et al., *Ann Hematol* 76, 231-48, 1998, the disclosures of each of which are incorporated herein by reference.) These receptors act as messengers, linking antibody-mediated responses to cellular responses. The interaction between Fc and FcRn is involved in recycling antibodies, thereby extending their lifetime in vivo, and in transporting antibodies across epithelial barriers. (See, Bitonti, A. J., et al., *Proc Natl Acad Sci USA*, 101, 9763-8, 2004; Dumont, J. A., et al., *J Aerosol Med*, 18, 294-303, 2005; and Low, S. C., et al., *Hum Reprod*, 20, 1805-13, 2005, the disclosures of each of which are incorporated herein by reference.) The other FcγRs, when complexed with antigen-bound IgG1, can mediate antibody-dependent cell-mediated cytotoxicity (ADCC), antibody-dependent cell mediated phagocytosis (ADCP), and endocytosis. In addition to FcR-mediated cellular responses, Fc can also activate the complement pathway, which leads to cell lysis or phagocytosis. (See, Jefferis, R., et al., *Immunol Rev*, 163, 59-76, 1998, the disclosure of which is incorporated herein by reference.)

Due to their simple protein A-based purification, extended in vivo lifetime, and Fc-mediated effector functions, Fc fusion proteins have become increasingly popular. (See, Ashkenazi, A., et al., *Int Rev Immunol*, 10, 219-27, 1993; Chamow, S. M. & Ashkenazi, A., *Trends Biotechnol*, 14, 52-60, 1996; Jazayeri, J. A. & Carroll, G. J., *BioDrugs*, 22, 11-2, 2008, the disclosures of each of which are incorporated herein by reference.) At least six Fc fusion proteins are currently used clinically for several indications, including asthma, psoriasis, and rheumatoid arthritis. (See, Jazayeri, J. A., 2008, cited above.) In addition, countless other fusions have been made for both pharmaceutical and basic research purposes. While many researchers are interested in the increased lifetime of small, soluble proteins that is conferred by addition of an Fc, Fc fusions have also been used to display Fc in a reverse orientation in order to study Fc-mediated effector functions, to investigate protein-protein interactions, and as potential therapeutics for various diseases or conditions. (See, Stabila, P. F., et al., *Nat Biotechnol*, 16, 1357-60, 1998; Gurbaxani, B. M. & Morrison, S. L., *Mol Immunol* 43, 1379-89, 2006; Dwyer, M. A., et al., *J Biol Chem*, 274, 9738-43, 1999; and Shapiro, R. I., et al., *Protein Expr Purif*, 29, 272-83, 2003, the disclosures of which are incorporated herein by reference.) One particularly relevant Fc fusion is CD4-Fc. (See, Capon, D. J., et al., *Nature*, 337, 525-31, 1989; and Langner, K. D., et al., *Arch Virol* 130, 157-70, 1993, the disclosures of each of which are incorporated herein by reference.) Various constructs combining the soluble portion of the HIV receptor CD4 with the Fc domain of an antibody were investigated for inhibition of HIV In vivo. Unfortunately, the results of clinical trials on these specific constructs were disappointing, but the constructs were able to induce ADCC of HIV-infected cells in culture and were efficiently transferred across the placenta in non-human primates. (See, Byrn, R. A., et al., *Nature*, 344, 667-70, 1990, the disclosure of which are incorporated herein by reference.)

The ability to incorporate extended in vivo lifetimes and activation of cell-mediated effector functions is a very compelling reason to engineer Fc fusion proteins. Additionally, these Fc-mediated functions can be modulated through mutations in the Fc region to either increase or abrogate the response, providing more flexibility to the system. (See, Presta, L. G., *J Allergy Clin Immunol* 116, 731-6, 2005; and Presta, L. G., *Curr Opin Immunol*, 20, 460-70, 2008, the disclosures of each of which are incorporated herein by reference.) Various studies have indicated that single point mutations or changes in the Fc-linked carbohydrate composition can dramatically increase the ADCC response by increasing the affinity for FcγR. (See, Lazar, G. A., et al., *Proc Natl Acad Sci USA*, 103, 4005-10, 2006; Shields, R. L., et al., *J Biol Chem*, 276, 6591-604, 2001; Shields, R. L., et al., *J Biol Chem*, 277, 26733-40, 2002; and Shinkawa, T., et al., *J Biol Chem*, 278, 3466-73, 2003, the disclosures of which are incorporated herein by reference.)

Engineered mutations in the Fc have been shown to increase activation of the complement pathway. (See, Idusogie, E. E., et al., *J Immunol*, 166, 2571-5, 2001, the disclosure of which is incorporated herein by reference.) Alternatively, Lazar et al. showed that a point mutation could destroy the ability for an Fc to activate complement dependent cytotoxicity (CDC) while retaining or enhancing ADCC and other effector functions. (Lazar G. A., 2006, cited above.) Extending the lifetime of Fc fusions has also been extensively studied. Even though Fc-fused proteins often already have longer in Vivo lifetimes than the unfused molecule, any improvements in the circulatory half-life of a molecule is a possible benefit for potential therapeutics. A 2- to 2.5-fold increase in the half-life of Fc fusions was accomplished by either a single or double point mutation in the Fc. (See, Hinton, P. R., et al., *J Biol Chem*, 279, 6213-6, 2004; and Hinton, P. R., et al., *J Immunol*, 176, 346-56, 2006, the disclosures of each of which are incorporated herein by reference.) The incorporation of one or more of these mutations allows researchers to specifically study the effects of ADCC, complement, and half-life on a particular system.

ADCC is triggered by the interaction of the Fc domain of antigen-bound IgG to the CD16 receptor expressed on the surfaces of immune effector cells, particularly natural killer (NK) cells. Recent in vivo data indicate that CD16-dependent ADCC activity may be critical to the ability of passively administered gp120-reactive IgG to block HIV infection. (See, Hessell A. J., L., et al., *Nature*, 449: 101-104, 2007, the disclosure of which is incorporated herein by reference). To date, multiple groups have successfully characterized the abilities of various broadly neutralizing anti-HIV monoclonal antibodies to recruit ADCC In vitro. (See, e.g., Ahmad A, et al., *J Acquir Immune Defic Syndr*, 7: 789-798, 1994; Ahmad R, et al., *J Clin Immunol*, 21: 227-233, 2001; Gupta N, et al., *Virology*, 332: 491-497, 2005; Gomez-Roman V R, et al., *J Immunol*, 174: 2185-2189, 2005; and Gomez-Roman V R, et al., *J Immunol Methods*, 308: 53-67, 2006, the disclosures of each of which are incorporated herein by reference.) Based on these previously described results, it should be possible to engineer ADCC recruitment by the lectibodies of the current invention when expressed as fusions with the human IgG subtype 1 Fc domain using equivalent assays.

The protein of interest in this study, as described before, cyanovirin-N (CVN), is a small cyanobacterially-derived protein that inhibits infection by various enveloped viruses including HIV, Ebola, and influenza. (See, Boyd, M. R., et al., *Antimicrob Agents Chemother*, 41, 1521-30, 1997; Barrientos, L. G., et al., *Antiviral Res*, 58, 47-56, 2003; and O'Keefe, B. R., et al., *Antimicrob Agents Chemother*, 47, 2518-25, 2003, the disclosures of each of which are incorporated herein by reference.) CVN is a lectin that specifically binds α1-2 linked high-mannose molecules. (See, Bewley, C. A., *Structure*, 9, 931-40, 2001; Botos, I., et al., *J Biol Chem*, 277, 34336-42, 2002; Bolmstedt, A. J., et al., *Mol Pharmacol*, 59, 949-54, 2001; and O'Keefe, B. R., et al., *Mol Pharmacol*, 58, 982-92, 2000, the disclosures of each of which are incorporated herein by reference.) This type of carbohydrate linkage is found in high concentrations on the envelope proteins of these viruses, including gp120 on HIV. (See, e.g., Leonard, C. K., et al., *J Biol Chem*, 265, 10373-82, 1990, the disclosure of which is incorporated herein by reference.) CVN effectively neutralizes HIV by binding with high affinity and avidity to the glycosylation on gp120 and blocking interactions with the host cell receptor, CD4, and co-receptors. (See, Dey, B., et al., *J Virol*, 74, 4562-9, 2000, the disclosure of which is incorporated herein by reference.)

Figure 18:
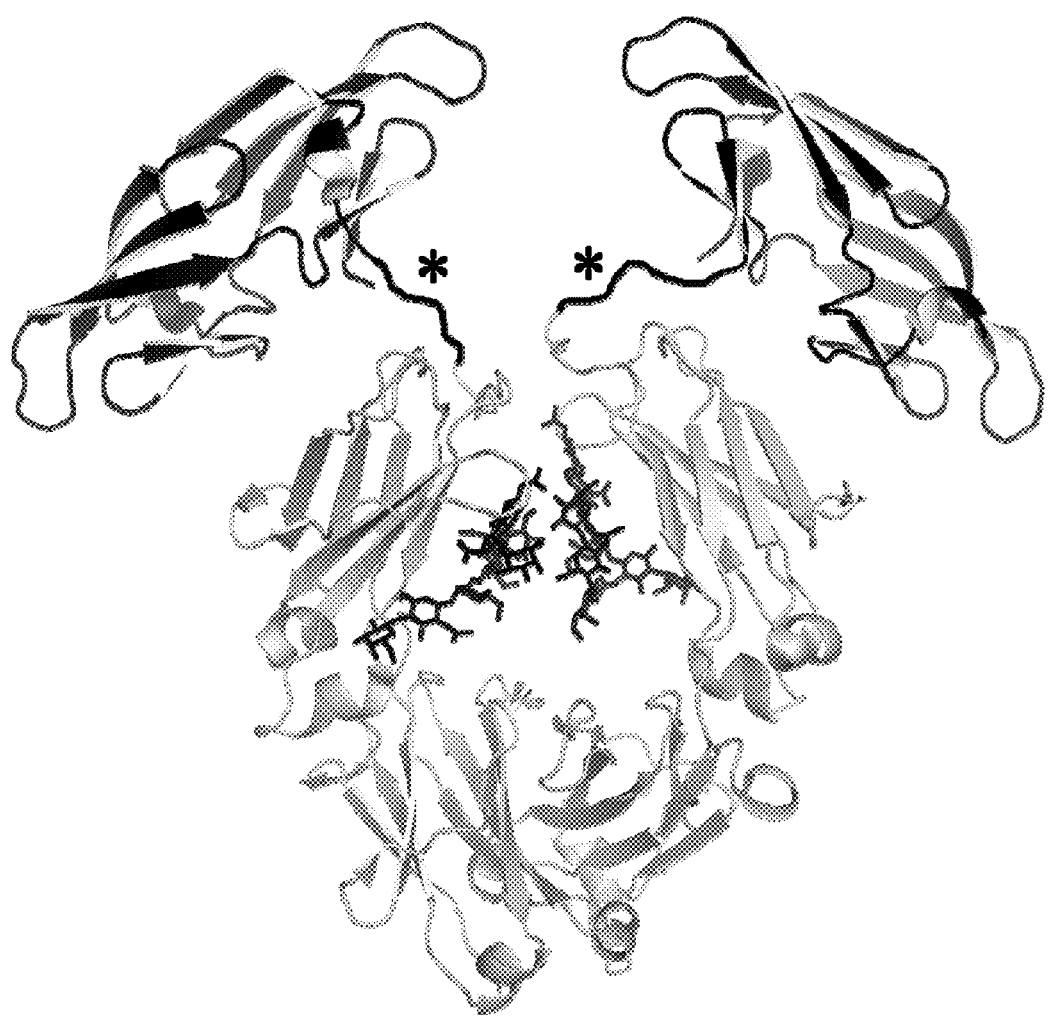
FIG. 18 provides a diagram of a model CVN-Fc lectibody. The CVN monomers are shown in black attached to the Fc (gray) through flexible polypeptide linkers shown with an asterisks (*). The Fc glycosylation is shown in stick representation with black atoms. This model was created by combining a monomeric NMR structure of CVN and the Fc from the IgG1b12 crystal structure (1HZH) and is not a solved structure of this variant.

In accordance with the current invention, a CVN-Fc fusion (lectibody) is formed that retains wild-type (WT) CVN-like HIV neutralization activity, the results of which are discussed below. This construct is referred to as a "lectibody" as it is a fusion between a lectin (CVN) and the Fc of an antibody, a model of which is shown in FIG. 18. Data showing the viability of a CVN-Fc fusion: a lectibody is provided with this exemplary embodiment. This new class of antiviral protein should also be able to act to neutralize free viral particles, and it is believed will also be able to invoke an ADCC-like immune response surrounding virus-infected cells.

Methods

Construct generation. Lectibody constructs were created by subcloning the WT CVN sequence or the CVN2 L0 sequence described in Exemplary Embodiment 1 including DNA that encodes a five-amino acid linker (GGSGG; SEQ. ID. 1) between CVN and the Fc of human IgG1 into the baculovirus expression vector pAc-κ-Fc using the XhoI and SpeI restriction sites (Progen Biotechnik). Sequencing on this construct revealed that the Fc portion was missing the last eight residues and included two point mutations. To rectify this, the last eight Fc residues were added during the second cloning step in which the secretion signal, CVN, and Fc were subcloned using PCR-based techniques into the mammalian expression vector pcDNA3.1 (Invitrogen) or pTT5 (NRC Biotechnology Research Institute), and the mutations were reversed to give the WT Fc sequence. Human-codon optimized CVN sequences were determined using the Custom Gene Synthesis program from IDT (Integrated DNA Technologies, Inc). The optimized gene was assembled via recursive PCR and ligated into the pcDNA3.1 or pTT5 vector already containing the secretion leader sequence and the Fc sequence. Point mutations were introduced into the lectibody constructs using the QuikChange Site-Directed Mutagenesis kit (Stratagene).

All constructs were verified through DNA sequencing. Bacterially expressed constructs were created as described in Exemplary Embodiment 1. Point mutations for bacterially expressed variants were introduced using the QuikChange Site-Directed Mutagenesis kit (Stratagene).

Expression and Purification.

Lectibody constructs were expressed in transiently transfected, suspended HEK293-T or HEK293-6E cells (NRC Biotechnology Research Institute). The cells were transfected with 1 mg of plasmid DNA per liter of culture using a polyethylenimine-mediated transfection protocol (PEI). The secreted protein was harvested from the cell supernatants after 6-8 days and buffer exchanged into 100 mM sodium phosphate buffer pH 7.5, 150 mM NaCl. The protein was purified on a Protein A column, eluted in pH 3.0 elution buffer (Pierce) and immediately neutralized with Tris base. A second purification step on a Superdex-200 gel filtration column (GE Healthcare) in 25 mM sodium phosphate pH 7.4, 150 mM NaCl was used to separate high molecular weight aggregates from smaller species. Protein was stored as eluted or concentrated in a 10,000 MWCO centrifugal concentrator (Millipore) then kept at 4° C.

Deglycosylation of lectibody proteins was accomplished using PNGase F (New England Biolabs). The protein was denatured, then PNGase F was added according to the manufacturer's protocol. Complete deglycosylation was achieved after 1-2 hours. After removing the carbohydrates, the apparent molecular weights of the proteins were assessed by SDS-PAGE.

Bacterial expression and purification of non-Fc fusion constructs were performed as described in Exemplary Embodiment 1.

Circular Dichroism.

Circular dichroism (CD) spectra were obtained on an Aviv 62DS spectrometer with a 1 mm path length cell. Samples were 50 µM protein in 25 mM sodium phosphate buffer, pH 7.4, 150 mM NaCl. Wavelength scans were collected at various temperatures between 200 and 250 nm with a 1 nm step size. A single scan was collected for each variant with an averaging time of 5 sec. Temperature denaturation was monitored at 233 nm from 1° C. to 99° C. The sample was equilibrated at each temperature for a minimum of 2 minutes before the data was averaged for 30 seconds and recorded.

The denaturation curves were not reversible and therefore thermodynamic parameters could not be determined. Instead, the data were fit to a two-state model to estimate the midpoint of thermal denaturation (Tm), an estimate of thermal stability. (See, Becktel, W. J. & Schellman, J. A., *Biopolymers,* 26, 1859-77, 1987, the disclosure of which is incorporated herein by reference.)

Neutralization Assays.

Neutralization assays were performed as described in Exemplary Embodiment 1. (See, Li, M., et al., *J Virol,* 79, 10108-10125, 2005, the disclosure of which is incorporated herein by reference.) All variants were tested against strain SC422661.8 from clade B and compared to WT CVN from the same 96-well plate unless otherwise noted. Due to the low concentrations of various constructs, some assays were performed with twice the standard volume of protein to increase the final concentration in the well.

Surface Plasmon Resonance (SPR).

SPR experiments were conducted on a T100 instrument from Biacore. Approximately 30 response units (RUs) of bacterially expressed WT CVN were immobilized on a CM5 chip using standard amine coupling. All assays were conducted in HBS-EP buffer (10 mM HEPES pH 7.4, 150 mM NaCl, 0.0005% v/v Surfactant P20, 1 mM EDTA; Biacore). Various analytes were injected over the surface for 60 seconds at a flow rate of 30 µL/min. The chip was regenerated with two pulses of 50 mM NaOH. Complete regeneration was not achieved after lectibody variants were analyzed and therefore proteins injected later may have exhibited binding to the unregenerated surface and not to the surface itself. In these cases the assay was repeated on a new surface and the samples were tested in reverse order to confirm the results of the first experiment. The data were analyzed for binding or lack of binding based on the sensorgram.

Results

Mammalian Expression.

All CVN-Fc (lectibody) constructs were expressed and secreted in mammalian cell culture. Yields were typically low for the pcDNA constructs with *Escherichia coli*-optimized CVN sequences (between 100 and 500 µg protein per L of cell culture). For comparison, a similar construct containing only the expression leader sequence and Fc expressed approximately 4 mg/L. To try to resolve this problem, various constructs were made to increase protein expression. It was found that changing the vector from pcDNA3.1 to pTT5 did not significantly improve the expression and in multiple trials actually produced a larger fraction of degradation product. It was discovered that changing the codons of the CVN gene to correspond with optimal human codon usage produced an approximately 10% increase in soluble expression.

Glycosylation.

After Protein A purification, the initial lectibody construct, CVN-Fc, appeared to migrate much slower on an SDS-PAGE gel than expected (data not shown). Therefore, the protein was deglycosylated to confirm the expected molecular weight. However, upon deglycosylation, it became clear that the protein contained two separate N-linked glycosylation sites instead of only the expected site on the Fc. The NetNGlyc 1.0 Server was used to predict potential N-linked glycosylation sites and found a highly probable site at position 30 of the CVN sequence in addition to the known glycosylation site in the Fc. (See, Gupta, R., et al., In preparation at http://www.cbs.dtu.dk/services/NetNGlyc/, 2004, the disclosure of which is incorporated herein by reference.) This potential glycosylation site in CVN is located on the surface of the protein and has the sequence N-T-S, which is consistent with the N-X-(S/T) consensus sequence for N-linked glycosylation (where X is any amino acid except proline). (See, Imperiali, B. & O'Connor, S. E., *Curr Opin Chem Biol* 3, 643-9, 1999, the disclosure of which is incorporated herein by reference.) Visual inspection of the NMR and crystal structures indicated that glycosylation of residue 32 may interfere with substrate binding since this residue is near one of the binding sites of CVN. This result was confirmed by HIV neutralization assays, which showed that CVN-Fc had no neutralization activity (data not shown).

To remove the non-native glycosylation site in CVN, four variants were constructed in the bacterially expressed WT background to assess their effect on the structure and function of CVN. Both N30 and S32 make side chain-backbone hydrogen bonds in the crystal structure, so two variants were constructed for each position, an Ala mutation that deleted the side chain and a polar mutation that may be able to satisfy the hydrogen bond (N30S and S32N). (See, e.g., U.S. Pat. No. 6,780,847, the disclosure of which is incorporated herein by reference.) An S32T mutation would have possibly satisfied the hydrogen bond requirement, but it would have also met the glycosylation consensus and therefore would not have destroyed the site.

Figure 19:
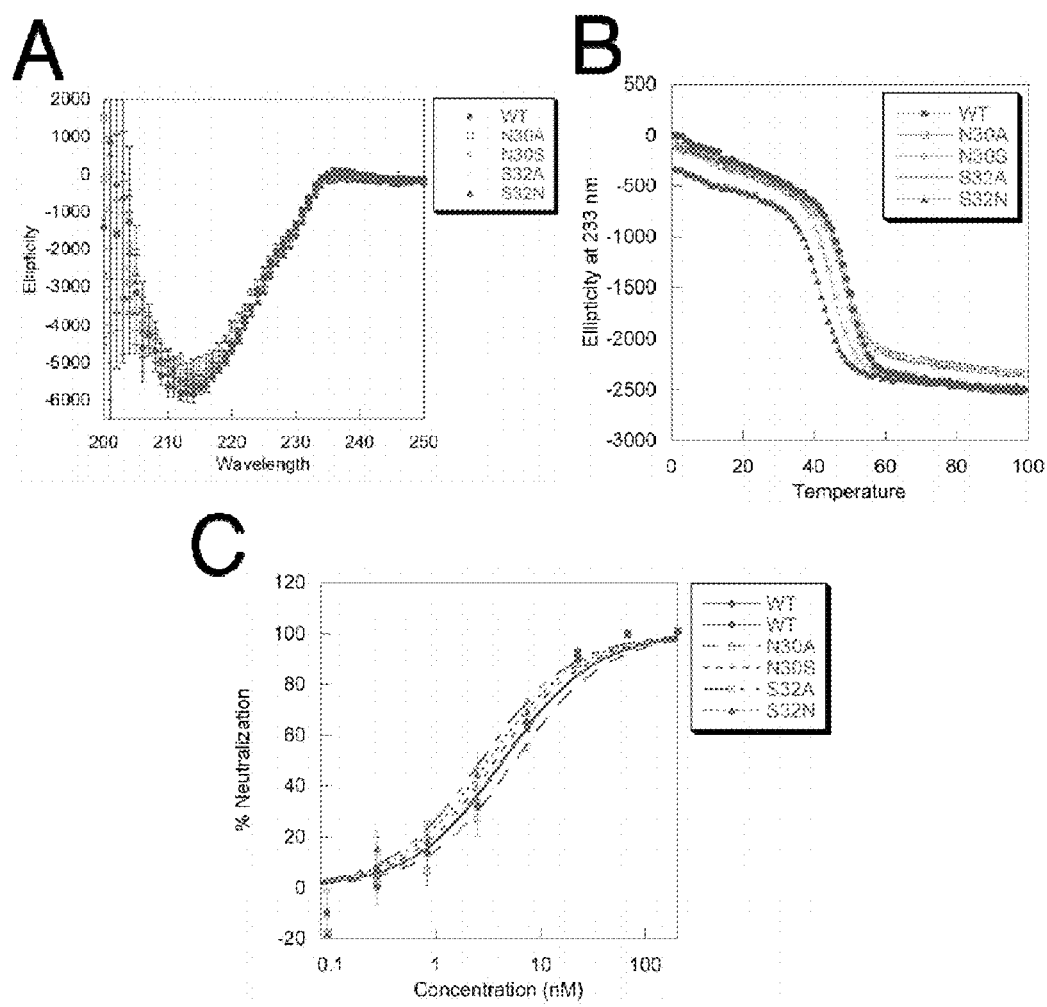
FIG. 19 provides an assessment of glycosylation site deletion variants. (A) CD wavelength scans of the four variants compared to WT CVN. (B) Thermal denaturation of WT and the variants monitored by CD at 233 nm. (C) HIV neutralization curves of glycosylation site variants and WT.

The four glycosylation deletion variants were assayed for changes in their secondary structure and thermal stability by CD, and their HIV neutralization abilities were compared to WT. The results are shown in FIG. 19. No significant differences were seen in the CD wavelength scans of the four variants compared to WT CVN, indicating that the secondary structure was not affected by the mutation as shown in FIG. 19A. Slight differences were observed in the midpoint of thermal denaturation (Tm) of the variants; however, as shown in FIG. 19B. WT and the two N30 mutants had Tms that were within experimental error (48.8° C. to 49.8° C.), whereas S32A and S32N were destabilized by approximately 5° C. and 8° C., respectively. The neutralization assays showed that the N30A variant was slightly less active than WT, whereas the other three variants were WT-like in their HIV neutralization, as shown in FIG. 19C. All this data together indicated that N30S was the best mutation to incorporate into the lectibody construct. N30S in the background of WT CVN had WT-like HIV neutralization activity, secondary structure, and thermal stability. Additionally, mutation at N30 guarantees the elimination of the N-linked glycosylation, whereas mutation at position 32 leaves the Asn to which glycosylation would be attached intact, giving rise to a small possibility that glycosylation could still occur.

CVN-Fc N30S.

Figure 20:
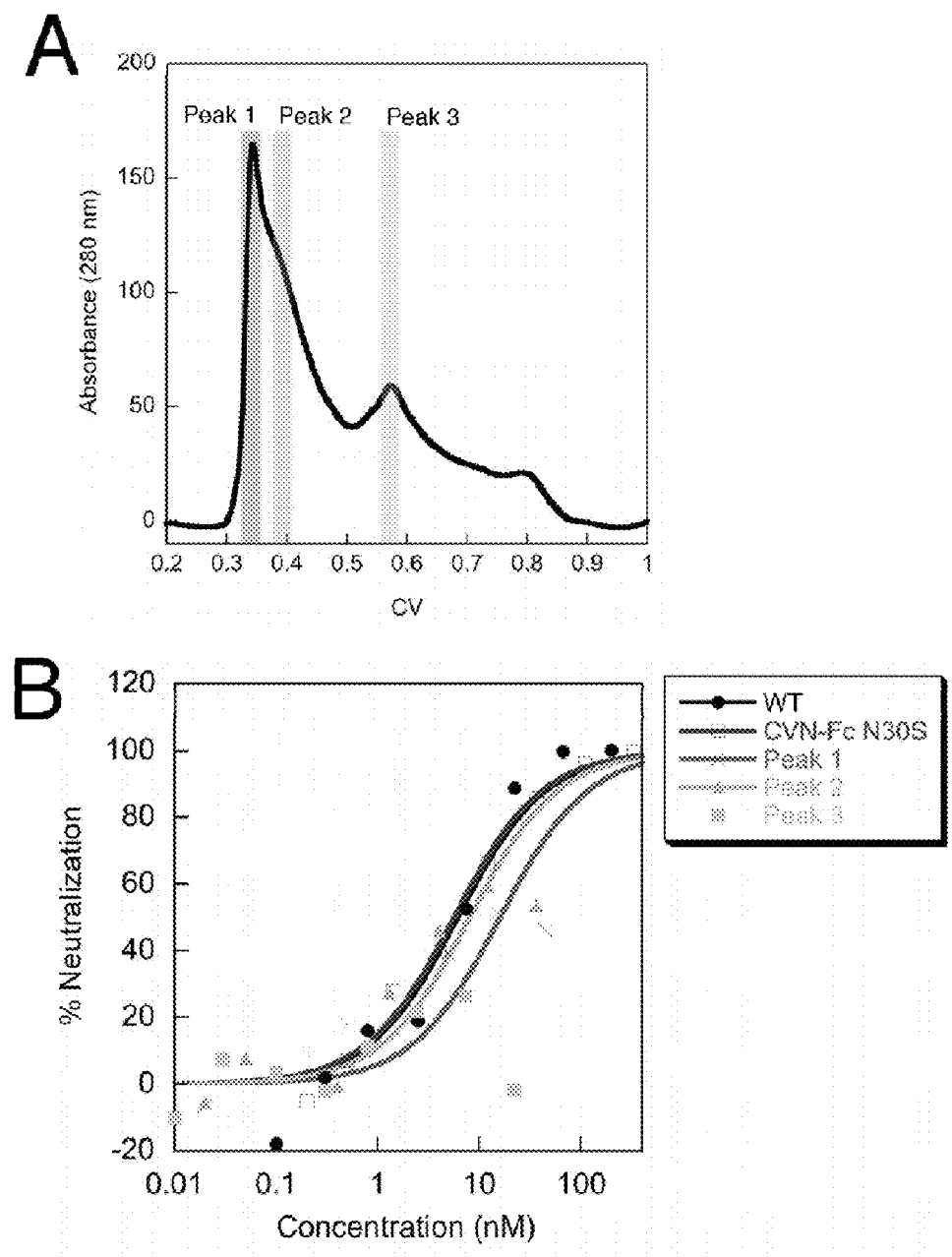
FIG. 20 provides data on CVN-Fc N30S purification and activity. (A) A gel filtration trace of CVN-Fc N30S shows that the majority of the protein forms high order oligomers. (B) CVN-Fc N30S has WT-like HIV neutralization activity, but the active protein is the high molecular weight species and not from Peak 3, which corresponds to dimeric lectibody.

After determining the ideal mutation to remove the non-native glycosylation site from CVN-Fc, CVN-Fc N30S was expressed and purified. This variant, similarly to the WT lectibody, had a significantly higher apparent molecular weight than expected as assayed by gel filtration chromatography, due to higher order oligomers or to aggregation, as shown in FIG. 20. The expected elution volume for dimeric lectibody was approximately 0.60 CV. Although the majority of the protein elutes in the void volume, there was a small peak approximately corresponding to dimeric lectibody. Although Protein A purified protein and fractions containing high molecular weight species showed WT-like HIV neutralization activity, this fraction contained no activity, as shown in FIG. 20B.

This unwanted higher order oligomerization needed to be addressed so that monodispersive samples could be obtained for assaying. It was hypothesized that the low pH elution from the Protein A column may cause some partial denaturation of the CVN portion of the lectibody. Accordingly, the secondary structure was assessed for potential changes in oligomerization, and HIV neutralization of WT bacterially-expressed CVN at various pHs (data not shown). These experiments showed no significant differences between protein in pH 7.4 buffer and protein in buffers down to pH 2.0, including the actual Protein A elution buffer (Pierce). It can therefore be conclude that WT CVN does not show a pH dependence for the general secondary structure, HIV neutralization, or oligomerization.

Another possibility for the higher order oligomers formed by the lectibodies was that CVN, a carbohydrate binding protein, was binding the glycosylation on Fc and therefore causing large complexes of protein specifically bound to other lectibodies. To test this hypothesis, the lectibody was expressed with an additional mutation (N181A, equivalent to position 297 in a full length heavy chain) that eliminates the native Fc glycosylation site. This variant (CVN-Fc noglycos) behaved similarly to CVN-Fc N30S, and most of the protein eluted near the void volume of the gel filtration column, indicating it was almost completely composed of higher order oligomers. There was no apparent molecular weight-shift upon deglycosylating this sample, indicating that all of the N-linked glycosylation sites had been removed. Although almost entirely oligomerized, CVN-Fc noglycos that was eluted from the Protein A column had approximately WT-like activity (as compared to bacterially expressed WT CVN) in the HIV neutralization assay, indicating that glycosylation is not necessary for the proper folding of the protein or for the activity, as expected.

Figure 21:
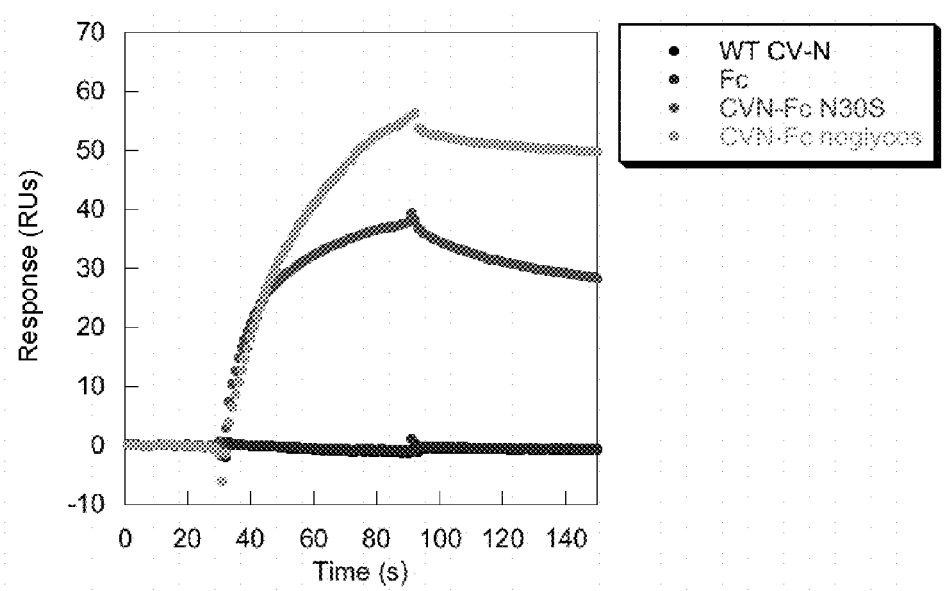
FIG. 21 provides surface plasmon resonance assays of lectibodies and Fc. WT CVN was immobilized on the surface and various proteins were analyzed for binding. WT CVN and human glycosylated Fc did not bind to the surface. However, both lectibody constructs (CVN-Fc N30S and CVN-Fc noglycos) showed significant interaction with the WT CVN surface that could not be regenerated.

Whether glycosylated Fc could bind WT CVN in an SPR assay was also tested and the results summarized in FIG. 21. No evidence of binding to immobilized CVN was seen, and therefore it was concluded that CVN does not bind the carbohydrate on Fc. Interestingly, as seen in FIG. 21, significant amounts of binding of CVN-Fc N30S and CVN-Fc noglycos to the WT CVN surface was seen. Because it is known that the Fc is not responsible for the binding, it can be deduced that the CVN component of the lectibody is aggregating on the surface. WT CVN, on the other hand, shows no evidence of binding the CVN surface. This evidence suggests that the lectibody, although it contains some active and therefore properly folded protein, probably contains some misfolded protein, which has a tendency to aggregate. Additionally, the lectibody could have alternate domain-swapping properties for the CVN component, leading to intermolecular domain swapping, with either WT CVN or another lectibody protein.

Domain-Swapping Variant Lectibodies.

To assess whether domain swapping of CVN is contributing to the formation of higher order oligomers, two new constructs, $CVN_2$ L0-Fc and N30S/P51G-Fc, were created and assayed. In Exemplary Embodiment 1, dimeric variants of CVN are described that were used to test the effects of oligomerization on the efficacy of HIV neutralization. In that example it was shown that by covalently linking the termini of two copies of CVN it is possible to stabilize the domain-swapped dimeric form of CVN, which in the context of WT is only metastable.

Figure 22:
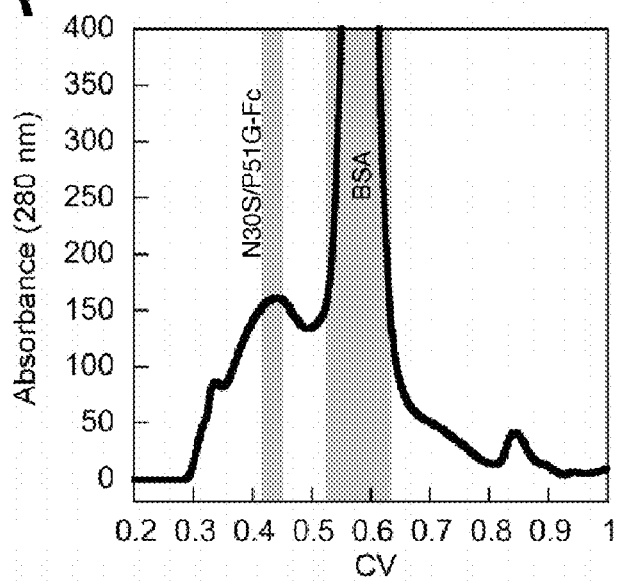
FIG. 22 provides N30S/P51G-Fc purification and activity. (A) Gel filtration of N30S/P51G CVN-Fc shows a broad peak corresponding to the lectibody around 0.44 CV. (B) N30S/P51G CVN-Fc is active both before and after gel filtration. A reference curve from a previous assay for WT is also shown. The small void volume peak and the BSA peak both showed no anti-HIV activity (data not shown).
Figure 22:
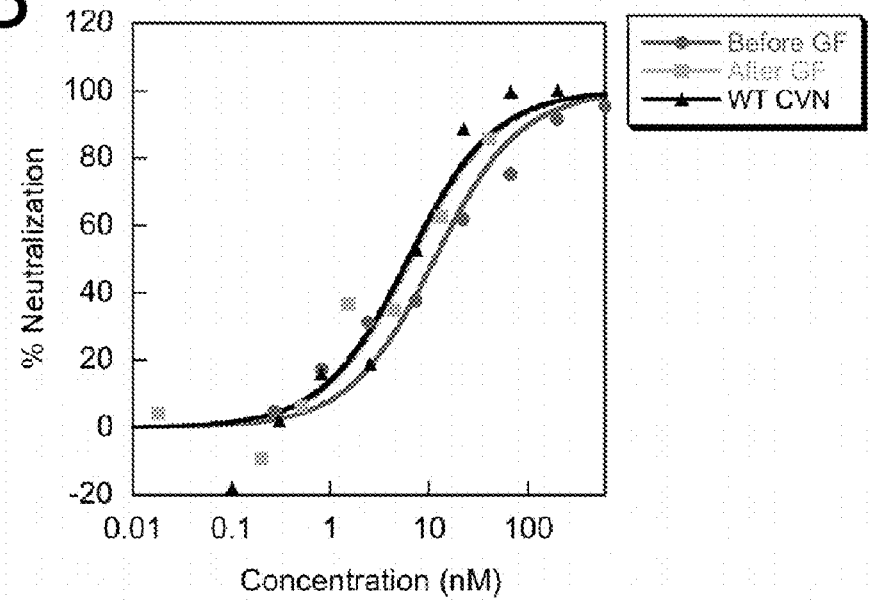

As a result, the $CVN_2$ L0 variant described in Exemplary Embodiment 1 should be stably domain-swapped and should not interact with other molecules to form intermolecularly domain-swapped complexes. While the $CVN_2$ L0-Fc variant showed a significantly lower proportion of high molecular weight species, this protein was not active against HIV. When the N30S mutation is added to this construct, the majority of protein was shifted to high molecular weight and it remained inactive in the HIV neutralization assay. The second domain-swapping variant appears to hold more promise. In this case, the P51G mutation was added to CVN-Fc N30S. P51G has been shown to shift the equilibrium toward monomeric protein and destabilize the domain-swapped form. (See, Barrientos, L. G., et al., *Structure,* 10, 673-86, 2002, the disclosure of which is incorporated herein by reference.) N30S/P51G CVN-Fc expressed much more readily in the mammalian expression system, although when it was neutralized after the Protein A column, a significant amount of protein precipitated and was lost. The remaining protein, when separated on a gel filtration column, produced a broad peak around 0.44 CV that contained N30S/P51G CVN-Fc as assayed by SDS-PAGE and showed WT-like activity in the HIV neutralization assay as summarized in the data plot of FIG. 22. A second large peak at 0.58 CV was attributed to contamination by BSA from the expression process. This peak contained no anti-HIV activity. Although the N30S/P51G CVN-Fc did not elute at the expected volume, it is not forming the very high order oligomers of previous constructs. This indicates that domain swapping is a concern in the lectibody constructs and must be accounted for.

Discussion

The data results show the successful creation of a chimeric CVN-Fc variant that shows WT-like anti-HIV activity. It has been further shown that a non-native glycosylation site is present in CVN and is glycosylated in mammalian tissue culture and that that site must be removed for efficient viral neutralization activity. In addition, it has been shown that the lectibody constructs are prone to formation of higher order oligomers, which can in part be prevented by using a variant that stabilizes the monomeric state of CVN over the domain-swapped dimer. It has also been shown that in accordance with the current invention it is possible to modulate the oligomerization through simple mutation.

Finally, the anti-HIV activity of the lectibodies formed are comparable to that of WT CVN. However, it is projected that this activity can be enhanced by refinements in the manufacturing techniques such that pure dimeric lectibody can be formed without significant contamination from partially or fully unfolded, nonfunctional protein. Additionally, some of the carbohydrate binding sites on CVN could be sterically inhibited by the high order oligomerization. Accordingly, it should be understood that generating a variant that is monodispersed and dimeric should resolve these issues.

However, beyond this neutralization activity, the lectibodies also possess antibody activity in the form of the Fc effector function. Accordingly, it is expected that the lectibody should exhibit all the potential functions of the Fc, such as, for example, antibody-dependent cell-mediated cytotoxicity (ADCC) and other effector functions, such as, increased half-life, complement-dependent cytotoxicity (CDC), and antibody-dependent cell-mediated phagocytosis (ADCP).

CONCLUSION

Lectins such as CVN were oligomerized to determine whether an increase in the number of carbohydrate binding sites has an effect on its viral neutralization activity. To create obligate dimers, multiple copies of lectins were covalently linked through flexible polypeptide linkers. Using HIV-1, influenza, and vaccinia as exemplary viral systems, it has been determined that a tandem repeat of two or more lectins increased the efficacy of viral neutralization by up to 35-fold. In addition, multimeric lectin variants show extensive cross-clade reactivity and higher neutralization efficacy for HIV than the most broadly reactive neutralizing antibodies.

Additionally, a novel lectin-Fc chimera, a "lectibody," has been developed, which shows antiviral activity similar to the wild-type lectin, CVN. This variant is dimerized through the Fc region of an antibody and has the additional benefit of incorporating Fc-mediated effector functions, which may be therapeutically advantageous. Initial results on a CVN lectibody indicate that domain swapping has an integral role in the antiviral function as well as in the overall folding and stability of the molecule.

DOCTRINE OF EQUIVALENTS

Those skilled in the art will appreciate that the foregoing examples and descriptions of various preferred embodiments of the present invention are merely illustrative of the invention as a whole, and that variations in the steps and various components of the present invention may be made within the spirit and scope of the invention. For example, it will be clear to one skilled in the art that using different lectins or developing lectibodies having slight structural or compositional modifications would not affect the improved properties of the engineered lectins or lectibodies of the current invention nor render the method unsuitable for their intended purpose. Accordingly, the present invention is not limited to the specific embodiments described herein but, rather, is defined by the scope of the appended claims.

What is claimed is:

1. A neutralization agent for an enveloped virus comprising an isolated/purified lectin oligomer or mixed lectin hetero-oligomer comprising the following structure:

$$NH_2\text{-}L\text{-}(P\text{-}L)_n\text{-}COOH$$

wherein n is at least 1, wherein each L is the same or different isolated or purified antiviral lectin, and wherein each P may be the same or different and is one of either a peptide bond or a polypeptide linker;

wherein where P is a polypeptide linker, said polypeptide linker is formed from at least 5 glycine and serine amino acids, and wherein each lectin is covalently bound to the polypeptide linker through a peptide bond to form a stable lectin oligomer or mixed lectin hetero-oligomer; and wherein said lectin oligomer operative to bind to at least one carbohydrate site on a glycosylated envelope protein of a target virus thereby neutralizing said target virus.

2. The viral neutralization agent of claim 1, wherein the lectin oligomer.

3. The viral neutralization agent of claim 1, wherein the lectins are at least two repeat lectins, selected from the group consisting of cyanovirin-N lectin (CVN), griffithsin (GRFT), scytovirin, actinohivin, defensins, *Microcystis viridis* lectin (MVL), *Oscillatoria agardhii* agglutinin, Hippeastrum hybrid agglutinin (HHA), mannose-binding lectin (MBL), and *Urtica dioica* agglutinin (UDA).

4. The viral neutralization agent of claim 1, wherein the lectins are at least two different lectins, selected from the group consisting of cyanovirin-N lectin (CVN), griffithsin (GRFT), scytovirin, actinohivin, defensins, *Microcystis viridis* lectin (MVL), *Oscillatoria agardhii* agglutinin, Hippeastrum hybrid agglutinin (HHA), mannose-binding lectin (MBL), and *Urtica dioica* agglutinin (UDA).

5. The viral neutralization agent of claim 3, wherein the lectins are directly covalently linked at the termini thereof through a peptide bond.

6. The viral neutralization agent of claim 1, wherein the oligomerization of the at least two lectins stabilized the lectin oligomer in an intramolecularly domain-swapped form.

7. The viral neutralization agent of claim 1, target virus is at least one virus selected from the group consisting of HIV, influenza, the pox viruses, the Hanta viruses, hepatitis C, herpes, SARS viruses, and hemorrhagic fever viruses including but not limited to Ebola.

8. The viral neutralization agent of claim 7, wherein the target virus is HIV and wherein the oligomer shows cross-clade and cross-strain reactivity.

9. The viral neutralization agent of claim 7, wherein the target virus is HIV, and wherein the oligomer binds to the gp120 glycoprotein of the HIV virus envelope.

10. The viral neutralization agent of claim 7, wherein the target virus is influenza, and wherein the oligomer binds to the hemagglutinin glycoprotein of the influenza virus envelope.

* * * * *

SEQUENCE LISTING

```
<160> NUMBER OF SEQ ID NOS: 11

<210> SEQ ID NO 1
<211> LENGTH: 5
<212> TYPE: DNA
<213> ORGANISM: Artificial sequence
<220> FEATURE:
<223> OTHER INFORMATION: Synthetically produced sequence

<400> SEQUENCE: 1 ggsgg                                                                    5

<210> SEQ ID NO 2
<211> LENGTH: 6
<212> TYPE: DNA
<213> ORGANISM: Artificial Sequence
<220> FEATURE:
<223> OTHER INFORMATION: Synthetically produced sequence
```

```
<400> SEQUENCE: 2 gsggsg                                                                  6

<210> SEQ ID NO 3
<211> LENGTH: 7
<212> TYPE: DNA
<213> ORGANISM: Artificial Sequence
<220> FEATURE:
<223> OTHER INFORMATION: Synthetically produced sequence

<400> SEQUENCE: 3 ggsggsg                                                                 7

<210> SEQ ID NO 4
<211> LENGTH: 8
<212> TYPE: DNA
<213> ORGANISM: Artificial Sequence
<220> FEATURE:
<223> OTHER INFORMATION: Synthetically produced sequence

<400> SEQUENCE: 4 ggsggsgg                                                                8

<210> SEQ ID NO 5
<211> LENGTH: 9
<212> TYPE: DNA
<213> ORGANISM: Artificial Sequence
<220> FEATURE:
<223> OTHER INFORMATION: Synthetically produced sequence

<400> SEQUENCE: 5 ggsgggsgg                                                               9

<210> SEQ ID NO 6
<211> LENGTH: 10
<212> TYPE: DNA
<213> ORGANISM: Artificial Sequence
<220> FEATURE:
<223> OTHER INFORMATION: Synthetically produced sequence

<400> SEQUENCE: 6 ggsggggsgg                                                             10

<210> SEQ ID NO 7
<211> LENGTH: 11
<212> TYPE: DNA
<213> ORGANISM: Artificial Sequence
<220> FEATURE:
<223> OTHER INFORMATION: Synthetically produced sequence

<400> SEQUENCE: 7
ggsggsggsg g                                                           11

<210> SEQ ID NO 8
<211> LENGTH: 13
<212> TYPE: DNA
<213> ORGANISM: artificial sequence
<220> FEATURE:
<223> OTHER INFORMATION: Synthetically produced sequence

<400> SEQUENCE: 8
ggsgggsggg sgg                                                         13

<210> SEQ ID NO 9
<211> LENGTH: 15
```

```
<212> TYPE: DNA
<213> ORGANISM: Artificial Sequence
<220> FEATURE:
<223> OTHER INFORMATION: Synthetically produced sequence

<400> SEQUENCE: 9
ggsggggsgg ggsgg                                              15

<210> SEQ ID NO 10
<211> LENGTH: 17
<212> TYPE: DNA
<213> ORGANISM: Artificial sequence
<220> FEATURE:
<223> OTHER INFORMATION: Synthetically produced sequence

<400> SEQUENCE: 10
ggsgggsggg sgggsgg                                            17

<210> SEQ ID NO 11
<211> LENGTH: 20
<212> TYPE: DNA
<213> ORGANISM: artificial sequence
<220> FEATURE:
<223> OTHER INFORMATION: Synthetically produced sequence

<400> SEQUENCE: 11
ggsggggsgg ggsggggsgg                                         20
```